US011793524B2

(12) United States Patent
Deville et al.

(10) Patent No.: US 11,793,524 B2
(45) Date of Patent: *Oct. 24, 2023

(54) RECAPTURABLE LEFT ATRIAL APPENDAGE CLIPPING DEVICE AND METHODS FOR RECAPTURING A LEFT ATRIAL APPENDAGE CLIP

(71) Applicant: Syntheon 2.0, LLC, Miami, FL (US)

(72) Inventors: Derek Dee Deville, Coral Gables, FL (US); Matthew A. Palmer, Miami, FL (US); Richard Cartledge, Boca Raton, FL (US); Thomas O. Bales, Jr., Miami, FL (US); M. Sean McBrayer, Coral Gables, FL (US); William T. Bales, Miami, FL (US); Michael Walter Kirk, Miami, FL (US); William Ragheb, Miami, FL (US); Eric Petersen, Homestead, FL (US); Carlos Rivera, Cooper City, FL (US); Vincent Turturro, Milton, GA (US)

(73) Assignee: Medtronic, Inc., Minneapolis, MN (US)

( * ) Notice: Subject to any disclaimer, the term of this patent is extended or adjusted under 35 U.S.C. 154(b) by 372 days.

This patent is subject to a terminal disclaimer.

(21) Appl. No.: 17/143,862

(22) Filed: Jan. 7, 2021

(65) Prior Publication Data

US 2021/0169489 A1 Jun. 10, 2021

Related U.S. Application Data

(63) Continuation of application No. PCT/US2020/031228, filed on May 3, 2020, which is
(Continued)

(51) Int. Cl.
| | | |
|---|---|---|
| *A61B 17/122* | (2006.01) | |
| *A61B 17/128* | (2006.01) | |
| *A61B 17/00* | (2006.01) | |

(52) U.S. Cl.
CPC ........ *A61B 17/122* (2013.01); *A61B 17/1285* (2013.01); *A61B 2017/00243* (2013.01)

(58) Field of Classification Search
CPC .................... A61B 17/128; A61B 17/1285
See application file for complete search history.

(56) References Cited

U.S. PATENT DOCUMENTS

| | | | |
|---|---|---|---|
| 6,394,998 B1 | 5/2002 | Wallace et al. | |
| 6,488,689 B1 | 12/2002 | Kaplan et al. | |
| (Continued) | | | |

FOREIGN PATENT DOCUMENTS

RU 2640014 C1 12/2017

OTHER PUBLICATIONS

European Search Report for Application No. 19743917.7 dated Sep. 23, 2021.

*Primary Examiner* — Todd J Scherbel
(74) *Attorney, Agent, or Firm* — Gregory L. Mayback; Mayback IP Law, P.A.

(57) ABSTRACT

A recapturable external LAA exclusion clip system includes a clip comprising first and second clip struts, at least one of the struts having a connector interface comprising a first portion of a lock, and a delivery device comprising a handle and an end effector. The handle comprises jaw and lock controls. The end effector is connected to the handle and comprises a clevis and first and second jaws. The jaws are connected to the clevis and operatively connected to the jaw control to actively articulate at least one of the jaws with respect to the other. At least one of the jaws has a connector comprising a second portion of the lock operatively con-
(Continued)

nected to the lock control to removably lock with the first portion of the lock. The first and second portions of the lock have a locked state and are configured to unlock the locked state upon actuation of the lock control.

36 Claims, 35 Drawing Sheets

Related U.S. Application Data a continuation of application No. 16/865,010, filed on May 1, 2020, now Pat. No. 10,925,615, application No. 17/143,862 is a continuation of application No. 16/865,010, filed on May 1, 2020, now Pat. No. 10,925,615.

(60) Provisional application No. 62/843,069, filed on May 3, 2019.

(56) References Cited

U.S. PATENT DOCUMENTS

| | | | |
|---|---|---|---|
| 6,849,075 B2 | 2/2005 | Bertolero et al. |
| 7,226,448 B2 | 6/2007 | Bertolero et al. |
| 7,399,300 B2 | 7/2008 | Bertolero et al. |
| 7,542,807 B2 | 6/2009 | Bertolero et al. |
| 7,591,818 B2 | 9/2009 | Bertolero et al. |
| 7,749,157 B2 | 7/2010 | Bertolero |
| 7,819,867 B2 | 10/2010 | Bertolero et al. |
| 7,951,069 B2 | 5/2011 | Bertolero |
| 7,957,820 B2 | 6/2011 | Bertolero et al. |
| 3,096,990 A1 | 1/2012 | Swanson et al. |
| 8,096,990 B2 | 1/2012 | Swanson et al. |
| 8,419,729 B2 | 4/2013 | Ibrahim et al. |
| 8,454,593 B2 | 6/2013 | Bertolero et al. |
| 8,535,307 B2 | 9/2013 | Bertolero et al. |
| 8,545,498 B2 | 10/2013 | Bertolero et al. |
| 9,101,364 B2 | 8/2015 | Ibrahim et al. |
| 9,427,277 B2 | 8/2016 | Swanson et al. |
| 9,861,371 B2 | 1/2018 | Martin et al. |
| 9,888,925 B2 | 2/2018 | Bertolero et al. |
| 10,631,874 B2 | 4/2020 | Martin et al. |
| 10,925,615 B2 * | 2/2021 | Deville .............. A61B 17/1285 |
| 2005/0149069 A1 | 7/2005 | Bertolero et al. |
| 2005/0177182 A1 | 8/2005 | van der Burg et al. |
| 2005/0273129 A1 | 12/2005 | Michels et al. |
| 2006/0020271 A1 | 1/2006 | Stewart et al. |
| 2009/0012545 A1 | 1/2009 | Williamson, IV et al. |
| 2009/0209986 A1 * | 8/2009 | Stewart ................ A61B 17/122 606/157 |
| 2010/0204716 A1 | 8/2010 | Stewart et al. |
| 2011/0046641 A1 | 2/2011 | Kassab et al. |
| 2011/0230903 A1 | 9/2011 | Bertolero |
| 2012/0109161 A1 | 5/2012 | Privitera et al. |
| 2013/0131649 A1 | 5/2013 | Hughett, Sr. et al. |
| 2014/0012254 A1 | 1/2014 | Bertolero et al. |
| 2014/0039488 A1 | 2/2014 | Bertolero et al. |
| 2014/0188159 A1 | 7/2014 | Steege |
| 2014/0221993 A1 | 8/2014 | Bertolero et al. |
| 2019/0105104 A1 | 4/2019 | Bertolero et al. |
| 2020/0100789 A1 | 4/2020 | Bertolero et al. |
| 2020/0222056 A1 | 7/2020 | Martin et al. |

\* cited by examiner

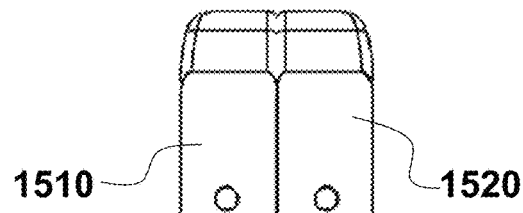
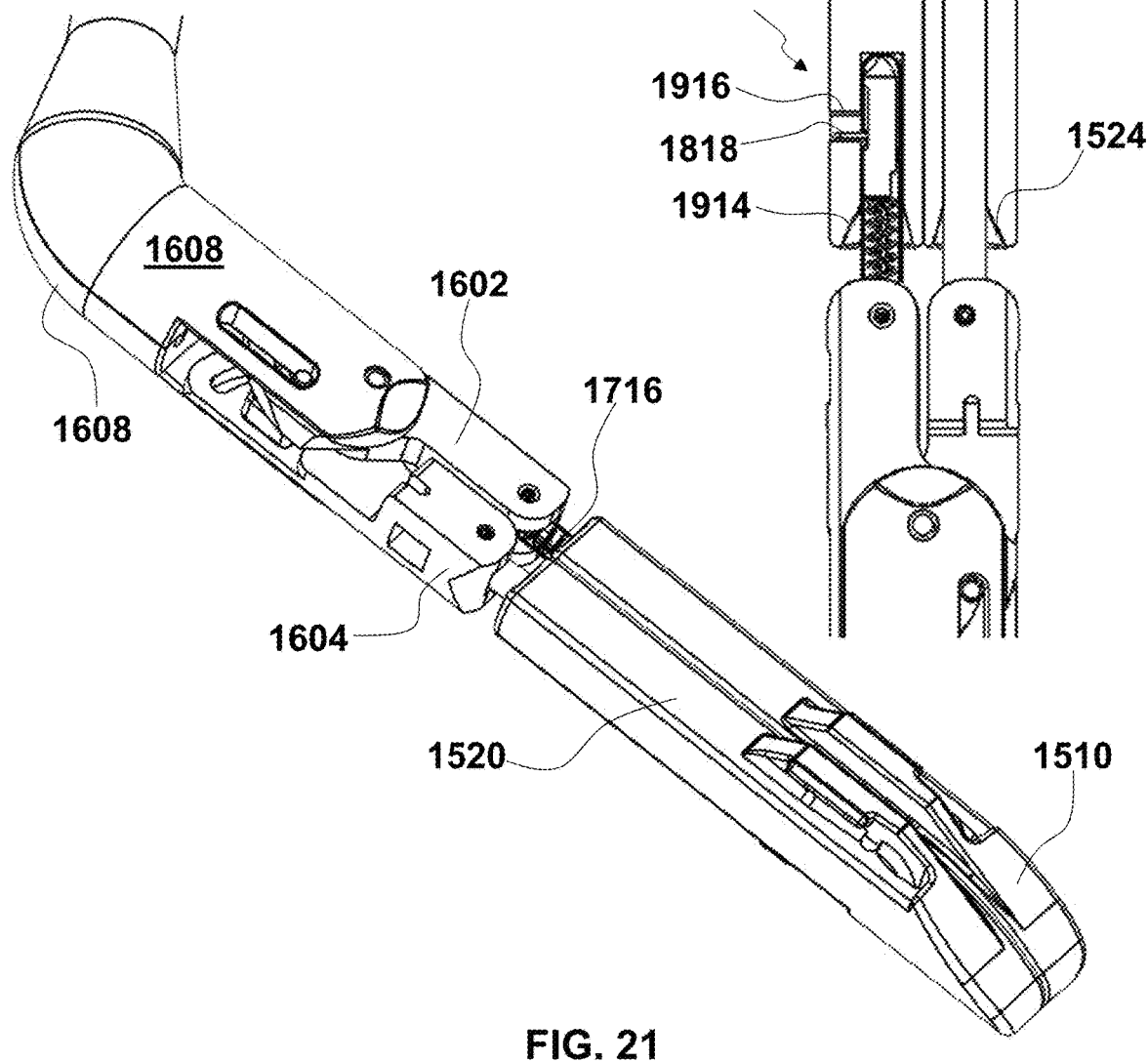
FIG. 20
FIG. 21

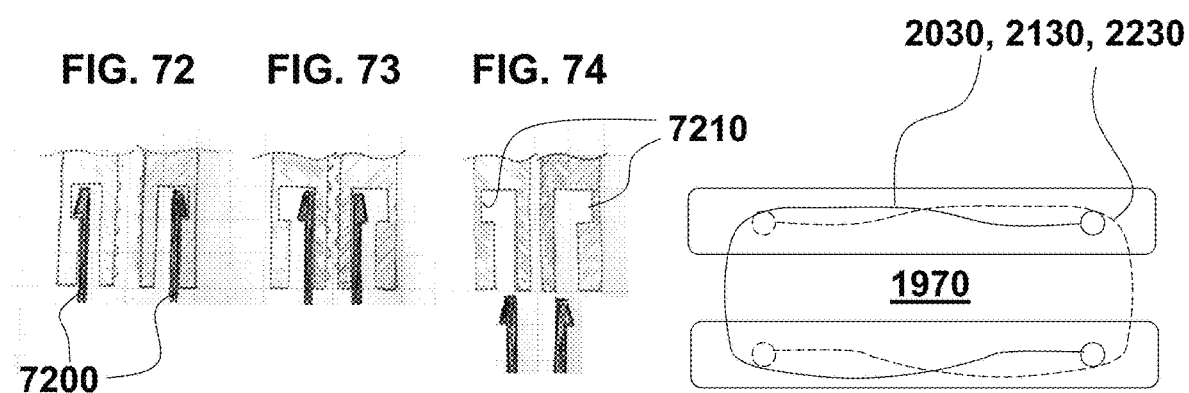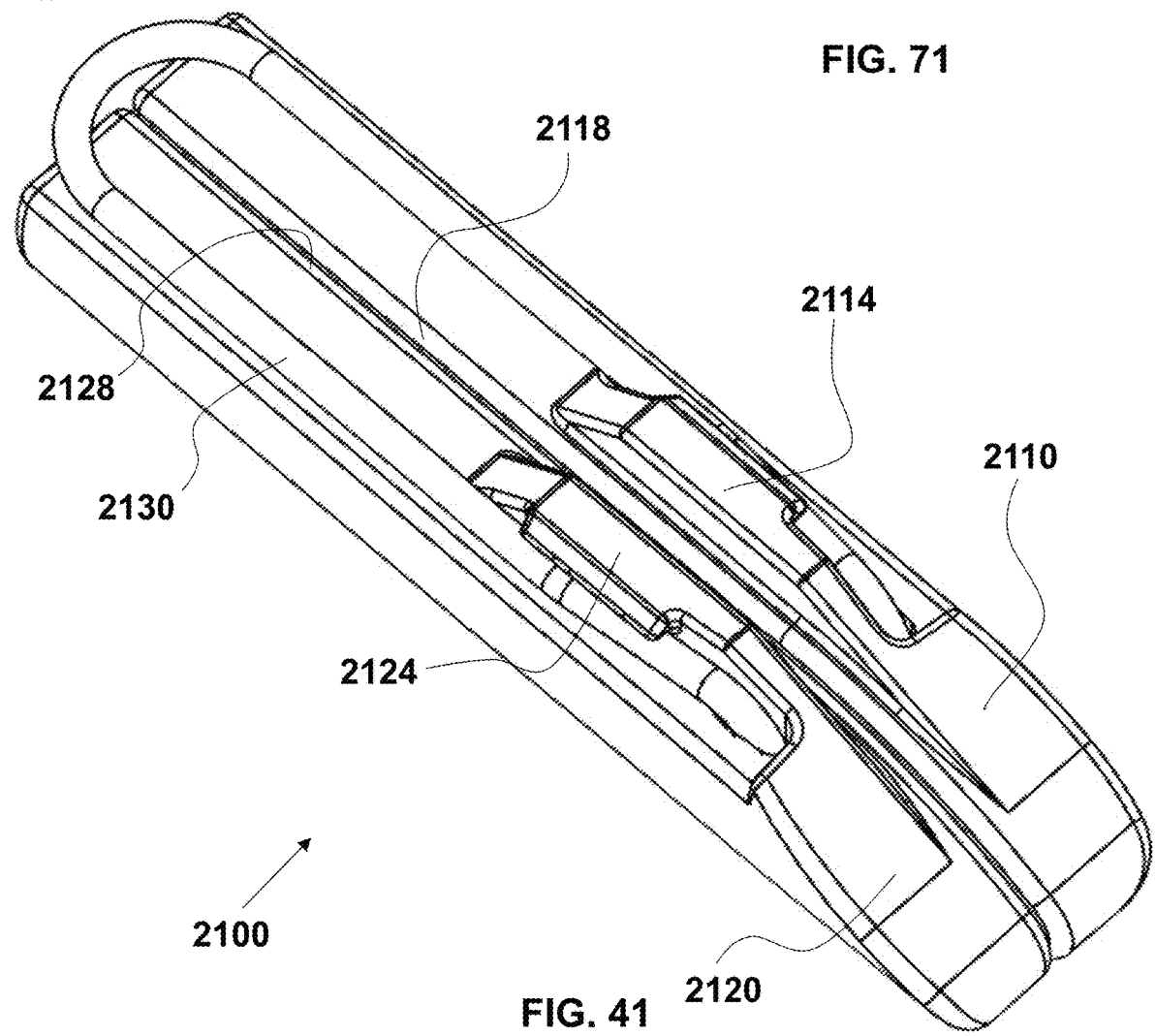

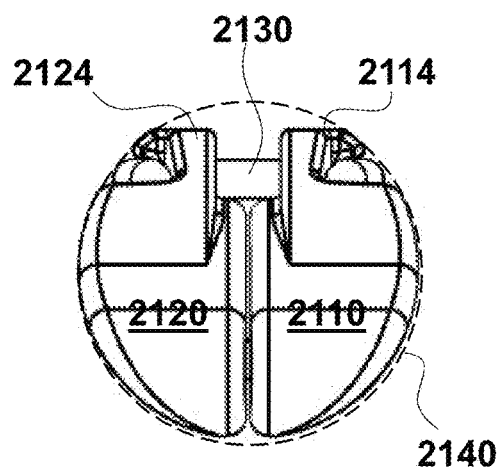
FIG. 46
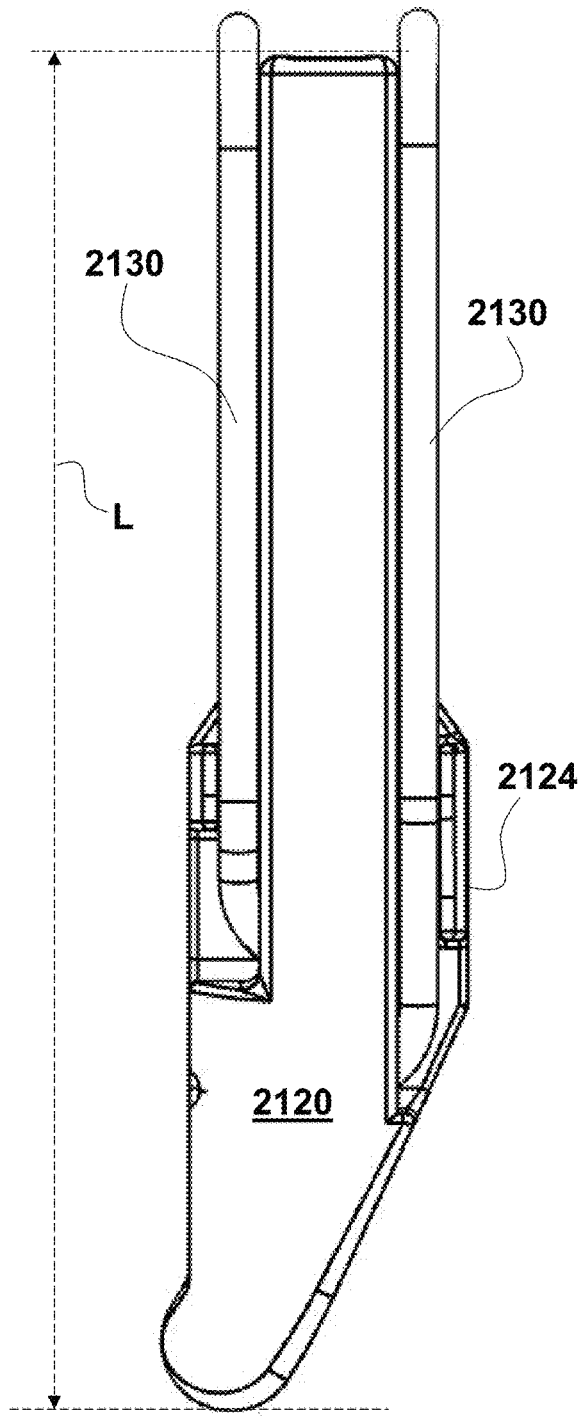
FIG. 47
FIG. 48

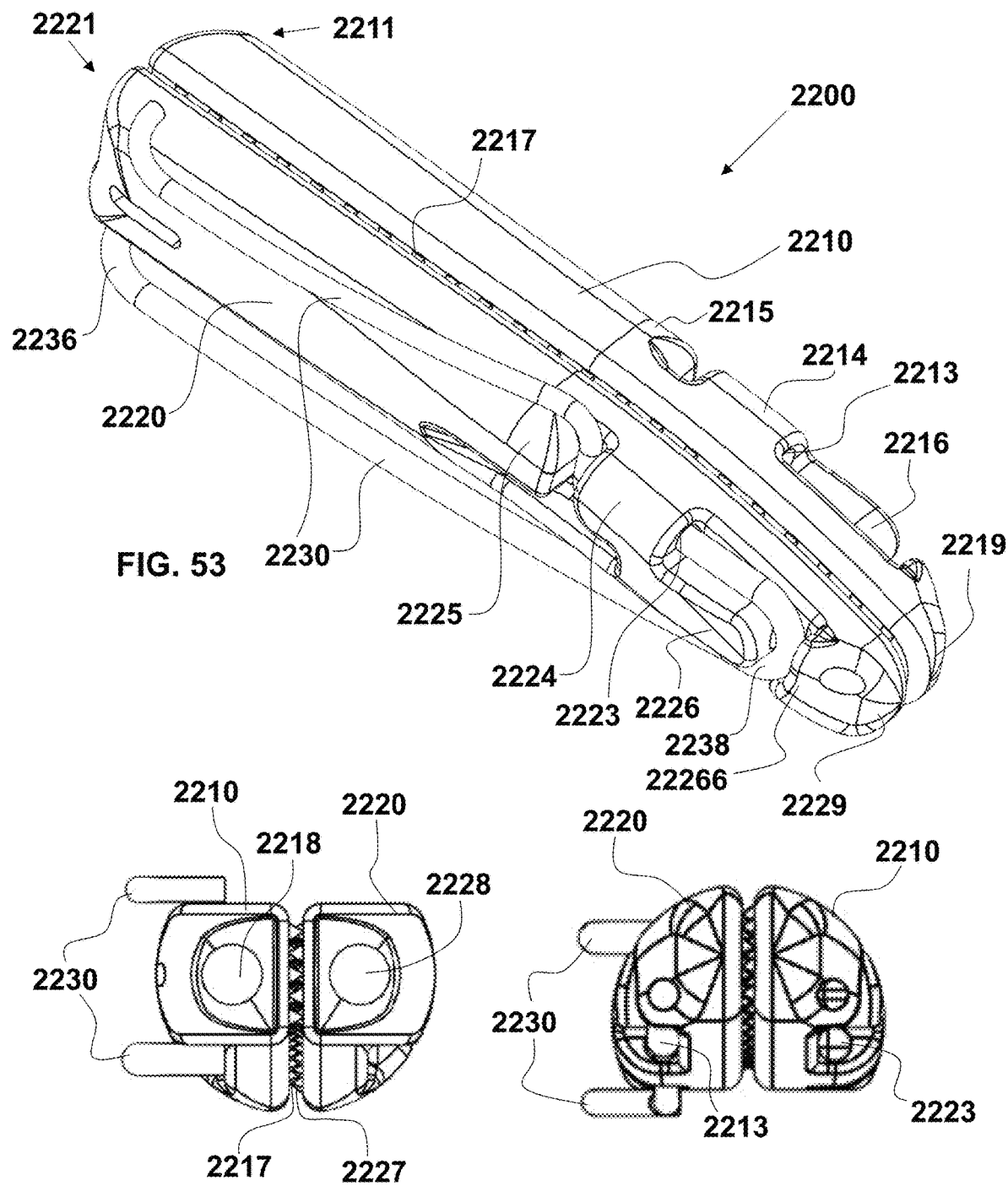

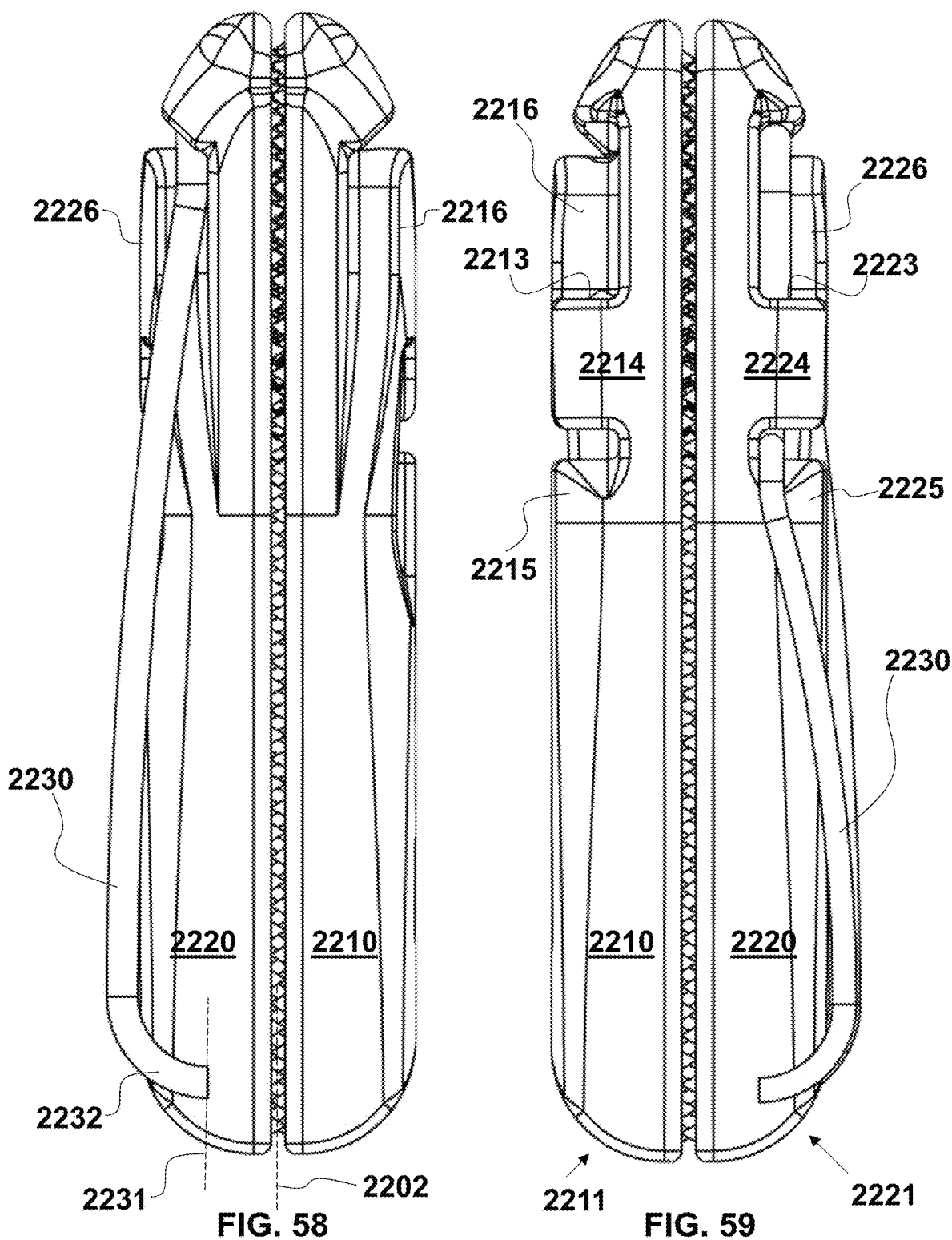

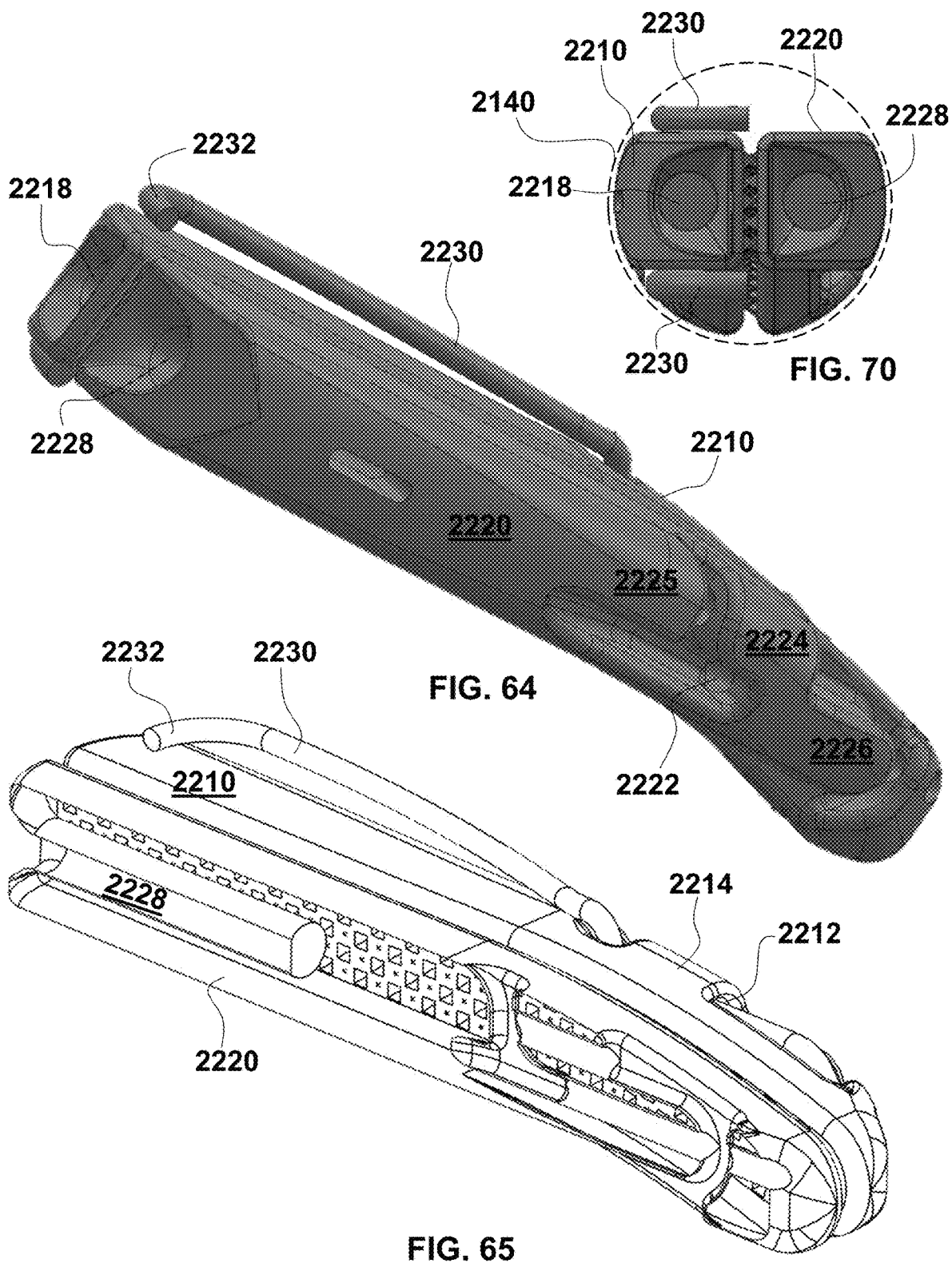

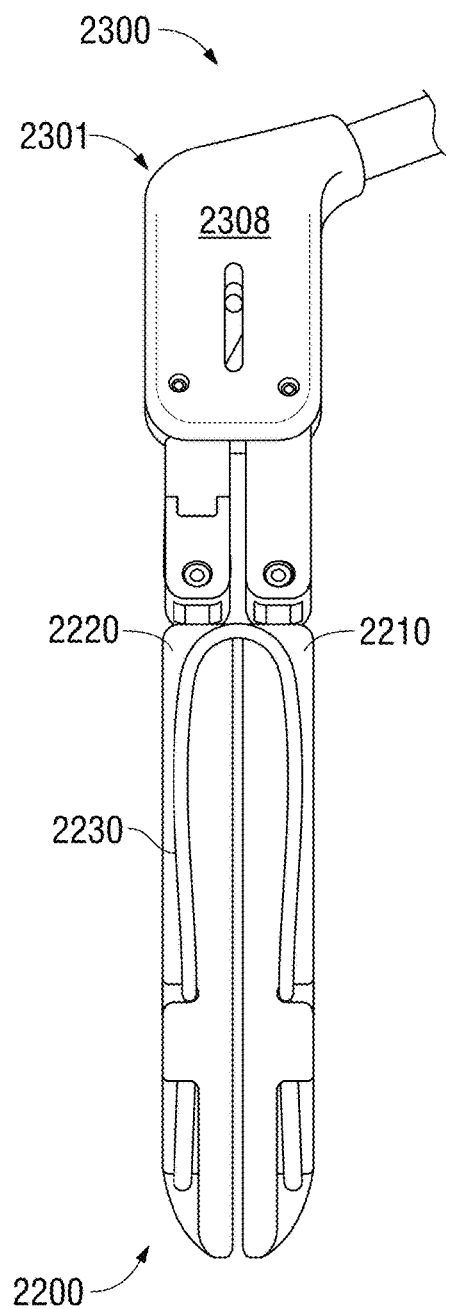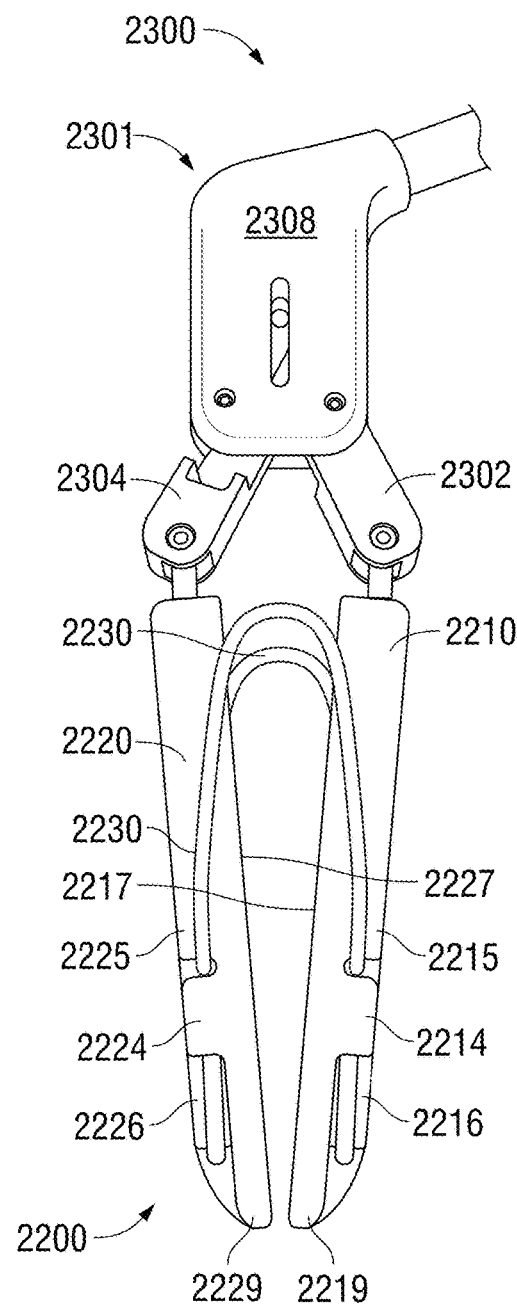
FIG. 66
FIG. 67

RECAPTURABLE LEFT ATRIAL APPENDAGE CLIPPING DEVICE AND METHODS FOR RECAPTURING A LEFT ATRIAL APPENDAGE CLIP

CROSS-REFERENCE TO RELATED APPLICATIONS

This application is:
a continuation application of U.S. patent application Ser. No. 16/865,010, filed May 1, 2020, of which priority is claimed under 35 U.S.C. § 120 (which application claims the priority, under 35 U.S.C. § 119, of U.S. Provisional Patent Application No. 62/843,069, filed May 3, 2019); and
continuing application, under 35 U.S.C. § 120, of copending international application No. PCT/US20/31228, filed May 3, 2020, which designated the United States and was published in English; this application also claims the priority, under 35 U.S.C. § 119, of U.S. patent application Ser. No. 16/865,010, filed May 1, 2020, of which priority is claimed under 35 U.S.C. § 120 (which application claims the priority, under 35 U.S.C. § 119, of U.S. Provisional Patent Application No. 62/843,069, filed May 3, 2019);
the entire disclosures of which are hereby incorporated herein by reference in their entireties.

STATEMENT REGARDING FEDERALLY SPONSORED RESEARCH OR DEVELOPMENT

Not applicable.

FIELD OF THE INVENTION

The present systems, apparatuses, and methods lie generally in the field of surgical approaches to externally occluding the fluid passageway of a hollow tissue structure. Specifically, the present disclosure relates to devices, systems, and methods that externally clip the left atrial appendage ("LAA") of the heart to exclude the LAA from the left atrium of the heart, to effectively close off the fluid passageway between the LAA and the left atrium, and to recapture the clip after having been implanted.

BACKGROUND OF THE INVENTION

Presently, in the United States, the most common type of cardiac arrhythmia is atrial fibrillation (AF), which is characterized as the chaotic and rapid electrical activity of the upper chambers of the heart. There are several causes and risk factors leading to the development of atrial fibrillation, including hypertension, acute and chronic rheumatic heart disease, and hyperthyroidism. Because of this abnormal heart rhythm, contraction of the atrial fibers is asynchronous (not in harmony or unison), such that atrial pumping could cease altogether. Therefore, one of the most dangerous conditions occurring during atrial fibrillation is the disruption or stasis of the blood flow in the atria, which can lead to thrombus (blood clot) formation, placing the afflicted person at a high risk of a heart attack or an embolic stroke. The great majority of blood clots resulting from atrial fibrillation originate in the LAA, due to the LAA's anatomical position and physiological characteristics. The LAA is a pedunculated and finger-shaped, sack-like cavity connected to the lateral wall of the left atrium between the mitral valve and the root of the left pulmonary vein. Thus, the LAA is a prime location for the detrimental pooling and accumulation of stagnant blood when the heart is not contracting to squeeze blood into the ventricles at a normal and coordinated pace. As a result, clots can easily form and accumulate in the LAA, build upon themselves, and propagate out from the LAA and into the atrium. Accordingly, because the LAA is predisposed for thrombus formation, the containment or elimination of clots formed in the LAA of atrial fibrillation patients would greatly reduce the incidence of stroke in those patients.

Pharmacological therapies, such as blood thinners, anticoagulants, and antiplatelet medications are well-known and routinely used to reduce the risk of blood clot formation. However, these medications are associated oftentimes with both harmful and distressing side effects and complications, including excessive bleeding, headaches, dizziness, fatigue, and contraindications, making patient compliance and tolerance very difficult. Thus, there is a compelling interest in developing alternatives that increase efficacy, limit any dangerous and chronic side effects, and improve a patient's quality of life.

Accordingly, another approach to reducing or entirely eliminating the risk of clot formation in the LAA is through an open chest, thoracotomy, thoracoscopy, or percutaneous surgical intervention that effectively shuts off or substantially restricts blood flow between the LAA and left atrium. The exact role of the LAA as a part of the cardiovascular system is not entirely clear. It is thought that the LAA is perhaps suited to act as a kind of decompression chamber during left ventricle systole and during other periods when left atrial pressure is high. However, it does not appear that the LAA performs a necessary function and is considered physiologically insignificant to the anatomy and function of the heart. Therefore, surgically cutting off fluid communication to the LAA, or obliterating (i.e., removing) the LAA from the heart entirely, are promising and feasible approaches to drastically reducing the risk of clot formation in the LAA.

Each of the existing surgical approaches has its associated benefits and disadvantages. For example, the complete removal of the LAA eliminates all danger of future clot formation therein. However, there remains the risk of, during the procedure, dislodging and releasing an already-existing blood clot into the bloodstream. In addition, removal of the LAA creates a substantial wound on the heart that must be carefully controlled, expertly clamped, and sutured shut with absolute precision to avoid significant bleeding. Furthermore, removal of the LAA is clearly a dramatic anatomical change and, therefore, should be considered with caution as the hemodynamic and hormonal roles of the LAA are still a subject of ongoing study and understanding.

Other surgical approaches aim to seal or block off, or occlude, the fluid passageway between the LAA and the left atrium without removing any of the anatomy. For example, a surgeon may surgically stitch or staple the LAA (e.g., via direct intra-atrial suture or external ligation) to effectively close the passageway, thereby reducing the LAA to just a blind pouch isolated from the left atrium. In a further example, a biocompatible barrier device may be implanted from within the left atrium at the entrance to the LAA and anchored within the passageway using a percutaneous delivery device (such as a vascular catheter). An example of such a device is the WATCHMAN™ Left Atrial Appendage Closure Device sold by Boston Scientific Corporation. Although some of these procedures can be conducted using minimally invasive techniques (e.g., thoracotomy, thoracoscopy), there remains considerable risk because the heart tissue is either pierced or an intrusion is made into the heart's interior. Furthermore, the effectiveness of these procedures depends upon the exact placement of the staples, sutures, implant, or other occlusion device, thus requiring the surgeon's ultraprecision. In addition, any foreign device left in the chamber of the heart has the future potential of being a thrombosis-generating site as some biocompatible materials could eventually break down and/or promote clot formation. Accordingly, there is a great desire for developing different surgical approaches for occluding or isolating the LAA that do not require an actual breach of the heart tissue.

One example of such a procedure is the permanent surgical application of an exclusion clip to the exterior surface of the LAA. Specifically, an exclusion clip is positioned about and around the base of the LAA to apply a sufficient pinching or clamping pressure that effectively closes the interior fluid passageway between the LAA and the atrium, without ever penetrating the heart. Therefore, the potential for uncontrolled bleeding or other trauma occurring to the heart is drastically reduced. Also, because no element of the exclusion clip is introduced into the cardiovascular system, there is minimal risk of inadvertently creating a site that promotes formation of clots in the future. Still yet, there are several inherent limitations in the existing exclusion clip designs and in the systems, procedures, and delivery devices presently used for applying the exclusion clips.

By way of background, the currently existing exclusion clips employed to isolate the LAA are generally formed from a pair of elongated and opposing clamping members urged together by one or more spring members. Prior to application of the exclusion clip to the LAA, a delivery device engages the exclusion clip and imparts a force counteracting the spring-biased closing force of the spring member or members in order to separate the clamping members from each other and create an interior space therebetween. During application, the LAA is positioned within the interior space of the exclusion clip to be received between the opposing clamping members. Once the surgeon determines that the exclusion clip is in a desirable position with respect to the LAA, the clip's delivery device relieves the counteracting force imparted to the spring member or members and then disengages from the exclusion clip. As a result, the clamping members return to their inwardly spring-biased state to snugly surround the LAA in a grip-like manner and produce a clamping action against the exterior surface of the LAA. An example of such a device is the ATRICLIP® Left Atrial Appendage Exclusion System that is sold by AtriCure, Inc.

Presently, exclusion clips are designed to be either open-ended or closed-loop. The closed-loop exclusion clips are generally comprised of a pair of parallel and opposing clamping members connected on both ends by spring members to form a loop. By contrast, open-ended exclusion clips include a pair of opposing clamping members connected to one another at just a single end by a spring or spring-biased hinge-like member that urges the clamping members to pivot towards one another to generate the necessary clamping action.

Accordingly, to ensure the effectiveness and safety of the exclusion clip approach to isolating the LAA, the exclusion clip must be positioned accurately with respect to the LAA and the remainder of the heart, and with sufficient pressure, to adequately and permanently close off the blood flow into and out from the LAA, while at the same time not severing or otherwise damaging the LAA or any other surrounding structure. Therefore, the surgeon must skillfully control the placement of the exclusion clip and determine that the clip is sufficiently closed and securely in place, which is not an insignificant feat. Once the exclusion clip seats on the LAA, the interposed tissue will desiccate and otherwise shrink and change, thereby requiring a different and greater amount of clamping force to keep the LAA sealed properly.

A further limitation of existing exclusion clip designs (in particular, the closed-loop design) is that the distance of the interior opening between the opposing clamping members is restricted by the spring-biasing force imposed by the spring member or members, wherein the spring-biasing force is dependent upon the degree to which the spring member or members are able to flex. As a result, a surgeon might struggle to apply the exclusion clip when a patient's LAA is of a relatively large size.

Open-ended LAA exclusion clips are sometimes preferred over closed-ended clips because they only require lateral access to the LAA and, therefore, can be positioned when there is limited access to the heart and with less-invasive procedures. A drawback of open-ended clips, however, is that it is often difficult for the surgeon to determine when the clip has been positioned completely across the entire width of the LAA. Because a lateral approach is used to place the clip, the far end of the LAA is usually not visible to the surgeon. This requires the surgeon to estimate the position of the distal end of the clip and release the clip when the surgeon believes that the clip spans entirely across the LAA. If the surgeon's estimation is incorrect and an open-ended clip is positioned only partially across the LAA when it is released into the clamped configuration, only partial exclusion of the LAA is achieved. Such an implantation will likely lead to complications, requiring further surgery to correct the partial exclusion.

There is, therefore, a need in the art for an applicator device for open-ended LAA exclusion clips that provides the surgeon with a positive indication that the clip has been positioned completely across the LAA before it is released into the clamped implanted configuration.

Further, as described above, the LAA must be suitably oriented and held in a stable position to bring the LAA into the interior space of the exclusion clip during its application. Accordingly, an instrument separate from the clip delivery device, such as a surgical grasper, is typically used to manipulate the LAA into position. In fact, in all occlusion, exclusion, and obliteration procedures of the LAA, it is necessary to use a separate instrument solely dedicated to orienting the LAA into the correct position. As a result, in an exclusion clip procedure, the surgeon must simultaneously operate the clip delivery device and the stabilization instrument (or directly stabilize the heart), thereby occupying both of the surgeon's hands. This limits the surgeon's mobility and freedom, which can also lead to fatigue. Importantly, if not performed carefully, just a slight misstep in the simple manipulation of the LAA may tear or perforate the LAA, potentially causing an immediate danger of life-threatening hemorrhaging. Therefore, there is a need in the art for an exclusion clip and delivery device system that simplifies and improves the precision of the interaction between the exclusion clip and the LAA, and minimizes or eliminates the need for and/or involvement of a separate grasping or nudging device with the LAA.

Additionally, there is a need in the art for an exclusion clip whose shape, material characteristics, tolerances, and surface area features improve the surface-to-surface interaction between the clip's clamping members and both the LAA and the left atrium once the clip is in place, as well as strengthen the grip of the exclusion clip about the LAA without causing any damage to the tissue, not only during the surgical procedure, but also over the lifetime of the implanted clip.

During an implantation of the exclusion clip, it is possible that the surgeon has implanted the clip thinking that the clip is in a desirable position, but after having released the exclusion clip from the delivery device, the surgeon believes that the clip should be removed and re-implanted. There is a need in the art to have a delivery device that can engage and recapture the exclusion clip after having been implanted on the LAA and open the exclusion clip for re-implantation in the more desirable position.

Thus, a need exists to overcome the problems with the prior art systems, designs, and processes as discussed above.

SUMMARY OF THE INVENTION

The systems, apparatuses, and methods that are described provide devices, systems, and methods that clip the exterior surface of the left atrial appendage to fluidically disconnect the interior of the LAA from the left atrium that overcome the hereinafore-mentioned disadvantages of the heretofore-known devices and methods of this general type. More specifically, the systems, apparatuses, and methods described provide a delivery device for an LAA exclusion clip having structural features that, during the surgical application of the exclusion clip, act in such a way to permit recapture of the LAA exclusion clip and either re-implantation or removal. Such a delivery device beneficially minimizes or obviates the need for a stabilization instrument separate from the delivery device for manipulating the LAA with respect to the exclusion clip, resulting in a one-handed and no-touch procedure.

The systems, apparatuses, and methods described further provide a closed-loop exclusion clip that gives the surgeon greater precision and control over the degree of clamping pressure that is applied and is free of the conventional restrictions resulting from employing spring members to connect the terminating ends of the clip's opposing clamping members.

In one embodiment, the delivery device comprises a shaft having a proximal end and a distal end, a handle housing one or more controls connected to the proximal end of the shaft, and an applicator head connected to the distal end of the shaft. The applicator head comprises two opposing jaws adapted to receive an open ended exclusion clip. The jaws pivot between a closed and an open position by a pivot assembly located at or near the proximal end of the applicator head attached to the shaft. The pivoting action of the jaws is controlled by one or more of the controls on the handle. At the tip of each of the jaws there is a holding member, for example, an internal connector.

The delivery device can be used with exclusion clips having a number of different designs, whether known in the art or indicated herein. In an embodiment of an open-end exclusion clip, the clip is placed on the two opposing jaws with the open end of the clip facing distally in the direction of the tips of the jaws. Each of the parallel clamping members of the exclusion clip is fastened releasably to the respective jaw. In this fashion, when control on the device's handle is actuated to separate the opposing jaws, the exclusion clip is forced open. When control is actuated to permit the opposing jaws to close, the spring(s) in the exclusion clip urges the jaws to close.

The exclusion clip can be fastened releasably to the jaws in a number of different ways. Various exemplary embodiments utilize locks that removably secure within internal spaces of the struts of the exclusion clip. When an operator is satisfied that the exclusion clip is correctly positioned, a release is actuated (e.g., a cable is pulled) and the exclusion clip can be removed from the applicator clevis or head, thus releasing the exclusion clip from the delivery device.

In operation, the surgeon commences application of the exclusion clip by opening the jaws and exclusion clip by actuating an appropriate control on the handle. In an open-end embodiment of the exclusion clip, the open end is then positioned across the LAA using a lateral approach. When the surgeon believes the clip is inserted sufficiently to completely span the LAA when closed, the handle control is actuated to permit the clip to close, clamping the LAA. If the surgeon correctly estimated the insertion distance of the clip, the tips of the opposing jaws will come into very close proximity to each other with no structures (such as the LAA) between them. The surgeon can then reopen the clip and attempt to correctly position the clip until the desirable implantation position is achieved. The surgeon thereafter actuates a release and the exclusion clip is released from the jaws of the delivery device. Removal of the delivery device completes implantation. The delivery device can re-engage the exclusion clip if the surgeon desires.

With the foregoing and other objects in view, there is provided, a recapturable external left atrial appendage (LAA) exclusion clip system comprises an LAA exclusion clip and a delivery device. The exclusion clip comprises a first clip strut and a second clip strut, at least one of the first and second clip struts having a connector interface comprising a first portion of a lock. The delivery device comprises a handle comprising a jaw control and a lock control, an end effector connected to the handle and comprising a clevis and first and second jaws connected to the clevis, and operatively connected to the jaw control to actively articulate at least one of the first and second jaws with respect to the other, at least one of the first and second jaws having a connector comprising a second portion of the lock operatively connected to the lock control to removably lock with the first portion of the lock. The first and second portions of the lock have a locked state and are configured to unlock the locked state upon actuation of the lock control.

With the objects in view, there is also provided a recapturable external LAA exclusion clip system comprises an LAA exclusion clip and a delivery device. The LAA exclusion clip comprises a first clip strut and a second clip strut, at least one of the first and second clip struts having an internal connector interface comprising a first portion of a lock. The delivery device comprises a handle comprising a jaw control and a lock control, an end effector connected to the handle and comprising a clevis and first and second jaws connected to the clevis and operatively connected to the jaw control to actively articulate at least one of the first and second jaws with respect to the other, at least one of the first and second jaws having a connector comprising a second portion of the lock operatively connected to the lock control to removably lock with the first portion of the lock. The first and second portions of the lock have a locked state and are configured to unlock the locked state upon actuation of the lock control and to automatically enter the locked state as the first and second portions of the lock are moved together.

With the objects in view, there is also provided a recapturable external LAA exclusion clip system comprises an LAA exclusion clip and a delivery device. The exclusion clip comprises a first clip strut having a first tissue-contacting surface, a second clip strut having a second tissue-contacting surface opposing the first tissue-contacting surface, the first and second clip struts shaped to fit on opposing sides of a LAA, each of the first and second clip struts having an internal connector interface, and at least one of the first and second clip struts comprising a first portion of a lock, and a bias device movably connecting the first and second clip struts together. The delivery device comprises a handle comprising a hollow shaft defining a lumen, a lock controller having a clip lock cord passing through the lumen, and a jaw trigger having an end effector cord passing through the lumen. The end effector is attached to the shaft and comprises a clevis and first and second internal connectors operatively connected to the end effector cord to pivot the first and second internal connectors with respect to the clevis, at least one of the first and second internal connectors having a second portion of the lock operatively connected to the clip lock cord and shaped to removably lock with the first portion of the lock, and having different lengths and each pivotally connected to the clevis such that, while a longer one of the first and second internal connectors is at least partially inserted within the one of the first and second internal connector interfaces, motion of the handle allows a user to passively align a shorter one of the first and second internal connectors into the other one of the first and second internal connector interfaces. The first and second portions of the lock have a locked state and are configured to unlock upon actuation of the lock controller when locked together and to automatically enter the locked state without actuation of the lock controller as the first and second portions of the lock are moved together.

In accordance with another feature, the connector interface comprises a first internal connector interface and a second internal connector interface, the first clip strut comprises a first proximal end defining the first internal connector interface, the second clip strut comprises a second proximal end defining the second internal connector interface, the connector comprises a first internal connector shaped to connect within the first internal connector interface and a second internal connector shaped to connect within the second internal connector interface, the first jaw comprises the first internal connector, the second jaw comprises the second internal connector, and one of the first and second internal connectors is longer than the other one of the first and second internal connectors.

In accordance with a further feature, the first internal connector is shaped to connect within either of the first and second internal connector interfaces and the second internal connector is shaped to connect within either of the first and the second internal connector interfaces.

In accordance with an added feature, the at least one of the first and second clip struts has a proximal end defining the connector interface as a hole comprising a lock orifice as the first portion of the lock.

In accordance with an additional feature, the first clip strut comprises a first proximal end defining a first internal connector interface as a hole, the first portion of the lock being connected to the hole, or the second clip strut comprises a second proximal end defining a second internal connector interface as a hole, the first portion of the lock being connected to the hole.

In accordance with yet another feature, the first clip strut comprises a first proximal end defining a first internal connector interface as a first hole, the first portion of the lock being connected to the first hole, the second clip strut comprises a second proximal end defining a second internal connector interface as a second hole, the first portion of the lock being connected to the second hole, the first jaw comprises the connector as a first internal connector comprising the second portion of the lock and shaped to connect within the first internal connector interface, and the second jaw comprises the connector as a second internal connector comprising the second portion of the lock and shaped to connect within the second internal connector interface.

In accordance with yet a further feature, the first and second internal connectors have different lengths and are each pivotally connected to the clevis such that, while a longer one of the first and second internal connectors is at least partially inserted within one of the first and second internal connector interfaces, motion of the handle allows a user to passively align a shorter one of the first and second internal connectors into the other one of the first and second internal connector interfaces.

In accordance with yet an added feature, the second portion of the lock of each of the first and second internal connectors is operatively connected to the lock control and configured to unlock with the respective first portion of the lock when the lock control is actuated.

In accordance with yet an additional feature, the connector interface is an internal connector interface, the connector is an internal connector comprising the second portion of the lock, at least one of the first and second clip struts comprises a proximal end defining the internal connector interface as a hole, the first portion of the lock being connected to the hole, and at least one of the first and second jaws comprises the internal connector and is shaped to connect within the internal connector interface.

In accordance with again another feature, the first and second jaws are each pivotally connected to the clevis, the first jaw is operatively connected to the jaw control to actively articulate with respect to the clevis, and the second jaw is operatively connected to the jaw control to actively articulate with respect to the clevis.

In accordance with again a further feature, a first actuation direction of the jaw control causes the first and second jaws to separate from one another and a second actuation direction of the jaw control causes the first and second jaws to move towards one another.

In accordance with again an added feature, the second portion of the lock is shaped to removably lock with the first portion of the lock.

In accordance with again an additional feature, the first and second portions of the lock are configured to automatically enter the locked state as the first and second portions of the lock are moved together.

In accordance with still another feature, there is provided a shaft connecting the end effector to the handle and the jaw control comprises a jaw control cord connected to the at least one of the first and second jaws, and the lock control comprises at least one lock release cord connected to the second portion of the lock.

In accordance with still a further feature, the first clip strut has a first tissue-contacting surface, the second clip strut has a second tissue-contacting surface opposing the first tissue-contacting surface, and actuation of the jaw control moves the first tissue-contacting surface and the second tissue-contacting surface selectively towards or away from one another in a strut plane.

In accordance with still an added feature, the at least one of the first and second clip struts has a proximal end, the connector interface extends from the proximal end into the at least one of the first and second clip struts and comprises a lock orifice as the first portion of the lock, and the connector comprises a cord lock as the second portion of the lock, the cord lock being configured to secure removably to the lock orifice.

In accordance with still an additional feature, an entirety of the LAA exclusion clip defines a transverse cross-sectional circle having a given outer diameter equal to or less than 10 mm, and the end effector defines a laterally cross-sectional circle having an outer diameter no greater than the given outer diameter.

In accordance with still another feature, at least one of the first clip strut comprises a first proximal end defining the internal connector interface as a hole comprising the first portion of the lock and the second clip strut comprises a second proximal end defining the internal connector interface as a hole comprising the first portion of the lock, at least one of the first jaw comprises the connector as an internal connector comprising the second portion of the lock and is shaped to connect within the internal connector interface and the second jaw comprises the connector as an internal connector comprising the second portion of the lock and is shaped to connect within the internal connector interface.

In accordance with yet another feature, the first clip strut comprises a first proximal end defining a first internal connector interface as a hole comprising the first portion of the lock, the second clip strut comprises a second proximal end defining a second internal connector interface as a hole comprising the first portion of the lock, the first jaw comprises the connector as a first internal connector comprising the second portion of the lock and is shaped to connect within the first internal connector interface, and the second jaw comprises the connector as a second internal connector comprising the second portion of the lock and is shaped to connect within the second internal connector interface, and the first and second internal connectors have different lengths and are each pivotally connected to the clevis such that, while a longer one of the first and second internal connectors is at least partially inserted within the one of the first and second internal connector interfaces, motion of the handle allows a user to passively align a shorter one of the first and second internal connectors into the other one of the first and second internal connector interfaces.

In accordance with a concomitant feature, each of the first and second internal connector interfaces comprise the first portion of the lock and each of the first and second internal connectors comprise the second portion of the lock to which the respective first portion of the lock secures removably.

Although the systems, apparatuses, and methods are illustrated and described herein as embodied in devices, systems, and methods that externally clip the LAA to exclude the LAA from the left atrium of the heart, to effectively close off the fluid passageway between the LAA and the left atrium, and to recapture the clip after having been implanted, it is, nevertheless, not intended to be limited to the details shown because various modifications and structural changes may be made therein without departing from the spirit of the invention and within the scope and range of equivalents of the claims. Additionally, well-known elements of exemplary embodiments will not be described in detail or will be omitted so as not to obscure the relevant details of the systems, apparatuses, and methods.

Additional advantages and other features characteristic of the systems, apparatuses, and methods will be set forth in the detailed description that follows and may be apparent from the detailed description or may be learned by practice of exemplary embodiments. Still other advantages of the systems, apparatuses, and methods may be realized by any of the instrumentalities, methods, or combinations particularly pointed out in the claims.

Other features that are considered as characteristic for the systems, apparatuses, and methods are set forth in the appended claims. As required, detailed embodiments of the systems, apparatuses, and methods are disclosed herein; however, it is to be understood that the disclosed embodiments are merely exemplary of the systems, apparatuses, and methods, which can be embodied in various forms. Therefore, specific structural and functional details disclosed herein are not to be interpreted as limiting, but merely as a basis for the claims and as a representative basis for teaching one of ordinary skill in the art to variously employ the systems, apparatuses, and methods in virtually any appropriately detailed structure. Further, the terms and phrases used herein are not intended to be limiting; but rather, to provide an understandable description of the systems, apparatuses, and methods. While the specification concludes with claims defining the systems, apparatuses, and methods of the invention that are regarded as novel, it is believed that the systems, apparatuses, and methods will be better understood from a consideration of the following description in conjunction with the drawing figures, in which like reference numerals are carried forward.

BRIEF DESCRIPTION OF THE DRAWINGS

The accompanying figures, where like reference numerals refer to identical or functionally similar elements throughout the separate views, which are not true to scale, and which, together with the detailed description below, are incorporated in and form part of the specification, serve to illustrate further various embodiments and to explain various principles and advantages all in accordance with the systems, apparatuses, and methods. Advantages of embodiments of the systems, apparatuses, and methods will be apparent from the following detailed description of the exemplary embodiments thereof, which description should be considered in conjunction with the accompanying drawings in which:

FIG. 20 is a fragmentary, cross-sectional view of the end effector and occlusion clip of FIG. 18 with the occlusion clip removably installed on the jaws;

FIG. 21 is a fragmentary, perspective view of the end effector and occlusion clip of FIG. 20;

FIG. 41 is a perspective view from above an exemplary embodiment of another left atrial appendage surgical implant clip in a closed or steady-state orientation;

FIG. 46 is an elevational view of a distal end of the clip of FIG. 41;

FIG. 47 is an elevational view of a proximal end of the clip of FIG. 41;

FIG. 48 is a side elevational view of an outer side of the clip of FIG. 41;

FIG. 53 is a perspective view of an exemplary embodiment of another left atrial appendage surgical implant clip in a closed or steady-state orientation with a cross-section of the upper and lower bias devices through a centerline of the upper and lower bias devices showing a side adjacent a second clip strut and with the upper and lower bias devices diagrammatically biased outward away from the second clip strut;

FIG. 54 is an elevational view of a distal end of the clip of FIG. 53 with a cross-section of the upper and lower bias devices through a centerline of the upper and lower bias devices showing a side adjacent a first clip strut and with the upper and lower bias devices diagrammatically biased outward away from the first clip strut;

FIG. 55 is an elevational view of a proximal end of the clip of FIG. 53 with a cross-section of the upper and lower bias devices through a centerline of the upper and lower bias devices showing a side adjacent the second clip strut and with the upper and lower bias devices diagrammatically biased outward away from the second clip strut;

FIG. 58 is a bottom plan view of the clip of FIG. 53;

FIG. 59 is a top plan view of the clip of FIG. 53;

FIG. 64 is a perspective view from above an outer side of a proximal end of the second clip strut of FIG. 53 with a cross-section of the upper and lower bias devices through a centerline of the upper and lower bias devices showing a side adjacent the first clip strut and with the upper and lower bias devices diagrammatically biased outward away from the first clip strut;

FIG. 65 is a perspective view from above an outer side of a distal end of the second clip strut of FIG. 53 with a longitudinally vertical and hollow cross-section of the second clip strut with a cross-section of the upper and lower bias devices through a centerline of the upper and lower bias devices showing a side adjacent the first clip strut and with the upper and lower bias devices diagrammatically biased outward away from the first clip strut;

FIG. 66 is a fragmentary, perspective view from above the clip of FIG. 53 and above an exemplary embodiment of a distal end of a delivery device that opens and closes clip-contacting ends removably attached to a proximal end of the clip in a clip-fully-closed orientation ready to be implanted;

FIG. 67 is a perspective view of the clip and delivery device of FIG. 66 in a first intermediate clip-open orientation with the proximal ends of the clip separated from one another;

FIG. 70 is an elevational view of a proximal end of the clip of FIG. 53 with a longitudinally vertical cross-section of the upper and lower bias devices through a centerline of the upper and lower bias devices showing a side adjacent the first clip strut;

FIG. 71 is a diagrammatic, plan view of exemplary embodiments of alternative configurations for the upper and lower bias devices of the clips of FIGS. 2, 12, 18, 34, 39, 41, 53, and 66;

FIG. 72 is a diagrammatic, cross-sectional view of an exemplary embodiment of locking configuration between a delivery device and an LAA exclusion clip with the delivery device in a locked state of the clip;

FIG. 73 is a diagrammatic, cross-sectional view of the configuration of FIG. 72 with the delivery device in an unlocked state of the clip before the clip is removed from the delivery device;

FIG. 74 is a diagrammatic, cross-sectional view of the configuration of FIG. 72 with the delivery device in an unlocked state of the clip after the clip is removed from the delivery device

DETAILED DESCRIPTION OF THE EMBODIMENTS

Figure 1:
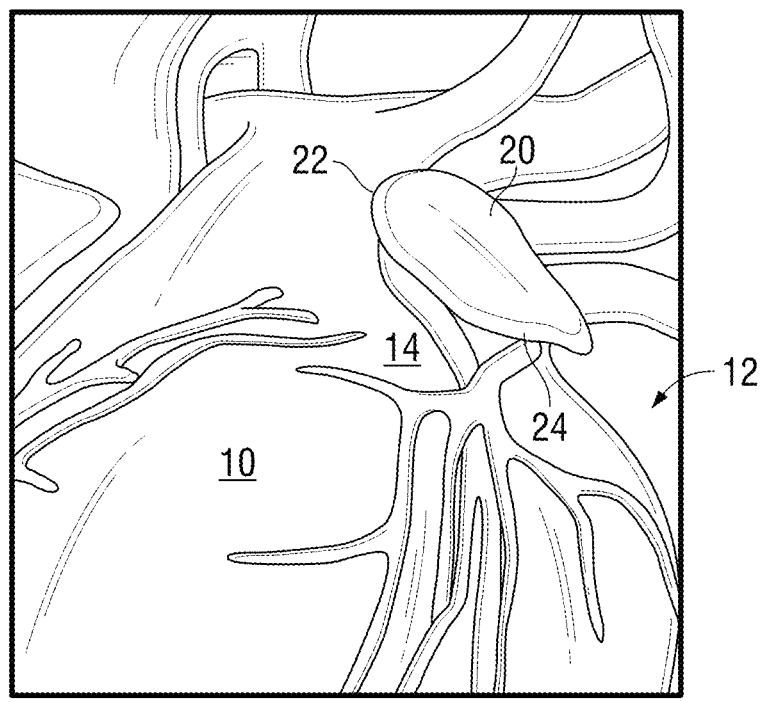
FIG. 1 is a fragmentary, diagrammatical illustration of a human heart with a left atrial appendage.
Figure 2:
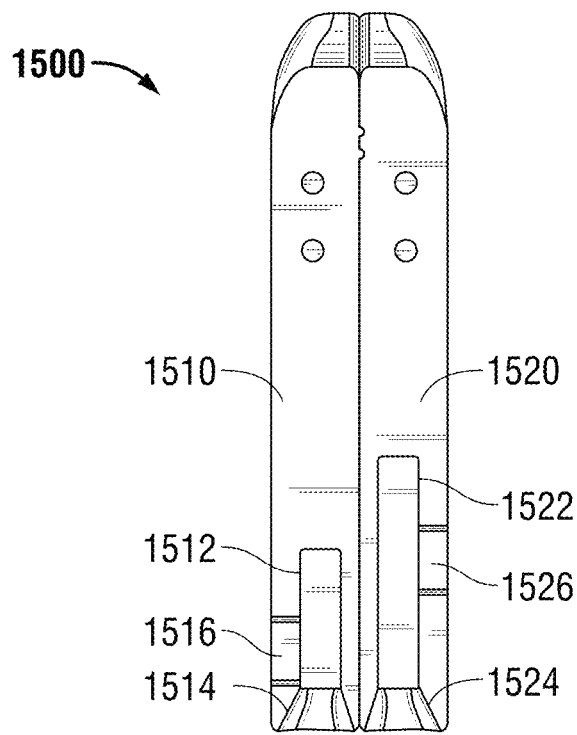
FIG. 2 is a fragmentary, cross-sectional view of an exemplary embodiment of an occlusion or exclusion clip with only struts of the clip present.

As required, detailed embodiments of the systems, apparatuses, and methods are disclosed herein; however, it is to be understood that the disclosed embodiments are merely exemplary of the systems, apparatuses, and methods, which can be embodied in various forms. Therefore, specific structural and functional details disclosed herein are not to be interpreted as limiting, but merely as a basis for the claims and as a representative basis for teaching one skilled in the art to variously employ the systems, apparatuses, and methods in virtually any appropriately detailed structure. Further, the terms and phrases used herein are not intended to be limiting; but rather, to provide an understandable description of the systems, apparatuses, and methods. While the specification concludes with claims defining the features of the systems, apparatuses, and methods that are regarded as novel, it is believed that the systems, apparatuses, and methods will be better understood from a consideration of the following description in conjunction with the drawing figures, in which like reference numerals are carried forward.

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Alternate embodiments may be devised without departing from the spirit or the scope of the invention. Additionally, well-known elements of exemplary embodiments of the systems, apparatuses, and methods will not be described in detail or will be omitted so as not to obscure the relevant details of the systems, apparatuses, and methods.

Before the systems, apparatuses, and methods are disclosed and described, it is to be understood that the terminology used herein is for the purpose of describing particular embodiments only and is not intended to be limiting. The terms "comprises," "comprising," or any other variation thereof are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element. The terms "including" and/or "having," as used herein, are defined as comprising (i.e., open language). The terms "a" or "an", as used herein, are defined as one or more than one. The term "plurality," as used herein, is defined as two or more than two. The term "another," as used herein, is defined as at least a second or more. The description may use the terms "embodiment" or "embodiments," which may each refer to one or more of the same or different embodiments.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact (e.g., directly coupled). However, "coupled" may also mean that two or more elements are not in direct contact with each other, but yet still cooperate or interact with each other (e.g., indirectly coupled).

For the purposes of the description, a phrase in the form "A/B" or in the form "A and/or B" or in the form "at least one of A and B" means (A), (B), or (A and B), where A and B are variables indicating a particular object or attribute. When used, this phrase is intended to and is hereby defined as a choice of A or B or both A and B, which is similar to the phrase "and/or". Where more than two variables are present in such a phrase, this phrase is hereby defined as including only one of the variables, any one of the variables, any combination of any of the variables, and all of the variables, for example, a phrase in the form "at least one of A, B, and C" means (A), (B), (C), (A and B), (A and C), (B and C), or (A, B and C).

Relational terms such as first and second, top and bottom, and the like may be used solely to distinguish one entity or action from another entity or action without necessarily requiring or implying any actual such relationship or order between such entities or actions. The description may use perspective-based descriptions such as up/down, back/front, top/bottom, and proximal/distal. Such descriptions are merely used to facilitate the discussion and are not intended to restrict the application of disclosed embodiments. Various operations may be described as multiple discrete operations in turn, in a manner that may be helpful in understanding embodiments; however, the order of description should not be construed to imply that these operations are order dependent.

As used herein, the term "about" or "approximately" applies to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. As used herein, the terms "substantial" and "substantially" means, when comparing various parts to one another, that the parts being compared are equal to or are so close enough in dimension that one skill in the art would consider the same. Substantial and substantially, as used herein, are not limited to a single dimension and specifically include a range of values for those parts being compared. The range of values, both above and below (e.g., "+/−" or greater/lesser or larger/smaller), includes a variance that one skilled in the art would know to be a reasonable tolerance for the parts mentioned.

Herein various embodiments of the systems, apparatuses, and methods are described. In many of the different embodiments, features are similar. Therefore, to avoid redundancy, repetitive description of these similar features may not be made in some circumstances. It shall be understood, however, that description of a first-appearing feature applies to the later described similar feature and each respective description, therefore, is to be incorporated therein without such repetition.

Described now are exemplary embodiments. Referring now to the figures of the drawings in detail and first, particularly to FIGS. 2 to 10, there is depicted distal portions of a first exemplary embodiment of a clip delivery device 1600 and an externally implantable and spring-biased, left atrial appendage, exclusion clip 1500.

An anterior view of the heart 10 in FIG. 1 illustrates how the LAA 20 projects away from and rests against the exterior surface 14 of the left atrium 12 to form a flap. In most instances, this flap formed by the LAA 20 against the exterior surface 14 is loose and the surgeon is able to manipulate the LAA 20 with a blunt Kittner dissector to stand the LAA to permit crossing of the LAA at the base 22. In such a position, the interior (e.g., 1572 in FIG. 9) of the exclusion clip 1500 is placed over the outermost point of the LAA 20 and the exclusion clip 1500 is slid down and around all sides of the LAA 20 so that the surgeon positions the excluding LAA sides (e.g., 1511, 1521 of FIG. 9) of the clip 1500 against the two opposing sides of the LAA 20 at the base 22 of the LAA 20. In some instances, however, the LAA 20 can have adhesions, which hold portions of a side 24 of the LAA 20 facing the left atrium 12 to the exterior surface 14 of the left atrium 12 or the pericardium. In such an instance, the flap of the LAA 20 is fixed in one or more areas and, therefore, cannot be manipulated by the surgeon to stand the LAA 20 away from the exterior surface 14 of the left atrium 12. More particularly, the right base of the LAA 20 (to the left of FIG. 1) is open and available to the surgeon but the opposite side, the left base (to the right of FIG. 1), is covered over by the left side of the LAA 20 (if the LAA 20 has grown in the other direction, then the opposite exists). Where adhesions exist, it is possible that the LAA 20 still can be manipulated sufficiently to allow a rod-shaped device to be inserted between the LAA 20 and the exterior surface 14 of the left atrium 12 and passed under the LAA (from anterior to posterior) along the left of the base 22 of the LAA 20 and through to the other side of the LAA 20 (adjacent the pulmonary artery). This means that, if an LAA-exclusion clip has a closed loop at distal end of the clip, the surgeon would be required to physically separate the left side of the LAA from the surface of the heart to use that particular clip. This separation is problematic for many reasons, one of which is that it can cause tearing of the LAA, which can have fatal consequences. In such a situation, therefore, it is desirable to approach the LAA 20 with an exclusion clip having an open distal end, such as clip 1500. An open-ended exclusion clip allows the surgeon to tunnel one strut of the clip between the left side of the LAA 20 and the left atrium 12 without being required to peel an adhesioned section of the LAA 20 from the exterior surface 14 of the left atrium 12.

A desirable feature of an LAA exclusion clip (e.g., clip 1500) is to be able to easily recapture the clip that has been implanted, whether during a clip-implantation procedure or after a clip has been implanted and exists on the LAA 20 for a period of time. Recapture is desirable for many reasons. One reason for needing recapture occurs after an LAA-exclusion clip has been implanted in a non-ideal manner. In such a situation, a final post-implantation imaging shows an undesirable placement of the clip, which placement might not be viewable while the delivery device remains connected to the clip (in other words, when the clip has been installed but not deployed off of the delivery device). In order to implant the clip, the surgeon must manually manipulate the heart into a position advantageous for deployment. In such a case, the delivery device impedes the ability of the heart to go back to its normal position, therefore, this can interfere with imaging of the clip in a final placement orientation. The delivery device can also be exerting an outside force that changes the anatomy and makes positive confirmation of good placement not possible. If the surgeon is not able to see the anatomical structures completely where the delivery device blocks such viewing, the only way to view actual placement is to release the clip from the delivery device. With recapture being possible, reconnection allows for repeatable imaging and recapture until a desired implantation position is achieved. When a clip is not able to be recaptured after final placement, if the implantation is unsatisfactory, then a second clip might be required to improve the surgery outcome, or the malpositioned clip would have to be removed by manual measures, such as cutting the clip or grasping with instruments not intended for the purpose. In either case, the risk to injury to the patient is greatly increased. Implantation of more than one clip is not desirable and recapture minimizes the necessity of multiple clip implantations. If the implanted clip cannot be improved by implanting a second clip, then it might be necessary to surgically cut the first clip off from the LAA. Such cutting is to be avoided as the potential for puncturing the atrium has significant fatal consequences. Simply put, for the most optimal exclusion of the LAA, a surgeon should be able to repeatedly:
  image the implanted clip;
  unclip a poorly implanted clip;
  reposition the clip; and
  image the repositioned implanted clip.

Desirably, the surgeon can repeat the unclipping, repositioning, and implanting steps as desired until a satisfactory placement occurs.

The exemplary embodiment of the clip 1500 can be sized to fit into a thoracoscopic port having an interior lumen of a given diameter, e.g., 10 mm (30 French). The clip 1500 has opposing clip struts 1510, 1520. These struts 1510, 1520 are biased to force LAA-compressing sides 1511, 1521 against one another with a bias device, such as a spring, which is not illustrated in FIGS. 2 and 4 to 21. Other features of the clip 1500 also are not illustrated for the sake of brevity. The proximal ends of the struts 1510, 1520 each have internal connector interfaces 1512, 1522. These internal connector interfaces 1512, 1522 have entrances 1514, 1524 into which a respective internal connector 1610, 1620 of the delivery device 1600 is inserted. At least one of the internal connector interfaces 1512, 1522 has a respective lock orifice 1516, 1526 into which a respective connector lock 1614, 1624 of the internal connectors 1610, 1620 is inserted. Both of the connector interfaces 1512, 1522 can have lock orifices 1516, 1526 as in the exemplary embodiment.

Figure 3:
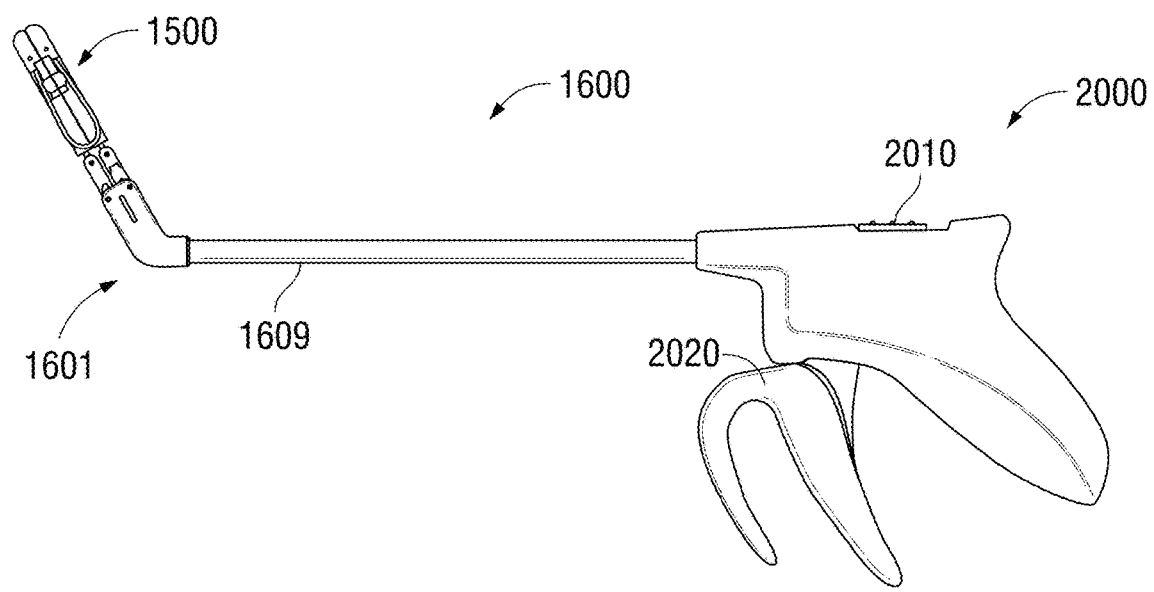
FIG. 3 is a side elevational view of an exemplary embodiment of a clip delivery device with an end effector with a clevis and jaws in a jaw-closed state, a shaft, and a handle, and an occlusion clip installed on the jaws.

The delivery device 1600 is used to deliver the clip 1500 to the LAA 20. An exemplary embodiment of the delivery device 1600 is shown in FIG. 3, in a pistol grip configuration. The delivery device 1600 has an end effector 1601, a shaft 1609, and a handle portion 2000. The delivery device 1600 has a lock/unlock controller 2010 (e.g., actuated through a clip lock pull cord) at the handle portion 2000. When actuated, the lock/unlock controller 2010 exerts a force (e.g., on the clip lock pull cord) to release a lock 1614, 1624 upon the clip struts 1510, 1520, thereby allowing the clip 1500 to leave the delivery device 1600 and be implanted. For recapture of the clip 1500, the delivery device 1600 is moved into a recapture position and first and second internal connectors 1610, 1620 (see, e.g., FIGS. 4 and 5) are respectively inserted into first and second connector interfaces 1512, 1522 of the clip struts 1510, 1520. In the exemplary embodiments described herein, the lock control (e.g., the lock release cord 1616, 1618 and the lock/unlock controller 2010) can automatically lock during recapture or the lock can be manually operated to lock the connectors 1610, 1620 within the connector interfaces 1512, 1522.

A first exemplary embodiment of a selectable locking mechanism for the struts 1510, 1520 is depicted FIGS. 4 to 11. To minimize the external diameter and allow for better port compatibility (e.g., to accommodate an internal diameter of approximately 10 mm/30 Fr or even smaller), it is desirable to have a release of the clip struts 1510, 1520 that occurs "internal" to the delivery device's control ends for the struts 1510, 1520. One example of an internal releasing structure is one that releases the clip 1500 from within the first and second internal connector interfaces 1512, 1522 that are in the form of blind holes.

The exemplary configurations shown in FIGS. 4 to 21 illustrate variations of an internal delivery device control of the struts 1510, 1520 (and thereby the LAA clip), the internal control allowing easy recapture and repositioning of the clip 1500.

Figure 4:
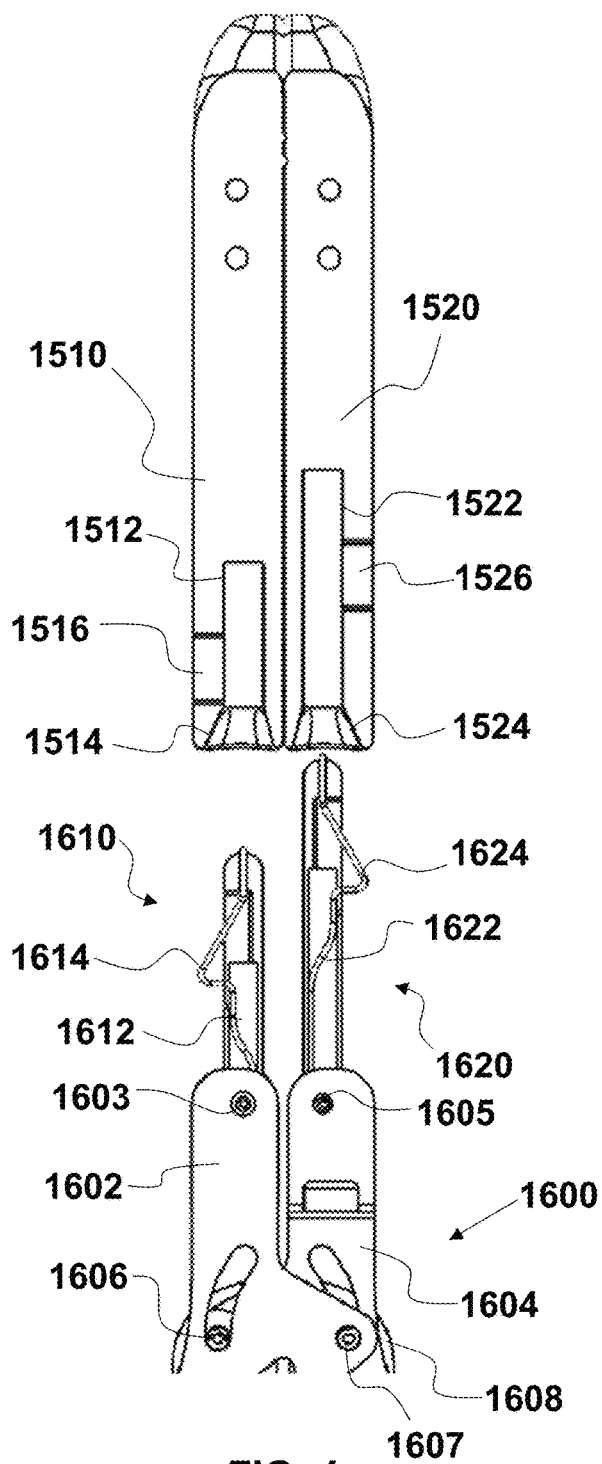
FIG. 4 is a fragmentary, cross-sectional view of the end effector and occlusion clip of FIG. 2 with the occlusion clip at a distance from the jaws.

A first exemplary embodiment of the internal strut control mechanism allowing for recapture is shown in FIGS. 4 to 11. The progression from FIG. 4 to FIG. 7 illustrates stages in the installation and implantation of a clip 1500 comprising the struts 1510, 1520 (as above, only the struts 1510, 1520 of the clip 1500 are illustrated for clarity). FIG. 4 illustrates both the step of final disconnection of the struts 1510, 1520 from the delivery device 1600 and the step of connection of the struts 1510, 1520 to the delivery device 1600.

Figure 11:
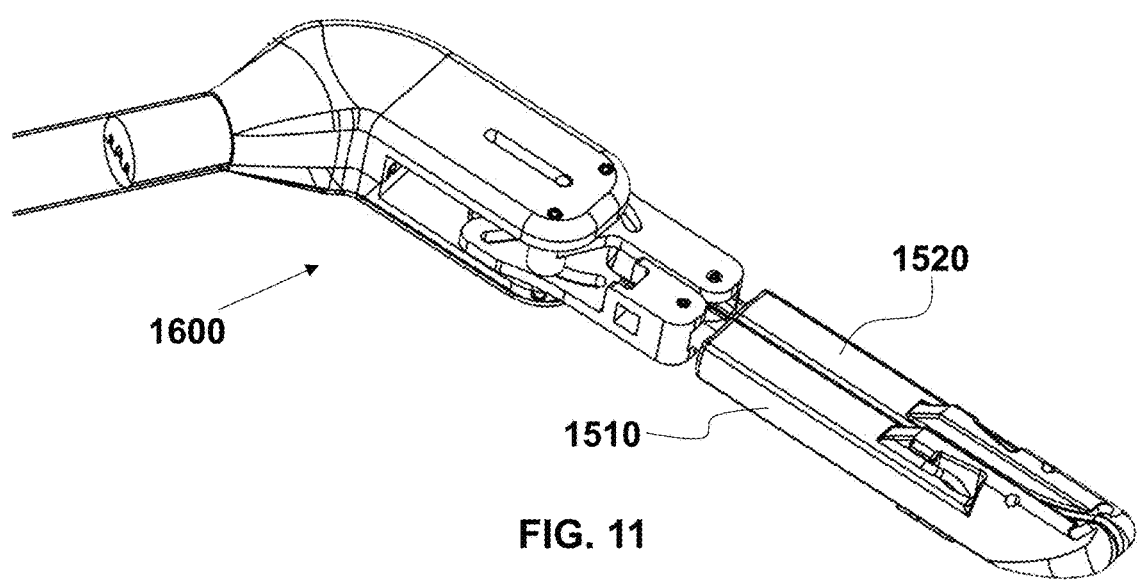
FIG. 11 is a fragmentary, perspective view of the end effector and occlusion clip of FIG. 7.
Figures 9, 10:
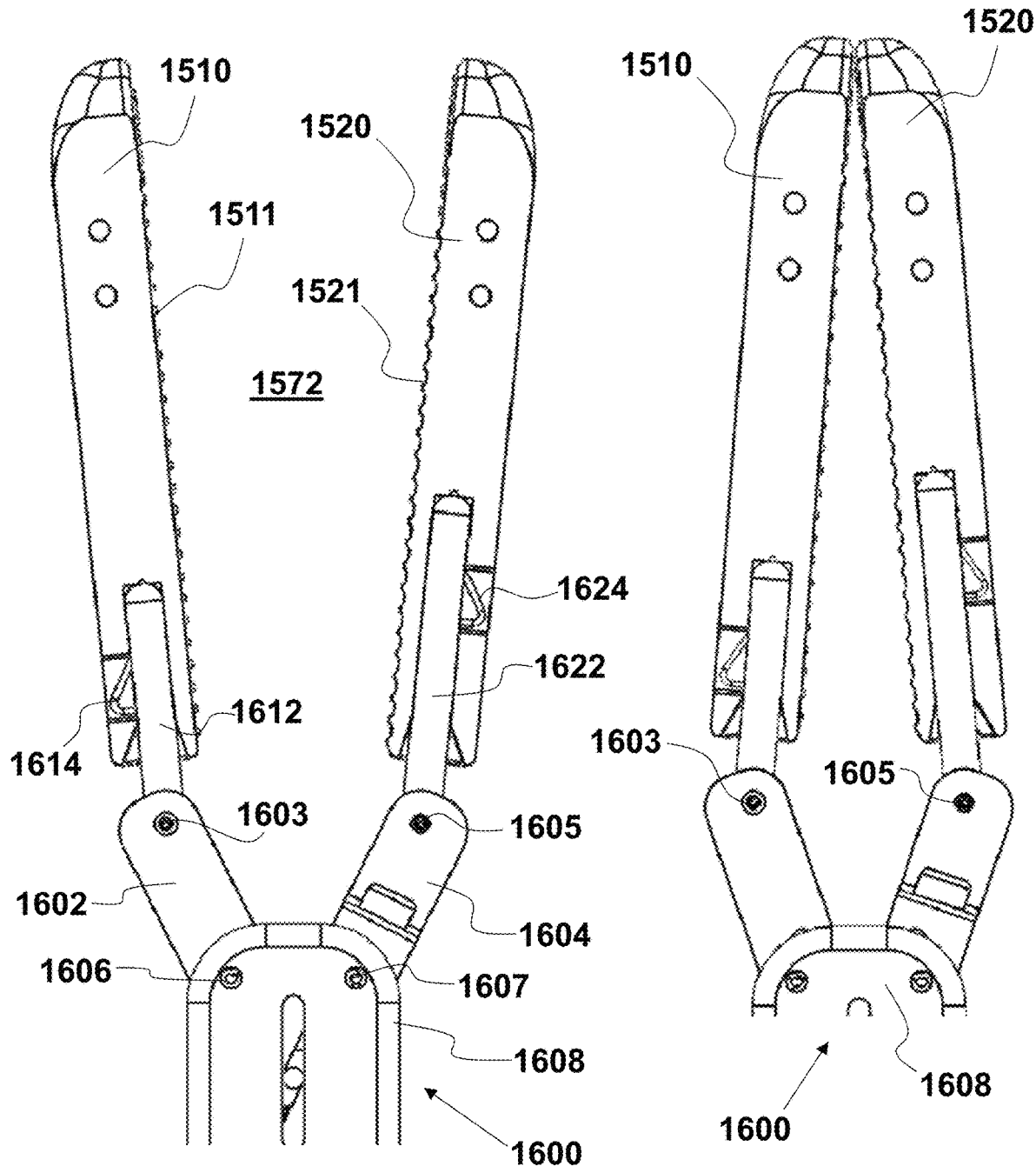
FIG. 9 is a fragmentary, cross-sectional view of the end effector and occlusion clip of FIG. 7 with the jaws in an opened state and with struts of the occlusion clip opened with tips pointing away from one another.
FIG. 10 is a fragmentary, cross-sectional view of the end effector and occlusion clip of FIG. 7 with the jaws in an opened state and with struts of the occlusion clip opened with tips pointing towards one another.

In each of the embodiments, the delivery device 1600 comprises first and second delivery cams 1602, 1604 respectively connected to each of the struts 1510, 1520. The first and second delivery cams 1602, 1604 are respectively pivotally connected to first and second internal connectors 1610, 1620 at a distal pivot 1603, 1605 and the first and second delivery cams 1602, 1604 are respectively pivotally connected to a delivery clevis 1608 at a respective one of first and second proximal pivots 1606, 1607. Non-illustrated cam actuation connectors control the movement of the delivery cams 1602, 1604 with respect to one another (e.g., opening and closing as shown in FIGS. 10 and 11). A beneficial characteristic arises with the first and second distal pivots 1603, 1605. By allowing the first and second internal connectors 1610, 1620 to pivot freely about a small angle (e.g., between >0° and approximately 60°, in particular, between approximately 20° and approximately 40°, particularly, approximately 30°), the internal connectors 1610, 1620 permit easy self-alignment so that when the second internal connector 1620 is inserted (as it is longer) into an internal connector interface (e.g. 1512, 1522), the first internal connector 1610 can be pivoted as desired with the second internal connector 1620 remaining relatively still, referred to herein as passive alignment. Lengths of the internal connectors 1610, 1620 are discussed in further detail below.

In an exemplary alternative embodiment to motion of the jaws pivoting about pivot pins in the clevis, for example, the jaws and clevis is a singular component with live hinges for pivoting. In another exemplary embodiment, arcing tracks or constraints provide a virtual pivot about which the jaws move. Further, the end effector does not require a pivoting motion to achieve opening and closing motion of the clip struts. The jaws can move symmetrically or asymmetrically about a central vertical plane between the clip struts by non-rotationally based motion such as constraining features in the clevis, such as tracks or grooves, which guide the motion of the first jaw relative to the second jaw along a linear, curved, or otherwise non-linear path. In another exemplary embodiment, the jaws and clevis can be connected by flexures, enabling motion of the first and second jaws along a linear, curved, or otherwise non-linear path.

Figure 22:
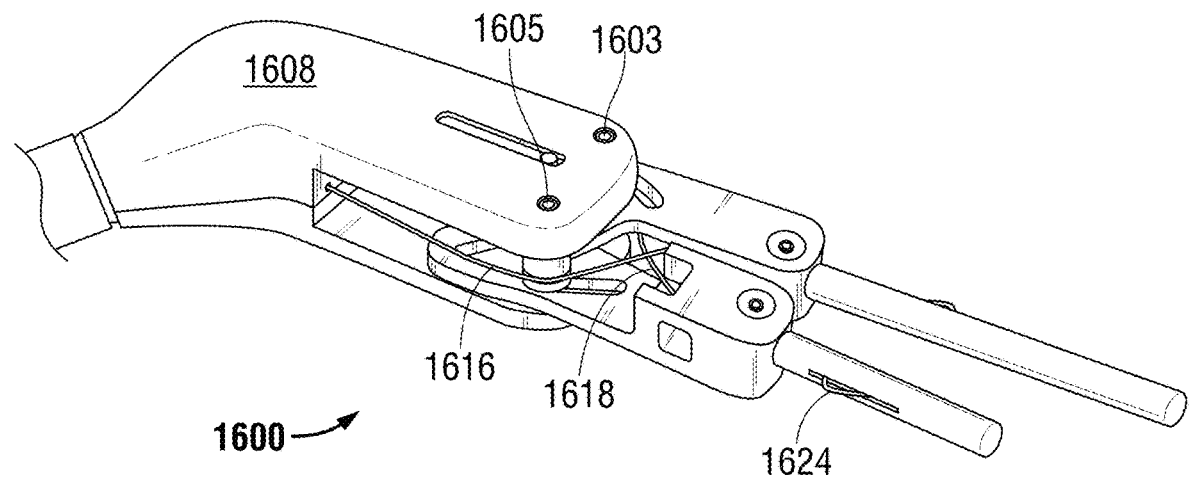
FIG. 22 is a fragmentary, perspective view of the end effector of FIG. 3.
Figure 5:
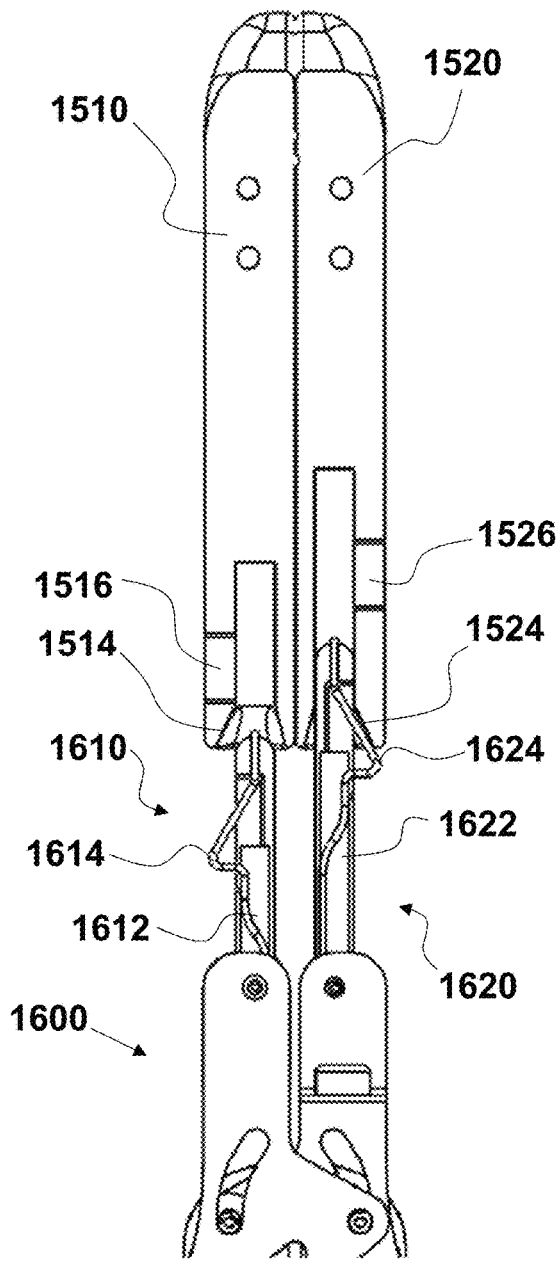
FIG. 5 is a fragmentary, cross-sectional view of the end effector and occlusion clip of FIG. 4 with the occlusion clip partially installed on the jaws in a first intermediate state.

The progression from FIGS. 4 to 7 illustrates how the struts 1510, 1520 are connected respectively to the first and second internal connectors 1610, 1620. In this exemplary embodiment, the struts 1510, 1520 have respective internal connector interfaces 1512, 1522, here in the form of cylindrical, blind holes. Likewise, the first and second internal connectors 1610, 1620 have first and second shafts 1612, 1622 each with an external shape corresponding to the respective internal connector interfaces 1512, 1522 for mating therein. Here, the shapes are similar, having a circular cross-section and a rounded tip. However, the shapes of the two shafts 1612, 1622 can be different, for example, one circular and one polygonal in cross-section. If the shafts 1612, 1622 were simply inserted within the internal connector interfaces 1512, 1522, then it would be possible for the struts 1510, 1520 to slip off. To retain each of the struts 1510, 1520 on the respective shafts 1612, 1622, at least one of the internal connectors 1610, 1620 is provided with the connector lock 1614, 1624, or both of the internal connectors 1610, 1620 are provided with connector locks 1614, 1624. In the exemplary embodiment of FIGS. 4 to 10, the connector locks 1614, 1624 are in the form of a triangle. The triangle is formed from a deformable cord (e.g., a Nitinol or another NiTi alloy wire) that acts as a "one-way" catch. The catch is deemed one-way because it allows easy insertion of the internal connectors 1610, 1620 into the internal connector interface 1512, 1522 (the catch bends out of the way for insertion) but resisting removal of the internal connectors 1610, 1620 out from the internal connector interface 1512, 1522 until a given amount of force is overcome. More specifically with regard to the progression from FIG. 4 to FIG. 7, for removable capture of the clip onto the delivery device 1600, the shafts 1612, 1622 are slid respectively into the internal connector interfaces 1512, 1522. In FIG. 5, the internal connectors 1610, 1620 are in a first intermediate inserted position. Here, the distal end of the shaft 1622 is within the second internal connector interface 1522 sufficient to touch the triangular portion of the second connector lock 1624 against a second entrance 1524 of the second internal connector interface 1522. A desirable exemplary shape of the second entrance 1524 (and of the first entrance 1514) is conical with a cone angle corresponding to an angle of the triangular portion of the second connector lock 1624 that first touches the entrance 1524 (e.g., it is an acute angle). A conical shape of the entrance 1524 is desirable to enable the user to insert the shafts 1612, 1622 into the internal connector interfaces 1512, 1522 and to allow the shafts 1612, 1622 to enter therein even if the central axes of the shafts 1612, 1622 are slightly out of alignment with the central axes of the internal connector interfaces 1512, 1522. In order to unlock the connector locks 1614, 1624, first and second lock release cords 1616, 1618 (see, e.g., FIG. 22) are connected respectively to the proximal ends thereof and a force applied at the proximal end of the first and second lock release cords 1616, 1618 causes the triangle of the connector locks 1614, 1624 to deform and collapse, thereby removing the catch from the lock orifices 1516, 1526. Together, the lock release cords 1616, 1618 and the lock/unlock controller 2010 form a lock control. As shown in FIG. 22, the first and second lock release cords 1616, 1618 approach from opposite sides of the longitudinal axis of the end effector that is the delivery device 1600. Crossing over of these first and second lock release cords 1616, 1618 keeps the delivery cams 1602, 1604 biased towards the center axis in a relatively parallel orientation and, with at least a small angle of cross-over, the first and second lock release cords 1616, 1618 bias the jaws of the end effector shut.

Figure 6:
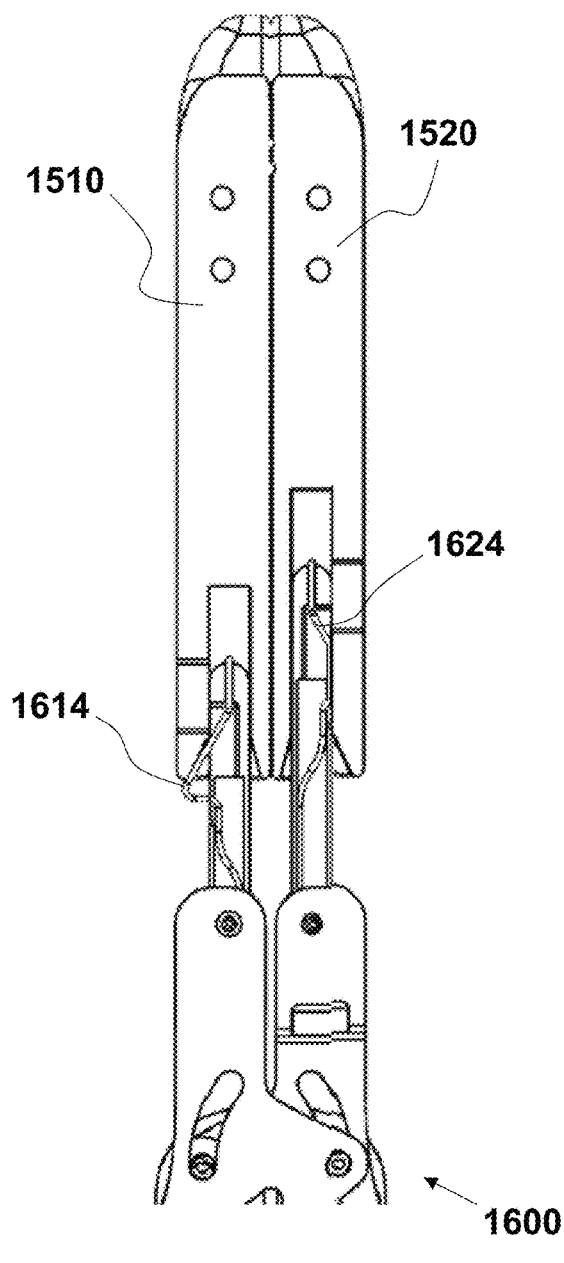
FIG. 6 is a fragmentary, cross-sectional view of the end effector and occlusion clip of FIG. 4 with the occlusion clip further partially installed on the jaws in a second intermediate state.
Figure 7:
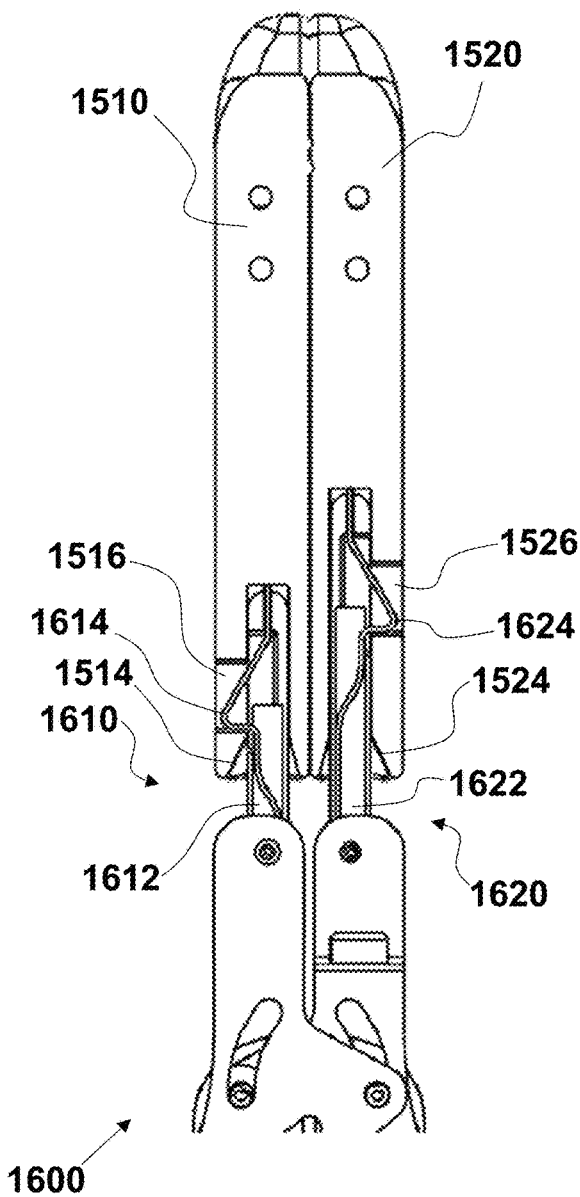
FIG. 7 is a fragmentary, cross-sectional view of the end effector and occlusion clip of FIG. 4 with the occlusion clip removably installed on the jaws.
Figures 8, 8A:
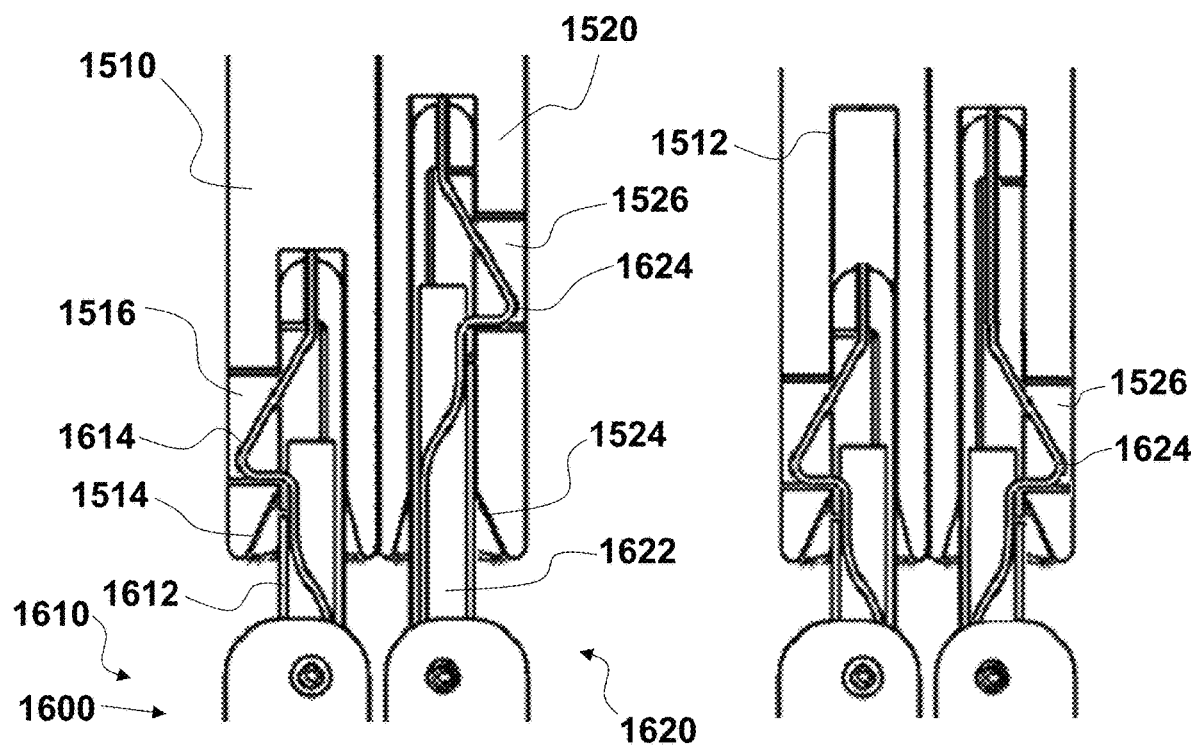
FIG. 8 is a fragmentary, enlarged, cross-sectional view of an intermediate portion of the end effector and occlusion clip of FIG. 7.
FIG. 8A is a fragmentary, enlarged, cross-sectional view of an intermediate portion of the end effector and occlusion clip of FIG. 7 with an alternative exemplary embodiment of internal connectors of the end effector, internal connector interfaces of the clip struts, and locking parts of a lock that removably secures the occlusion clip to the end effector.

Each of the internal connector interfaces 1512, 1522 comprises a lock orifice 1516, 1526. As the shafts 1612, 1622 are inserted further into the internal connector interfaces 1512, 1522, the second connector lock 1624 is deformed (e.g., to collapse the NiTi wire) within the second internal connector interface 1522 (as shown in FIG. 6). With further insertion of the internal connectors 1610, 1620, the first connector lock 1614 is then deformed within the first internal connector interface 1512. The two connector locks 1614, 1624 are positioned longitudinally to expand and snap into the respective lock orifice 1516, 1526 when the internal connectors 1610, 1620 are in a final insertion position within the internal connector interfaces 1512, 1522, which is shown in FIGS. 7 and 8. Deformability of the connector locks 1614, 1624 are set so that the surgeon can feel removal of the struts 1510, 1520 from the delivery device 1600 (e.g., tactilely) but are not too strong to cause significant movement of the struts 1510, 1520 on tissue that is compressed between the opposing tissue contacting surfaces of the struts 1510, 1520 during implantation. Another reason to lock the struts 1510, 1520 onto the delivery device 1600 is that the force of expanding the struts 1510, 1520 from one another (as shown, for example, in FIGS. 9 and 10) tends to cause the struts 1510, 1520 to eject off of the internal connectors 1610, 1620 forcibly, an action referred to as watermelon seeding off of the delivery device 1600. One of the significant benefits to having a self-locking connection between the delivery device 1600 and the struts 1510, 1520 is that the user does not need to actuate anything at the proximal end of the delivery device (for example, pulling on a trigger or sliding a slide) in order to lock the clip onto the delivery device 1600, this is especially beneficial during recapture for reimplantation. Due to the ramp configuration of the connector locks 1614, 1624, there is no user input required to re-lock the struts 1510, 1520; in other words, there is an automatic locking of the struts 1510, 1520 onto the delivery device merely by sliding the internal connectors 1610, 1620 into the struts 1510, 1520.

As can be seen from the exemplary configurations of the delivery device 1600 and the struts 1510, 1520 (e.g., in FIGS. 4 to 10), the internal connectors 1610, 1620 are of different lengths. If both of the internal connectors 1610, 1620 are the same length, then it is difficult for an operator/surgeon to visualize each internal connector 1610, 1620 enter the respective internal connector interfaces 1512, 1522. This is especially true when visualization is two-dimensional and one of the internal connectors 1610, 1620 physically blocks the other. It is more difficult to coordinate two pins to simultaneous insert into respective holes than inserting one at a time. In contrast, when the internal connectors 1610, 1620 are of different lengths as in the exemplary configurations, the operator can place the longer internal connector 1620 at a visualization position further than the shorter internal connector 1610. As a result, when the operator moves the internal connectors 1610, 1620 into the internal connector interfaces 1512, 1522, the one that is longer can be seen to enter the respective internal connector interface and, subsequently, the one that is shorter can be seen to enter its internal connector interface without any obstruction. In other words, the operator needs to only line up one of the internal connectors 1620 with its respective internal connector interface 1522 and, with a little insertion, the other internal connector 1610 can be aligned easily to be inserted into its respective internal connector interface 1512. The biasing to parallel of the internal connectors 1610, 1620 and delivery cams 1602, 1604 by the lock release cords 1616, 1618 is what positions the connectors 1610, 1620 in approximately the correct position to make alignment of the second internal connector 1620 easy and, once the second connector 1620 is partially engaged (e.g., FIG. 5), this positions the first connector 1610 for easy alignment with the internal connector interface 1512. Once the clip 1500 is implanted on tissue, the spacing between the struts 1510, 1520 and the angle between them is dictated by the tissue between them. This makes the relative angle variable and requires that the connectors 1610, 1620 and the cams 1602, 1604 be able to change in angle and relative spacing with very light forces so they can move to match the implanted clip 1500, which makes the connectors 1610, 1620 "free floating" for matching the axis of the strut 1510, 1520 with a lowest force possible. This free floating aspect of the connectors 1610, 1620 and the cams 1602, 1604 is described in further detail below. As can be seen, therefore, the first internal connector 1610 is an assembly comprising the first shaft 1612 and the first connector lock 1614. Likewise, the second internal connector 1620 is an assembly comprising the second shaft 1622 and the second connector lock 1624.

Another exemplary embodiment for the interaction between the internal connector interfaces 1512, 1522 and the internal connectors 1610, 1620 is depicted in FIG. 8A. With internal connector interfaces 1512, 1522 that are of different lengths (as in FIGS. 4 to 8) corresponding to the different lengths of the first and second internal connectors 1610, 1620, the first and second internal connectors 1610, 1620 can only engage the struts 1510, 1520 in one orientation, that orientation depicted in FIGS. 4 to 8. By moving the second lock orifice 1526 in the second internal connector interface 1522 to the same longitudinal position as the first lock orifice 1516 in the first internal connector interface 1512 and by increasing the (blind) hole distance of the first internal connector interface 1512 to at least the length of the longer second shaft 1622 of the second internal connector 1620, as shown in FIG. 8A, the delivery device 1600 can be made to insert the internal connectors 1610, 1620 in either orientation (e.g., a left-handed approach or a right-handed approach).

Figure 12:
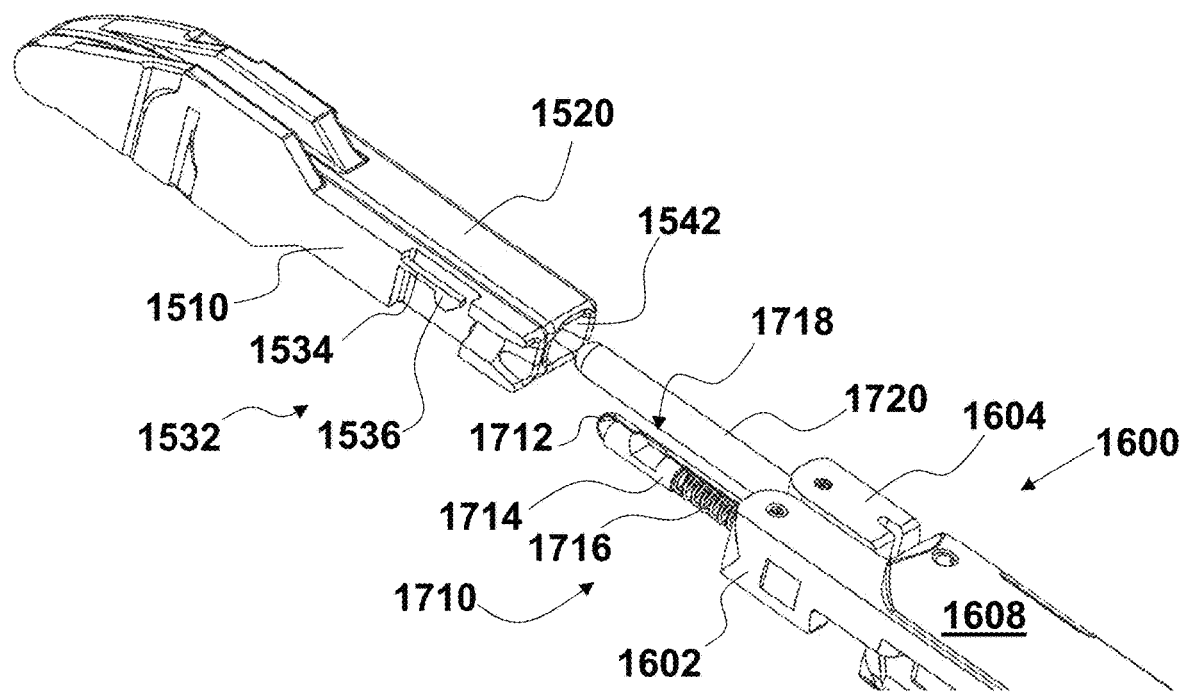
FIG. 12 is a fragmentary, perspective view of an exemplary embodiment of an end effector having a clevis and jaws in a jaw-closed state, and of an occlusion clip at a distance from the jaws and with only struts of the clip present.
Figure 13:
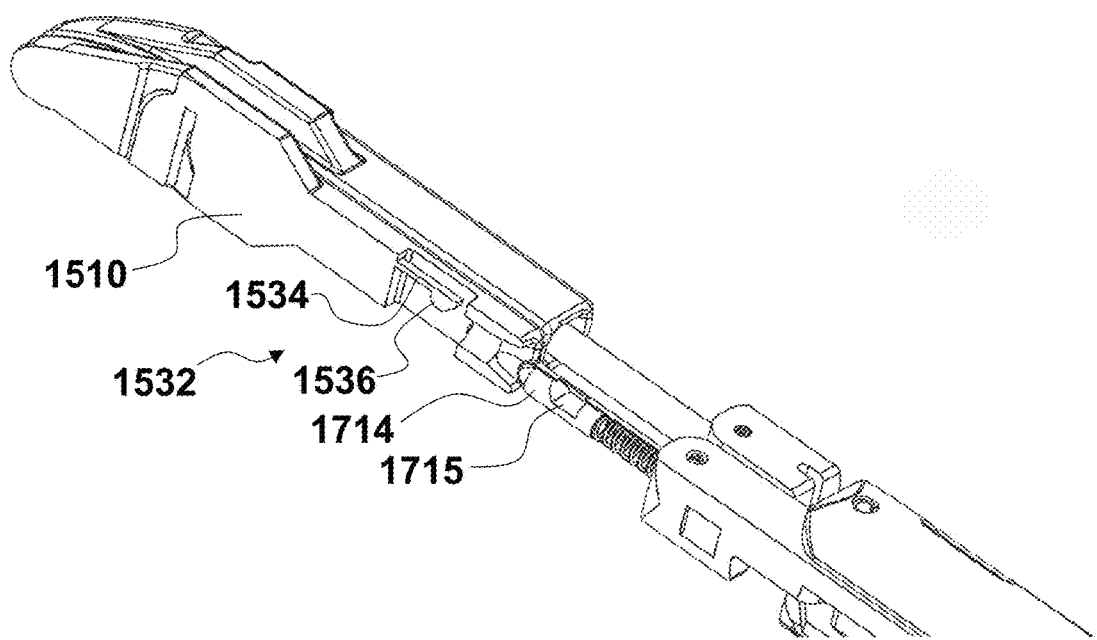
FIG. 13 is a fragmentary, perspective view of the end effector and occlusion clip of FIG. 12 with the occlusion clip partially installed on the jaws in a first intermediate state.
Figure 14:
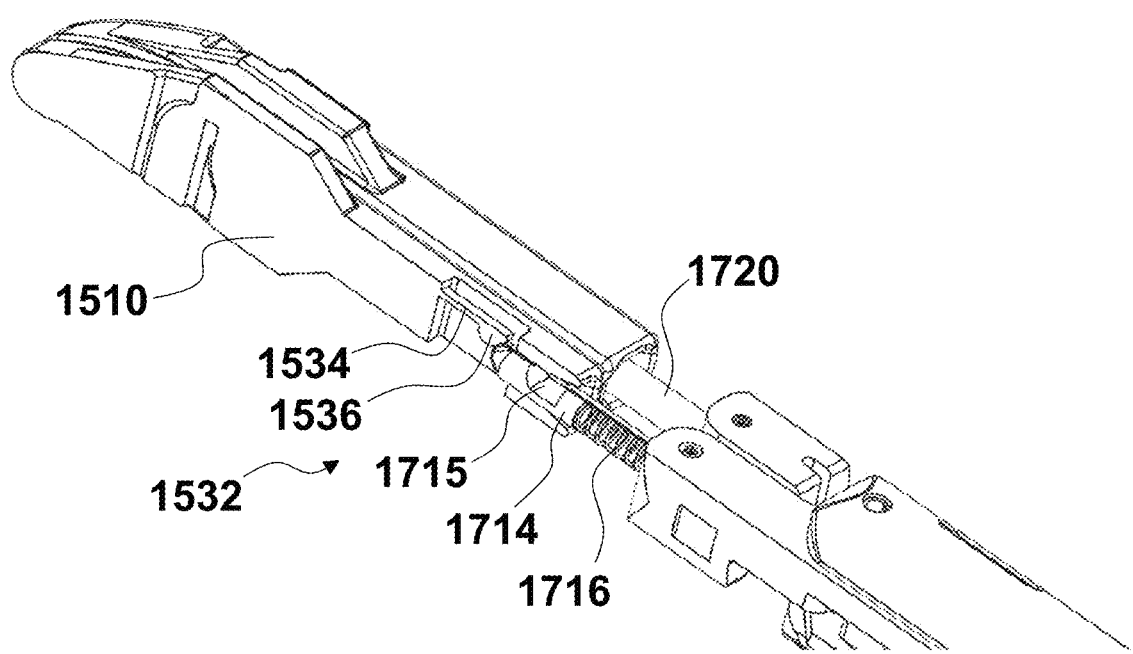
FIG. 14 is a fragmentary, perspective view of the end effector and occlusion clip of FIG. 12 with the occlusion clip further partially installed on the jaws in a second intermediate state.

A second exemplary embodiment of the internal strut control mechanism allowing for recapture is shown in FIGS. 12 to 17. All of the aspects of this mechanism are similar to that shown in and described with respect to FIGS. 4 to 11 and, therefore, some aspects are not repeated herein. All aspects thereof are, however, incorporated in their entirety herein. The progression from FIG. 12 to FIG. 14 illustrates stages in the installation (FIG. 12 to FIG. 14) and deployment (FIG. 14 to FIG. 12) of a clip comprising the struts 1510, 1520 (only the struts 1510, 1520 of the clip are illustrated for clarity and all clips described and/or shown herein are applicable to a clip with these struts 1510, 1520). FIG. 12 illustrates both the step of final disconnection of the struts 1510, 1520 from the delivery device 1600 and the step of connecting the struts 1510, 1520 to the delivery device 1600. The progression from FIG. 12 to FIG. 15 illustrates how the struts 1510, 1520 are connected respectively to the first and second internal connectors 1710, 1720 and insert respectively into first and second internal connector interfaces 1532, 1542. As indicated by the different numerals, the first and second internal connectors 1710, 1720 differ from the first and second internal connectors 1610, 1620 and the first and second internal connector interfaces 1532, 1542 differ from the first and second internal connector interfaces 1512, 1522.

In the exemplary embodiment of FIGS. 12 to 17, the first and second internal connector interfaces 1532, 1542 are different from one another. The second internal connector interface 1542 is in the form of a cylindrical, blind hole. The second internal connector interface 1542, therefore, forms a guide into which the second internal connector 1720 inserts. When fully inserted, the second internal connector 1720 rests slidably within the second internal connector interface 1542. In contrast, the first internal connector 1710 is an assembly comprising a hollow tubular shell 1712 housing therein a locking plunger 1714, and a bias device 1716 connected to the proximal end of the plunger 1714 and grounded at a non-illustrated proximal position within the tubular shell 1712 adjacent and/or inside the first delivery cam 1602. Also not illustrated is a control cord (e.g., the lock release cords 1616, 1618) that is fixed to the proximal end of the plunger 1714 on one end and connected to the lock/unlock controller 2010 at the handle 2000 of the delivery device 1600 (see FIG. 3). When actuated, the lock/unlock controller 2010 exerts a force on the lock release cords 1616, 1618 to move the plunger 1714 proximally within the tubular shell 1712. The tubular shell 1712 is cross-sectioned in FIGS. 12 to 15 so that the plunger 1714 and the bias device 1716 is visible in those figures.

The first internal connector interface 1532 also is an assembly having various portions. The assembly comprises a lock 1534 connected at a distal end to the strut 1510 and extending in a longitudinal proximal direction towards the delivery device 1600. The lock 1534 has a locking surface 1536 shaped to enter into and lock within a corresponding keyhole 1715 of the locking plunger 1714. Because of the cross-sectioning of the tubular shell 1712, an opening 1718 in the tubular shell 1712 is partially shown in these figures. The first and second internal connectors 1710, 1720 each have an external shape corresponding to the respective internal surfaces of the first and second internal connector interfaces 1532, 1542 for mating therein. Here, the exterior shapes are similar, having a circular cross-section and a rounded tip. However, the shapes of the two internal connector 1532, 1542 can be different, for example, one circular and one polygonal in cross-section. The lock 1534 prevents the struts 1510, 1520 from slipping off of the delivery device 1600 after the first and second internal connectors 1710, 1720 are inserted within the internal connector interfaces 1532, 1542.

Figure 15:
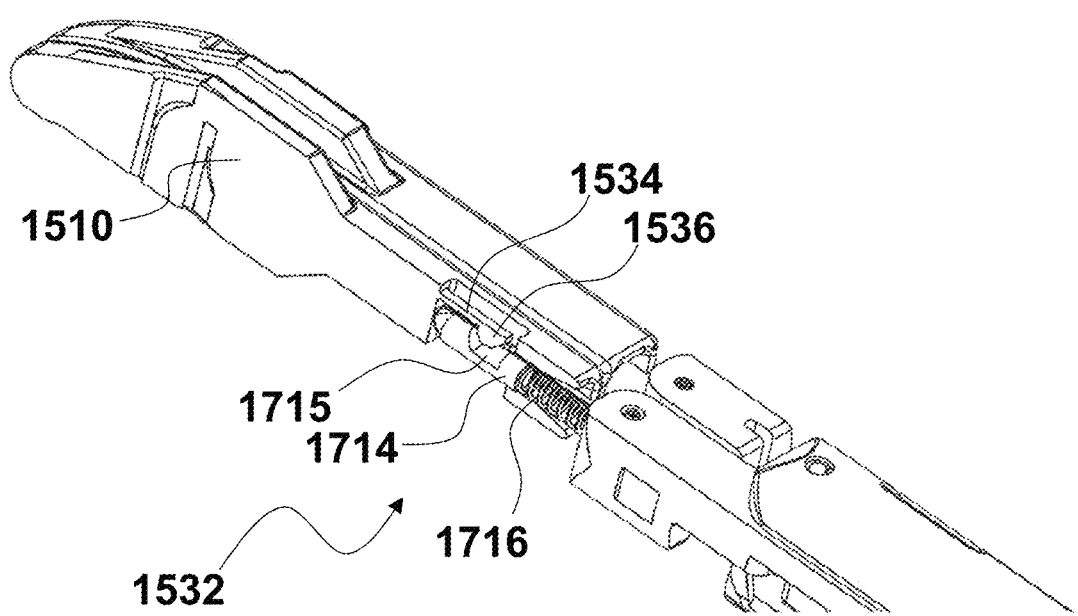
FIG. 15 is a fragmentary, perspective view of the end effector and occlusion clip of FIG. 12 with the occlusion clip removably installed on the jaws.
Figure 16:
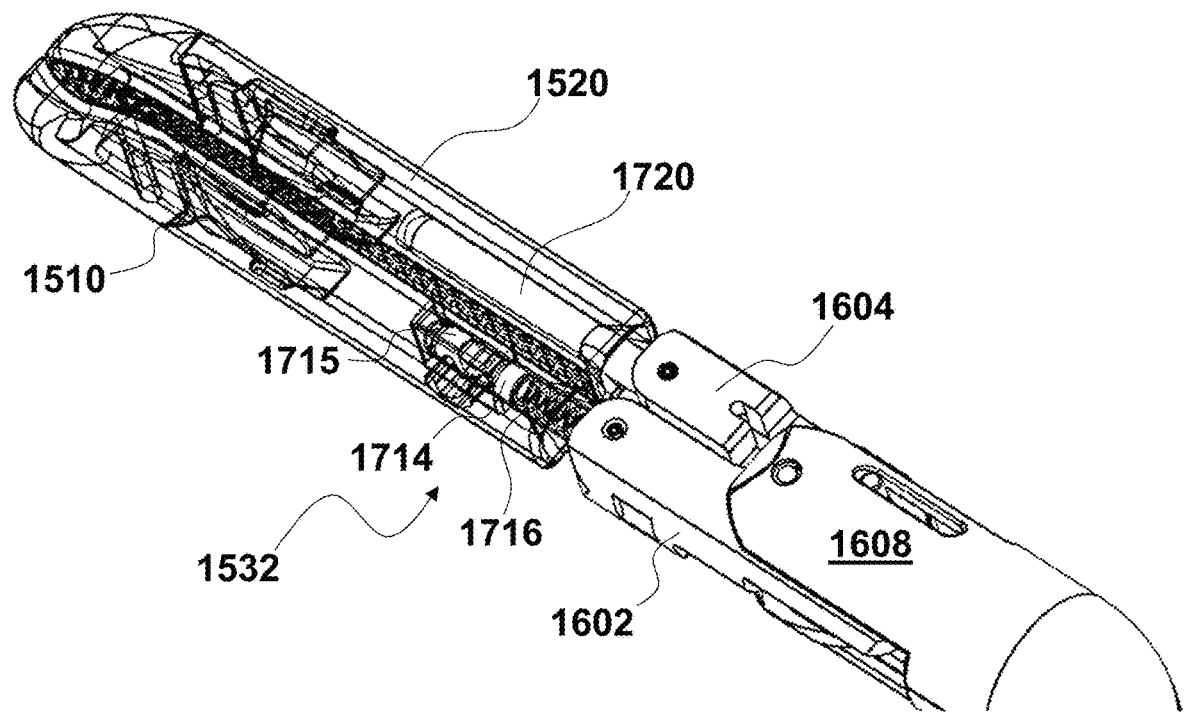
FIG. 16 is a fragmentary, perspective and partially transparent view of the end effector and occlusion clip of FIG. 15.
Figure 17:
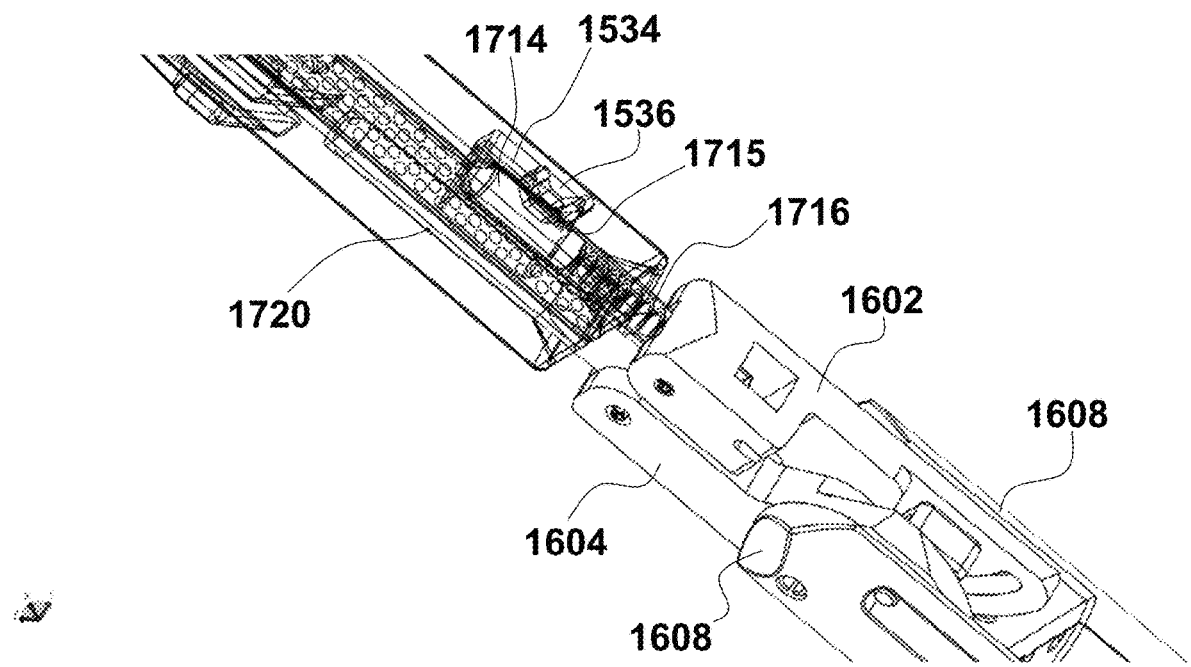
FIG. 17 is a fragmentary, enlarged, perspective and partially transparent view of the end effector and occlusion clip of FIG. 16 rotated to view a lower side.
Figure 23:
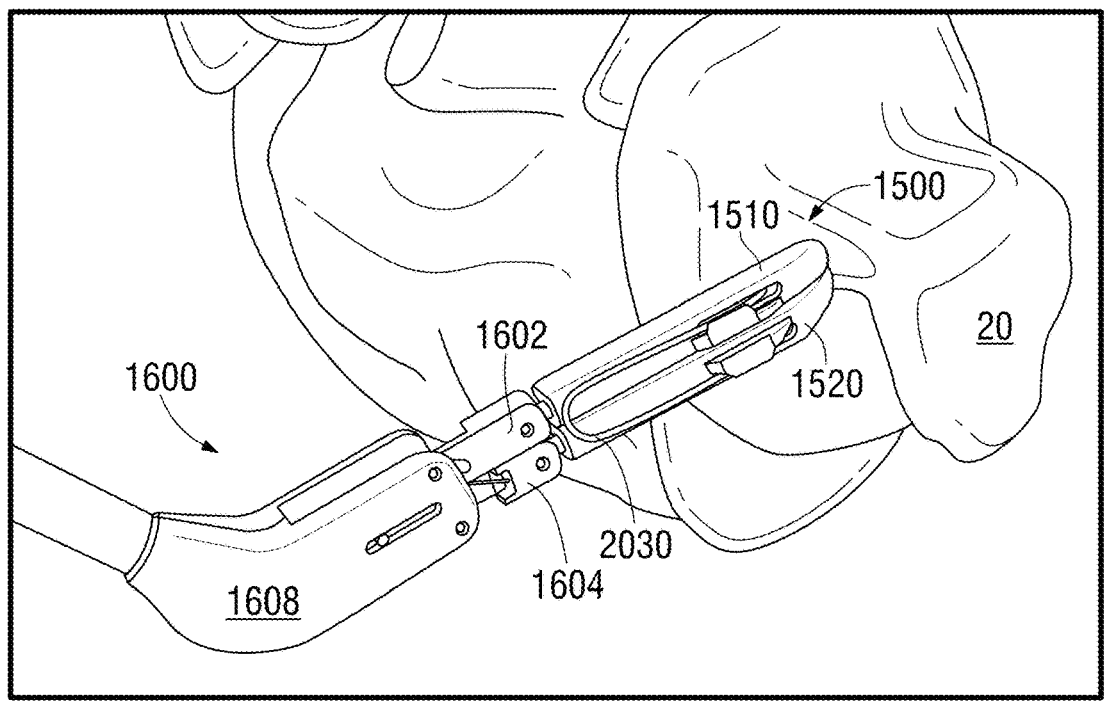
FIG. 23 is a fragmentary, perspective view of the end effector and clip of FIGS. 2, 12, 18, 34, 39, 41, 53, and 66 with the clip installed on the end effector in a clip-closed state adjacent an exemplary embodiment of a LAA.

FIG. 13 shows the second internal connector 1720 inserted within the second internal connector interface 1542 and the first internal connector 1710 not yet inserted within the first internal connector interface 1532. FIG. 14 shows the second internal connector 1720 inserted further within the second internal connector interface 1542 and the locking plunger 1714 of first internal connector 1710 inserted within a proximal portion of the first internal connector interface 1532. The locking surface 1536 is not yet inserted into the keyhole 1715 in this state. Finally, FIG. 15 shows a locked state of the clip where the second internal connector 1720 is inserted within the second internal connector interface 1542 and the tubular shell 1712 is inserted sufficiently far in the first internal connector interface 1532 to lock the locking surface 1536 in the keyhole 1715 of the locking plunger 1714. With the locking surface 1536 inserted within the keyhole 1715, the strut 1510 (and thereby the second strut 1520 connected thereto) is locked temporarily upon the delivery device 1600, temporarily meaning that the surgeon can unlock the clip 1500 when desired to allow implantation of the clip 1500. An example of this locked state is shown in FIG. 23. In order to unlock the clip 1500 from the delivery device 1600, the operator/surgeon actuates the lock/unlock controller 2010 at the handle 2000 to exert a proximal force on the locking plunger 1714. This force is greater than the force exerted by the lock 1534 on the locking plunger 1714 and, thereby, unlocks the lock 1534. In this particular exemplary embodiment, the locking surface 1536 is curved and/or angled and the keyhole 1715 is curved and/or angled such that, when the locking plunger 1714 is forced proximally, the lock 1534 bends and the locking surface 1536 slides out of the keyhole 1715. The features of the lock described and shown are merely exemplary and other forms of a locking connection are equally possible.

Figure 18:
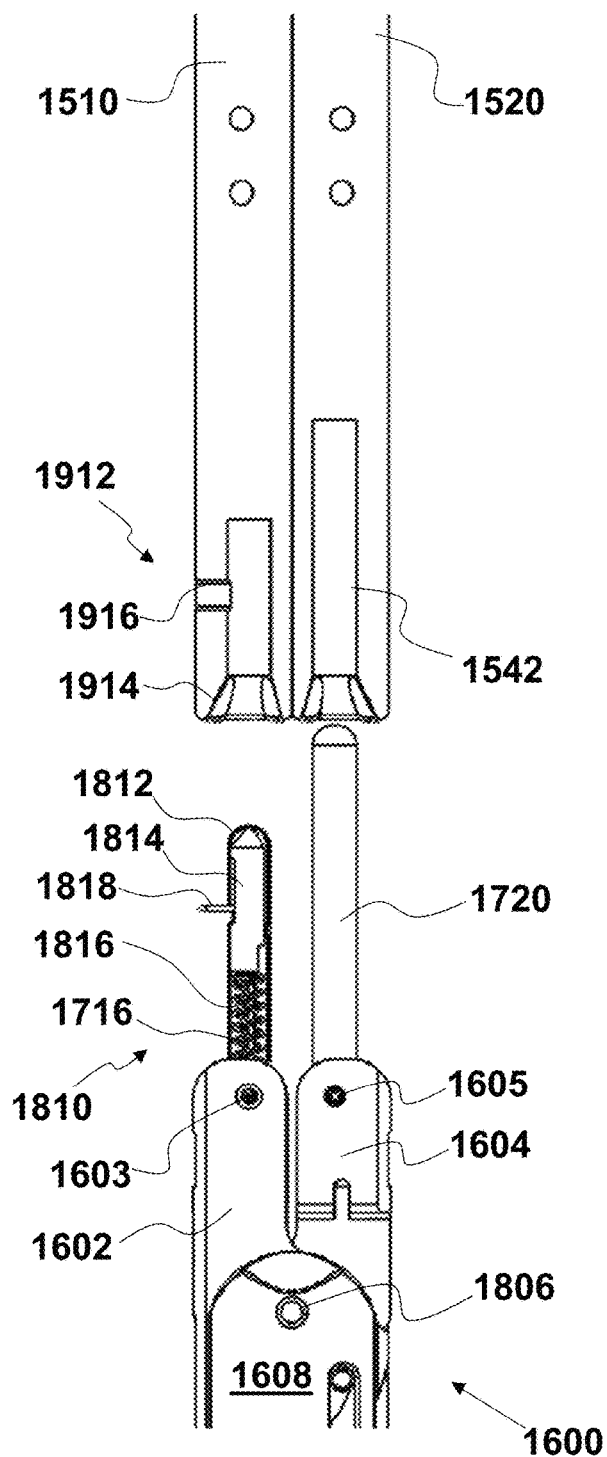
FIG. 18 is a fragmentary, cross-sectional view of an exemplary embodiment of an end effector having a clevis and jaws in a jaw-closed state, and of an occlusion clip at a distance from the jaws and with only struts of the clip present.
Figure 19:
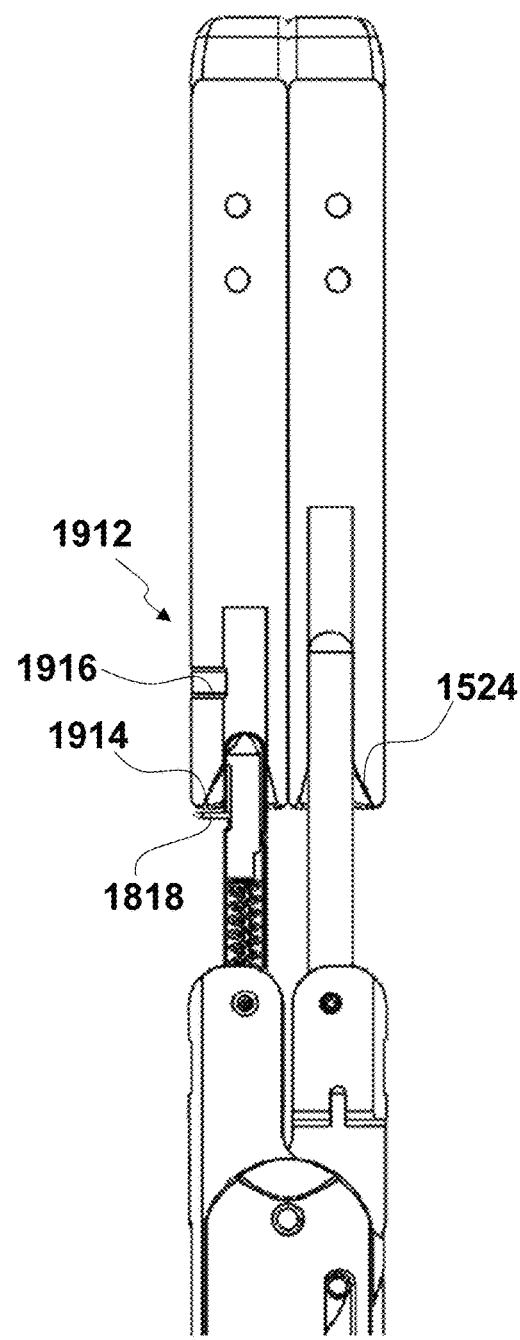
FIG. 19 is a fragmentary, cross-sectional view of the end effector and occlusion clip of FIG. 18 with the occlusion clip partially installed on the jaws in an intermediate state.

A third exemplary embodiment of the internal strut control mechanism allowing for recapture is shown in FIGS. 18 to 21. All of the aspects of this mechanism are similar to that shown in and described with respect to FIGS. 4 to 17 and, therefore, some aspects are not repeated herein. All aspects thereof are, however, incorporated in their entirety herein. The progression from FIG. 18 to FIG. 20 illustrates stages in the installation and deployment/implantation of a clip comprising the struts 1510, 1520 (only the struts 1510, 1520 of the clip are illustrated for clarity and all clips described and/or shown herein are applicable to a clip with these struts 1510, 1520). As in other embodiments, the delivery device 1600 comprises first and second delivery cams 1602, 1604 respectively connected to each of the struts 1510, 1520. The first and second delivery cams 1602, 1604 are respectively pivotally connected to first and second internal connectors 1810, 1720 at a distal pivot 1603, 1605 and the first and second delivery cams 1602, 1604 are respectively pivotally connected to a delivery clevis 1608 at a proximal pivot 1806. Non-illustrated cam actuation connectors control the movement of the delivery cams 1602, 1604 with respect to one another (e.g., opening and closing as shown in FIGS. 9 and 10). A beneficial characteristic arises with the first and second distal pivots 1603, 1605. By allowing the first and second internal connectors 1810, 1720 to pivot freely about a small angle (e.g., between >0° and approximately 60°, in particular, between approximately 20° and approximately 40°, particularly, approximately) 30°, the internal connectors 1810, 1720 permit easy self-alignment so that when the second internal connector 1720 is inserted (as it is longer), the first internal connector 1810 can be pivoted as desired with the second internal connector 1720 remaining relatively still.

FIG. 18 illustrates both the step of final disconnection of the struts 1510, 1520 from the delivery device 1600 and the step of connecting the struts 1510, 1520 to the delivery device 1600. The progression from FIG. 18 to FIG. 20 illustrates how the struts 1510, 1520 are connected respectively to the first and second internal connectors 1810, 1720. As indicated by the different numerals, the first internal connector 1810 differs from the first internal connector 1610, 1710 and the first internal connector interface 1912 differs from the first internal connector interfaces 1512, 1532. In the exemplary embodiment of FIGS. 18 to 20, the first and second internal connector interfaces 1912, 1542 are different from one another. The second internal connector interface 1542 is in the form of a cylindrical, blind hole. The second internal connector interface 1542, therefore, forms a guide into which the second internal connector 1720 inserts. When fully inserted, the second internal connector 1720 rests slidably within the second internal connector interface 1542. In contrast, the first internal connector 1810 is an assembly comprising a hollow tubular shell 1812 housing therein a locking plunger 1814 and a bias device 1716 connected to the proximal end of the plunger 1814 and grounded at a non-illustrated proximal position within the tubular shell 1812 and adjacent or inside the first delivery cam 1602. A lock control cord 1816 is fixed to the proximal end of the locking plunger 1814 on one end and is connected to the lock/unlock controller 2010 at the handle 2000 of the delivery device 1600. When actuated, the lock/unlock controller exerts a force on the lock control cord 1816 to move the plunger 1814 proximally within the tubular shell 1812 against the force of the bias device 1716, which in the exemplary embodiments shown is a spring. The tubular shell 1812 is cross-sectioned in FIGS. 18 to 20 so that the plunger 1814 and the bias device 1716 is visible in those figures.

In this exemplary embodiment, the struts 1510, 1520 have respective internal connector interfaces 1912, 1542, here substantially in the form of cylindrical, blind holes. The first internal connector 1810 is an assembly comprising the tubular shell 1812, the locking plunger 1814, the bias device 1716, the lock control cord 1816, and a bent cord lock 1818. The second internal connector 1720 is a cylindrical shaft having an external shape corresponding to the second internal connector interface 1542 for mating therein. Here, the external shapes of the first and second internal connectors 1810, 1720 are similar, a cylinder having a circular cross-section and a rounded tip. However, the shapes of the two connectors 1810, 1720 can be different, for example, one circular and one polygonal in cross-section.

If the second internal connector 1720 was simply inserted within the second internal connector interface 1542, then it would be possible for the second internal connectors 1720 to slip off. To retain the struts 1510, 1520 on the delivery clevis 1608, the first internal connector 1810 comprises the bent cord lock 1818, here in the exemplary form of a bent wire. The bent wire is formed from a deformable material (e.g., Nitinol or another NiTi alloy) that acts as a "one-way" catch. The catch is deemed one-way because it allows easy insertion of the first internal connectors 1810 into the first internal connector interface 1912 (the catch bends out of the way for insertion) but resists removal of the first internal connectors 1810 out from the first internal connector interface 1912 until a given amount of force is overcome. More specifically with regard to the progression from FIG. 18 to FIG. 20, for removable capture of the clip onto the delivery device 1600, the first and second internal connectors 1810, 1720 are slid into the first and second internal connector interfaces 1912, 1542. In FIG. 19, the internal connectors 1810, 1720 are in an intermediate inserted position. Here, the tubular shell 1812 is within the first internal connector interface 1912 sufficient to place the bent cord lock 1818 just proximal of a first entrance 1914 of the first internal connector interface 1912. A desirable exemplary shape of the first and second entrances 1914, 1524 is conical. A conical shape of the entrances 1914, 1524 is desirable to enable the user to insert the internal connectors 1810, 1720 into the internal connector interfaces 1912, 1542 and to allow the internal connectors 1810, 1720 to enter therein even if the central axes thereof are slightly out of alignment with the central axes of the internal connector interfaces 1912, 1542.

The first internal connector interface 1912 comprises a lock orifice 1916. As the tubular shell 1812 is inserted further into the first internal connector interface 1912, the bent cord lock 1818 is deformed (e.g., to collapse the NiTi wire) within the first internal connector interface 1912 (this collapse is not illustrated). With further insertion of the internal connectors 1810, 1720 to align the bent cord lock 1818 with the lock orifice 1916, the bent cord lock 1818 springs back from its deformation within the lock orifice in a final insertion position of the internal connectors 1810, 1720, which is shown in FIG. 20. Deformability of the bent cord lock 1818 is set so that the surgeon can feel removal of the first internal connector 1810 from the delivery device 1600 but is not too strong to cause significant movement of the struts 1510, 1520 on tissue that is compressed between the opposing tissue contacting surfaces of the struts 1510, 1520 during implantation. As set forth above, a reason to lock the struts 1510, 1520 onto the delivery device 1600 is to prevent the clip 1500 from watermelon seeding off of the delivery device 1600. One of the significant benefits to having a self-locking connection between the delivery device 1600 and the struts 1510, 1520 is that the user does not need to actuate anything at the proximal end of the delivery device (for example, pulling on a trigger or sliding a slide) to cause locking of the clip 1500 on the delivery device 1600, which is especially beneficial during recapture for re-implantation. Simply put, there is an automatic locking of the struts 1510, 1520 onto the delivery device 1600 merely by sliding the internal connectors 1810, 1720 into the struts 1510, 1520.

Finally, FIG. 20 shows a locked state of the clip 1500 where the first internal connector 1810 is inserted within the first internal connector interface 1912 to position the tubular shell 1812 sufficiently far to lock the bent cord lock 1818 in the lock orifice 1916. With the bent cord lock 1818 inserted within the lock orifice 1916, the first strut 1510 (and thereby the second strut 1520 connected thereto) is locked temporarily upon the delivery device 1600. In order to unlock the clip 1500 from the delivery device 1600, the operator/surgeon actuates the lock/unlock controller 2010 at the handle 2000 to exert a proximal force on the lock control cord 1816. This force is greater than the force exerted by the bent cord lock 1818 at the lock orifice 1916 and, thereby, unlocks the bent cord lock 1818. The features of the lock described and shown are merely exemplary and other forms of a locking connection are equally possible.

Various exemplary embodiments to lock a clip onto a delivery device have been described. Alternative embodiments include the configuration shown in FIGS. 72 to 74. In this exemplary embodiment, at least one of the internal connectors 7200 has a barb feature that engages a lock on the clip strut (e.g., 1510, 1520), which state is shown diagrammatically in FIG. 72. A non-illustrated jaw control is connected to the jaws with a minimum preload opening force on the first and second internal connectors 7200, engaging the barb feature on the lock 7210. This barb-in-lock engagement substantially prohibits release of the clip until proper clip placement is achieved. Once the surgeon is satisfied with clip placement, the jaw control may relax the opening preload on the first and second internal connectors 7200, as shown diagrammatically in FIG. 73, thereby releasing the barb from the lock 7210 and allowing detachment of the clip from the end effector as shown diagrammatically in FIG. 74.

Further exemplary embodiments of a clip lock to a delivery device include expanding collets, balloons, and scarf cuts. In an expanding collet or balloon embodiment the internal connector comprises an expanding, opening, or otherwise shape-altering structure that engages the internal connector interface by friction or by intimate intercomponent mechanical interference. This is not limiting friction to soft surfaces, the internal connector interface or the internal connector can have locking features that engage upon expansion. In one exemplary embodiment, the internal connector is an expanding pin that flairs open inside of the internal connector interface, providing sufficient resistance to detachment of the clip. In another exemplary embodiment, the internal connector is a balloon that can be inflated inside the internal connector interface, providing sufficient resistance to detachment of the clip. In yet another exemplary embodiment, the internal connector has a scarf joint. When inside the internal connector interface, the lock control cord can be actuated, causing a lateral shift in the internal connector scarf joint, resulting in sufficient resistance to detachment of the clip. Another exemplary embodiment for the locking features includes use of magnetic materials. In this exemplary embodiment, the internal connector has an internal magnet attached to the lock control cord, biased distally by a biasing member (e.g., a spring as in FIGS. 12 to 20), and the clip strut has a magnetic component or feature inside the internal connector interface. The magnet of the internal connector then imposes a magnetic force on the magnetic component or feature inside the internal connector interface, providing sufficient resistance to detachment of the clip without user action. Actuating the lock control cord retracts the internal magnet, sufficiently weakening the magnetic force between the magnet and the magnetic component, thereby enabling detachment of the clip. In yet another exemplary embodiment, the connectors may engage the outer surfaces of the clip strut. Both locking features and connector interfaces could then be internal and/or external.

Figure 24:
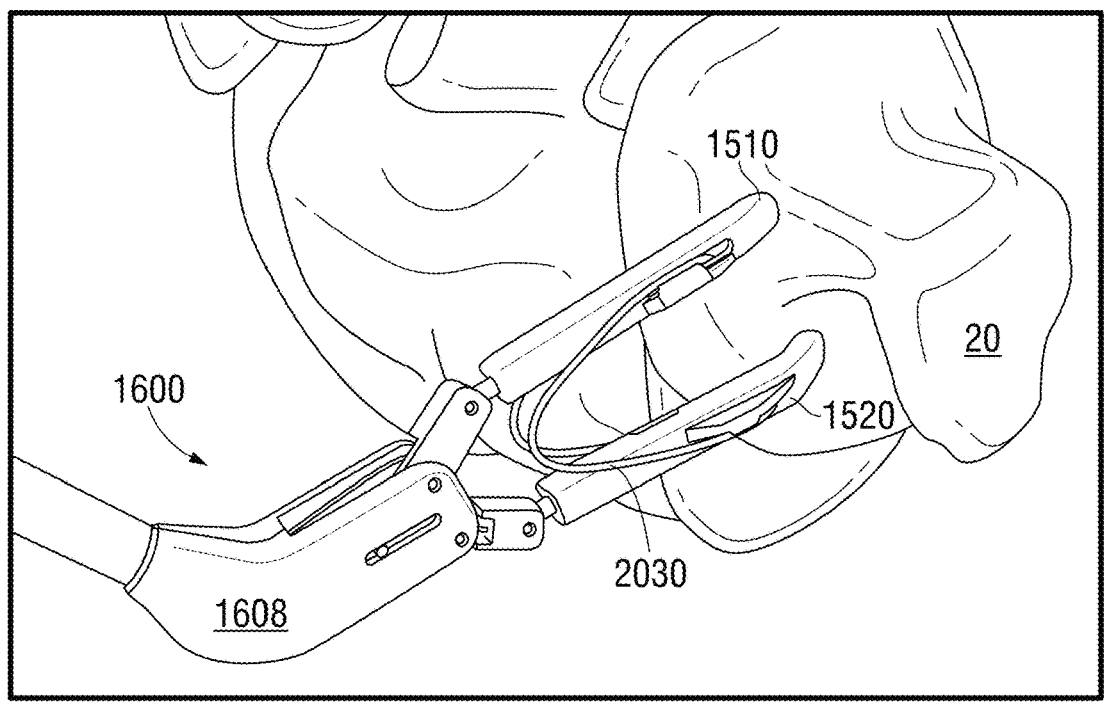
FIG. 24 is a fragmentary, perspective view of the end effector and clip of FIG. 22 in a clip-opened state adjacent the LAA.
Figure 25:
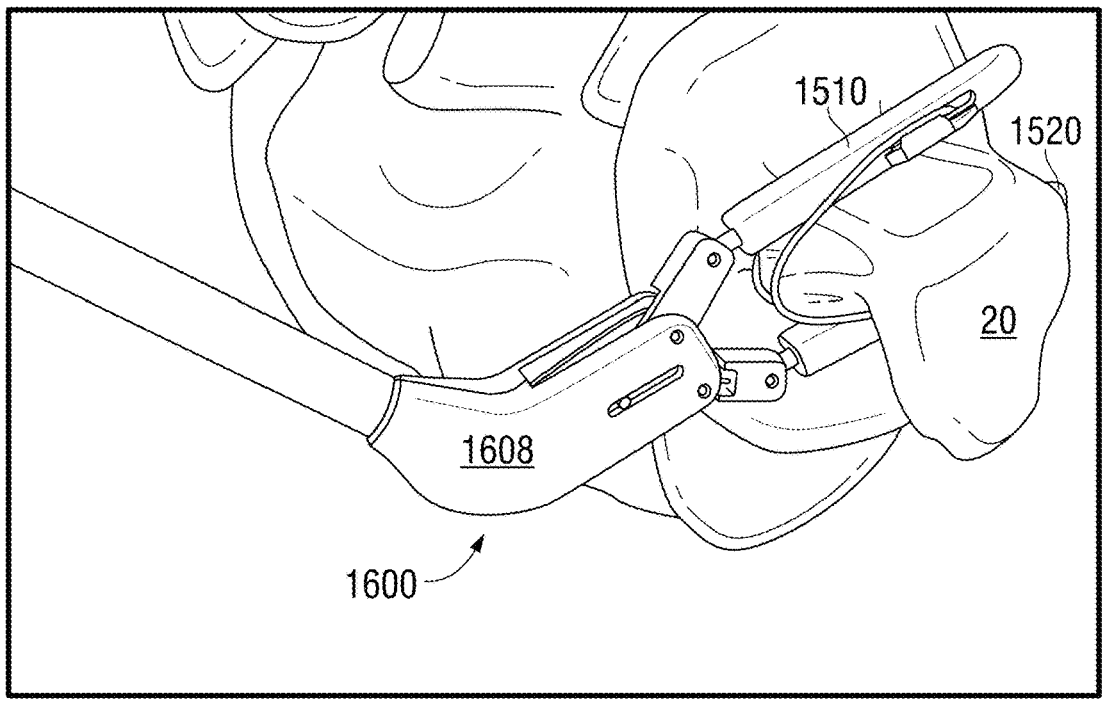
FIG. 25 is a fragmentary, perspective view of the end effector and clip of FIG. 22 in the clip-opened state surrounding the LAA.
Figure 26:
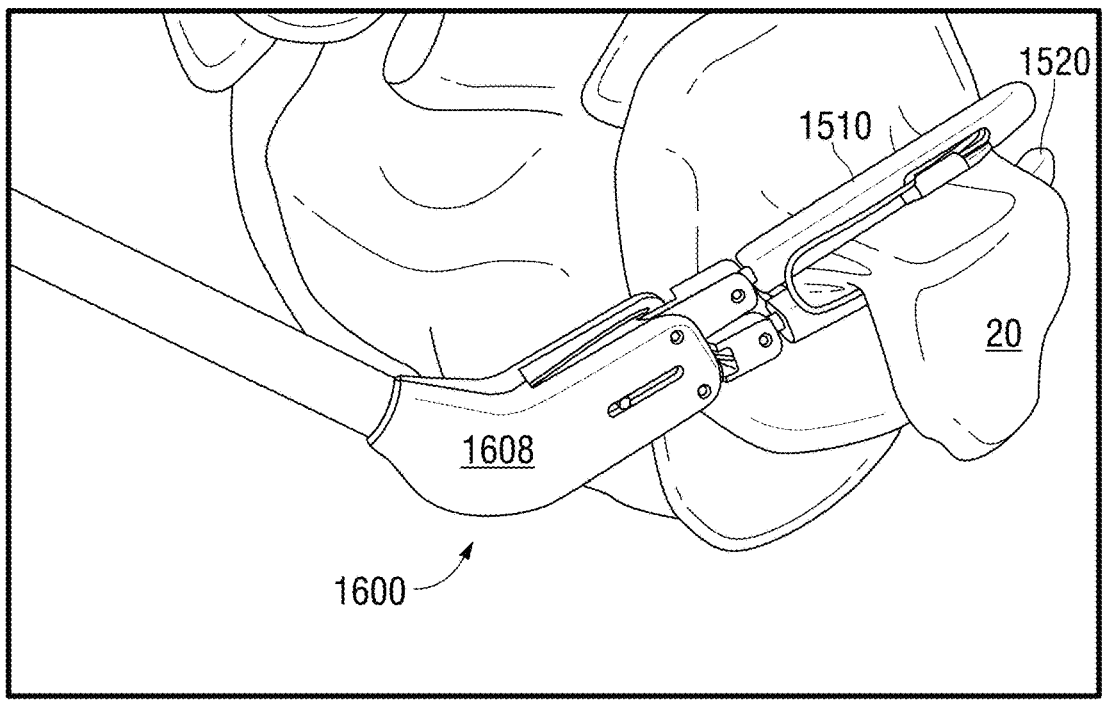
FIG. 26 is a fragmentary, perspective view of the end effector and clip of FIG. 22 in the clip-closed state surrounding the LAA.
Figure 27:
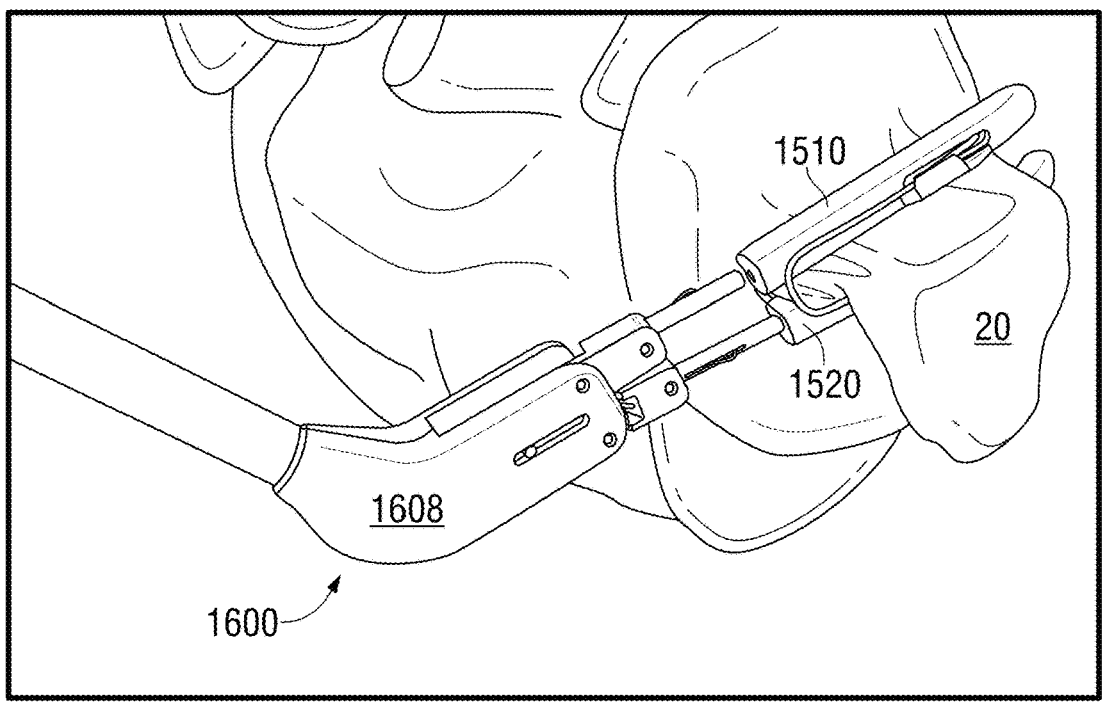
FIG. 27 is a fragmentary, perspective view of the end effector and clip of FIG. 22 with the clip partially deployed in a clip-installed state surrounding the LAA.
Figure 28:
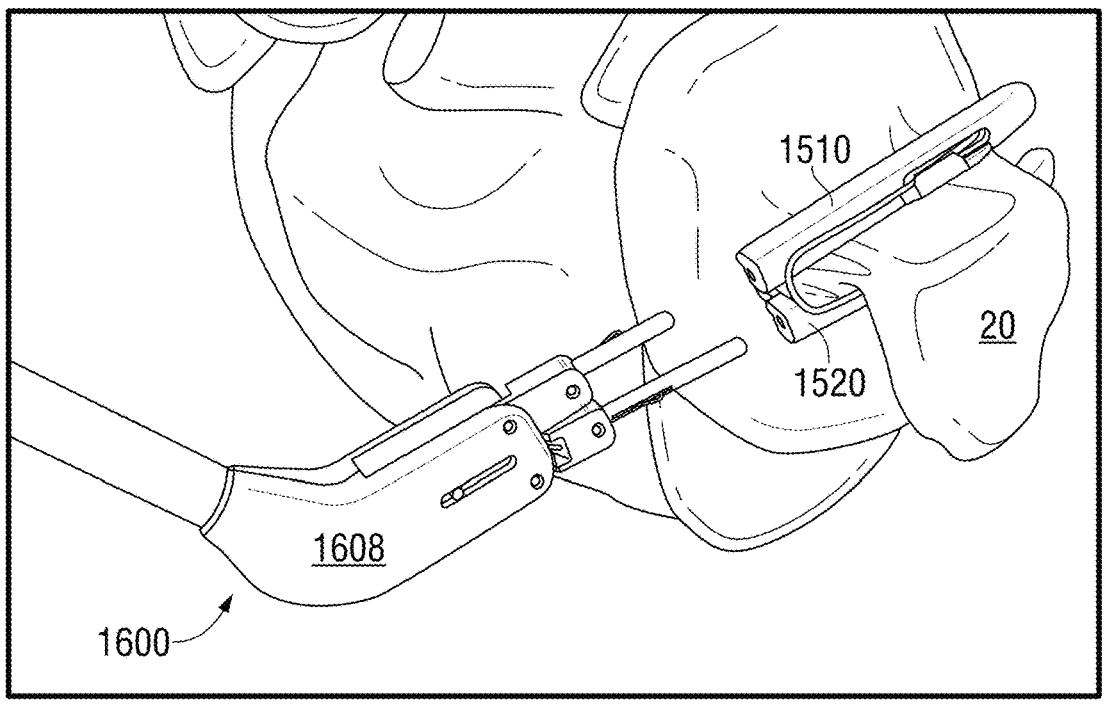
FIG. 28 is a fragmentary, perspective view of the end effector and clip of FIG. 22 with the clip deployed in a clip-installed state surrounding the LAA.

FIGS. 23 to 28 illustrate an exemplary embodiment of the clip 1500 attached to the end effector of the delivery device 1600 in various implantation states on a LAA 20. In FIG. 23, the clip 1500 is closed and is approaching the implantation site at the base of the LAA 20. In FIG. 24, the clip 1500 is opened and is approaching the implantation site at the base of the LAA 20. In FIG. 25, the clip 1500 is open and surrounds the base of the LAA 20. In FIG. 26, the clip 1500 is closed down upon the base of the LAA 20 but remains attached to the delivery device 1600. In FIG. 27, the clip 1500 has been released from the delivery device 1600 and is closed upon the base of the LAA 20 but the internal connectors still remain within the internal connector interfaces of the struts 1510, 1520. Finally, in FIG. 28, the clip 1500 is implanted on the base of the LAA 20 and the delivery device 1600 is completely free from the clip 1500. If implantation is desirable, the procedure is over. However, if a different implantation orientation is desired, the internal connectors can be re-inserted into the internal connector interfaces and the clip 1500 can be removed and repositioned on the LAA 20. These steps can be repeated until a satisfactory implantation of the clip 1500 is achieved.

Figure 29:
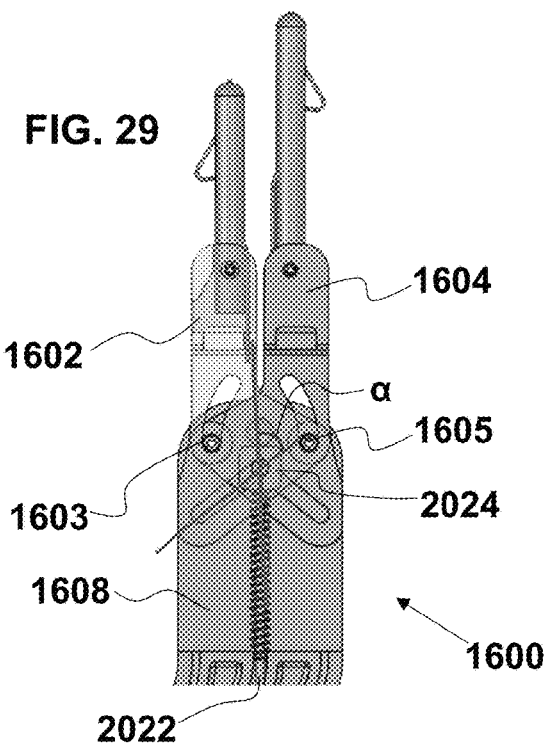
FIG. 29 is a fragmentary, cross-sectional and partially transparent view of an end effector of the device of FIG. 3 with the jaws in a closed state.
Figure 30:
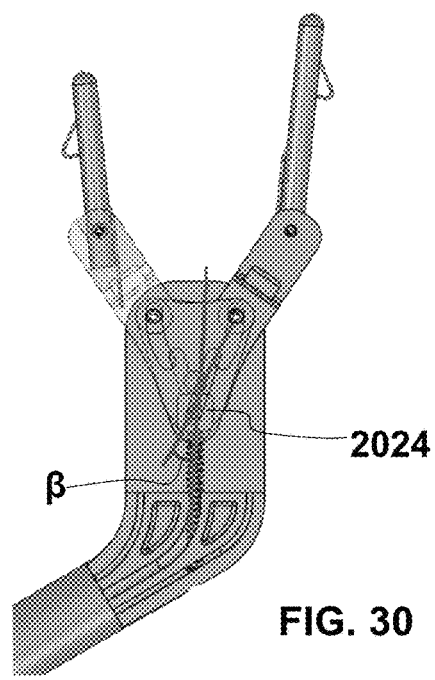
FIG. 30 is a fragmentary, cross-sectional and partially transparent view of an end effector of the device of FIG. 3 with the jaws in an open state.
Figures 31, 32, 33:
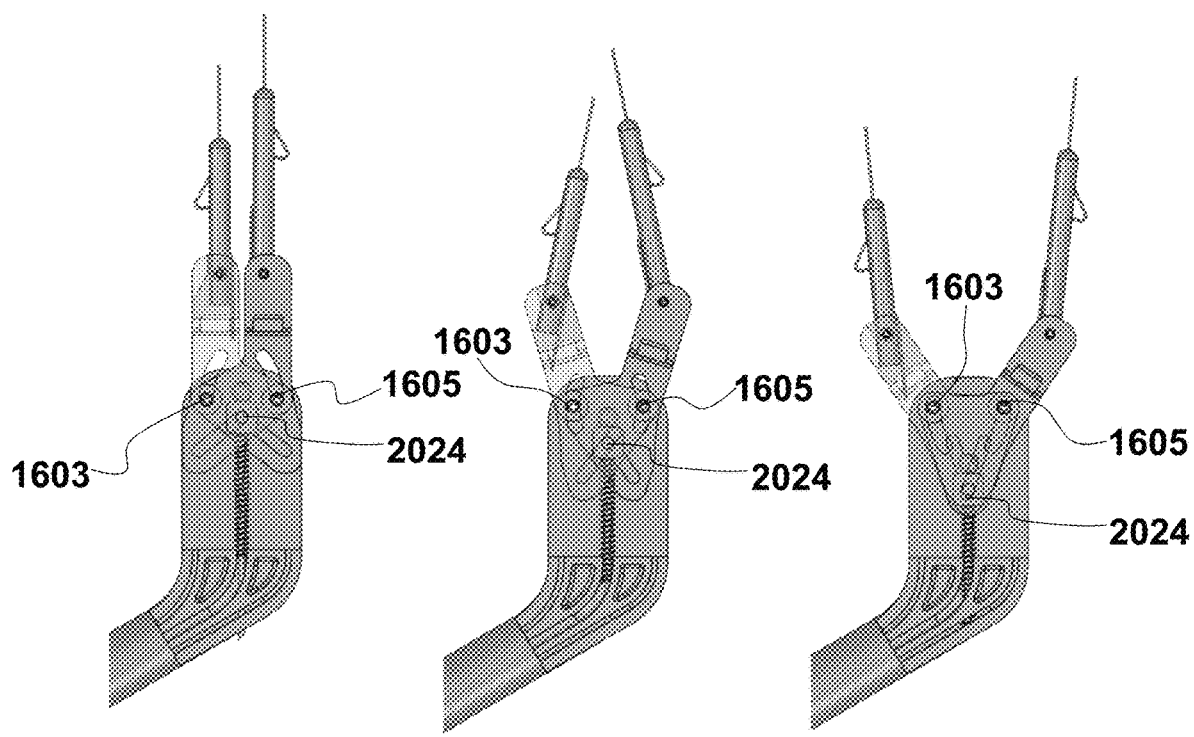
FIG. 31 is a fragmentary, cross-sectional and partially transparent view of an end effector of the device of FIG. 3 with the jaws in a closed state.
FIG. 32 is a fragmentary, cross-sectional and partially transparent view of an end effector of the device of FIG. 3 with the jaws in an intermediate open state.
FIG. 33 is a fragmentary, cross-sectional and partially transparent view of an end effector of the device of FIG. 3 with the jaws in an open state.
Figure 34:
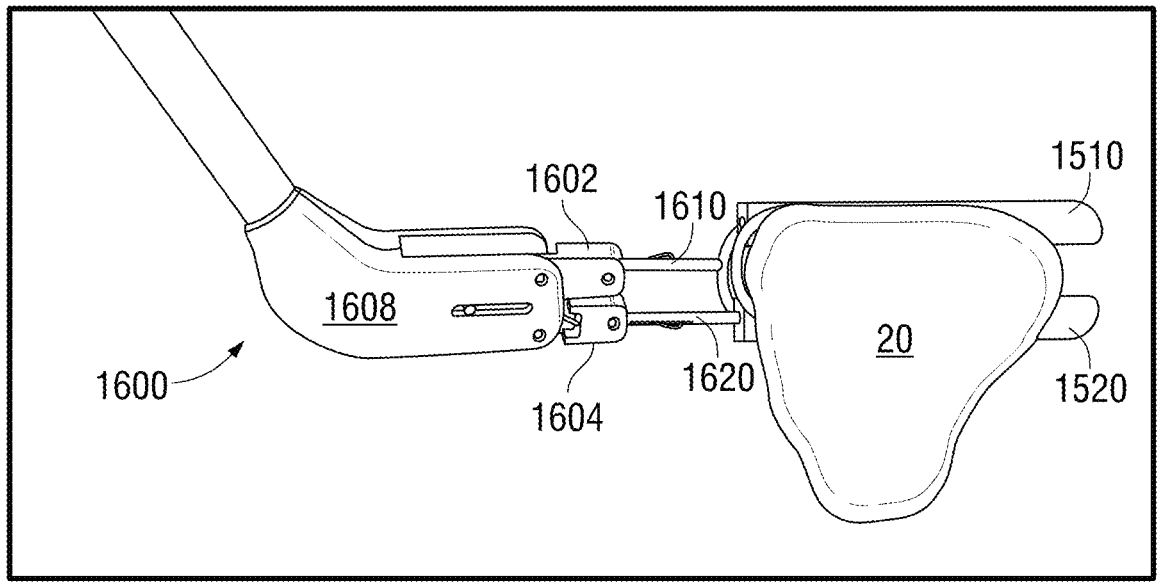
FIG. 34 is a fragmentary, perspective view of the clip of FIG. 3 implanted on a representative LAA and the device of FIG. 3 adjacent the clip with a first internal connector outside a first strut of the clip and a second internal connector slightly within a second strut of the clip.
Figure 35:
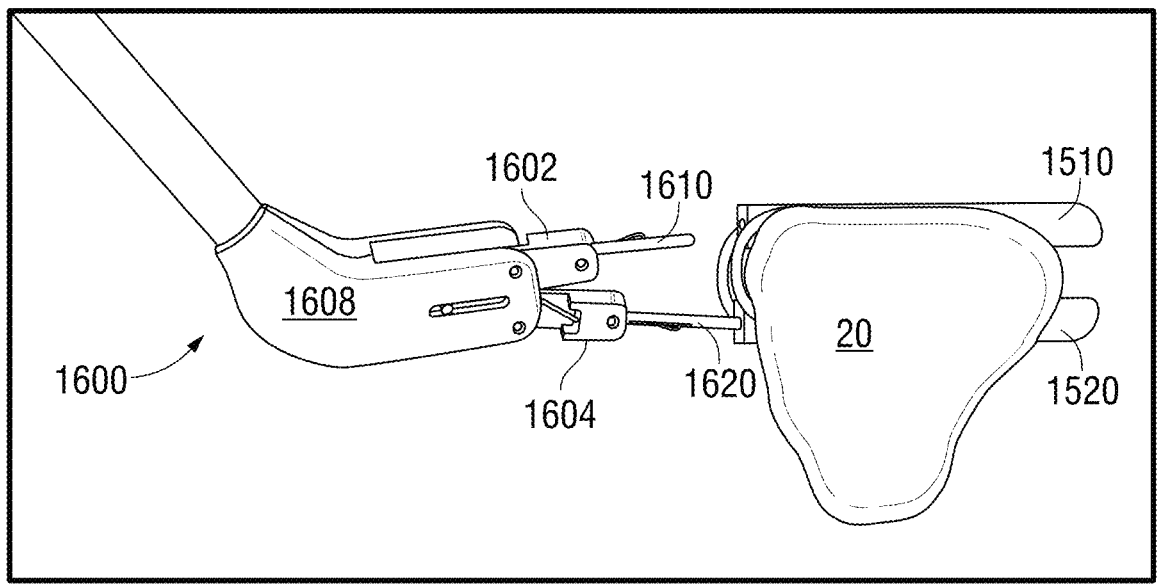
FIG. 35 is a fragmentary, perspective view of the clip and device of FIG. 34 with the second internal connector slightly within a second strut of the clip and the clevis rotated to move the first internal connector towards the entrance to the first strut of the clip.
Figure 36:
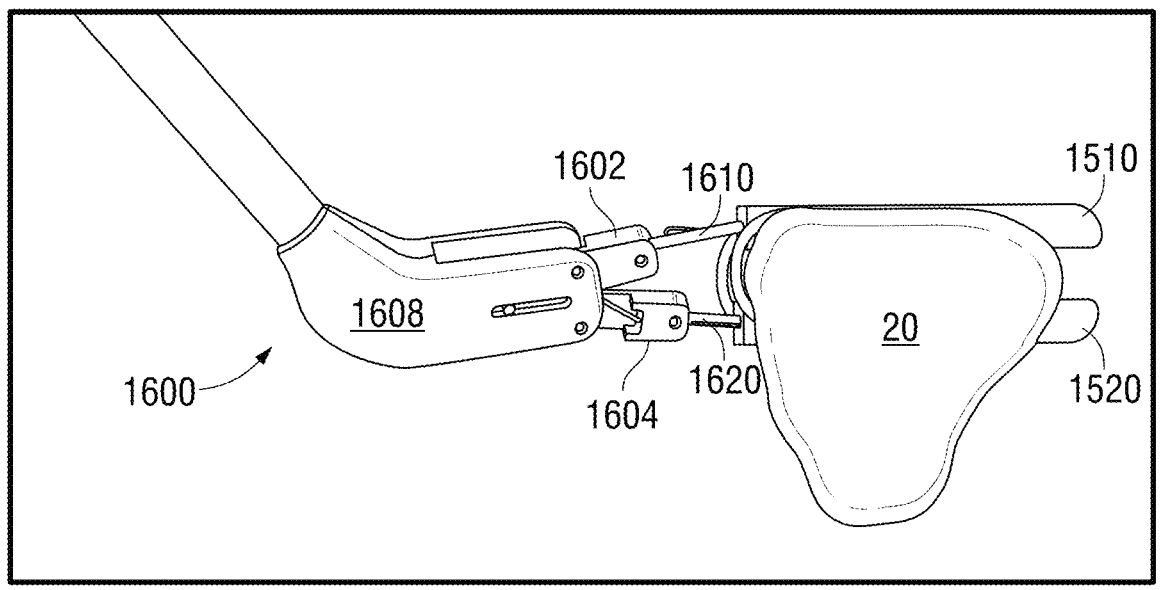
FIG. 36 is a fragmentary, perspective view of the clip of FIG. 3 implanted on a LAA and the device of FIG. 3 having a first internal connector slightly within a first strut of the clip and a second internal connector slightly within a second strut of the clip.
Figure 37:
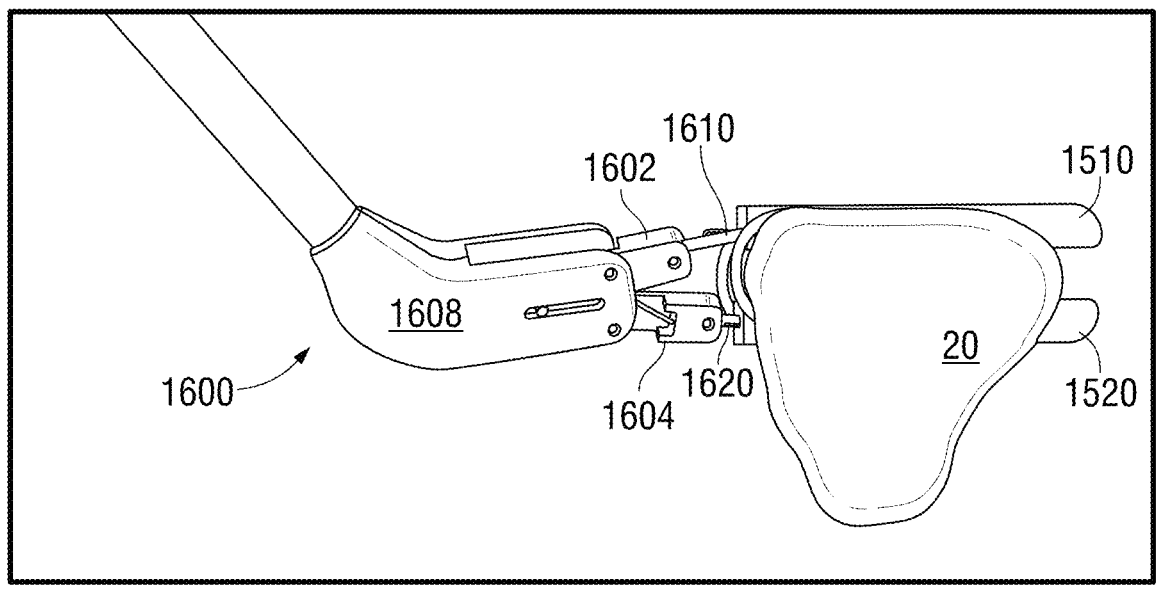
FIG. 37 is a fragmentary, perspective view of the clip of FIG. 3 implanted on a LAA and the device of FIG. 3 having first and second internal connectors partially within respective struts of the clip.
Figure 38:
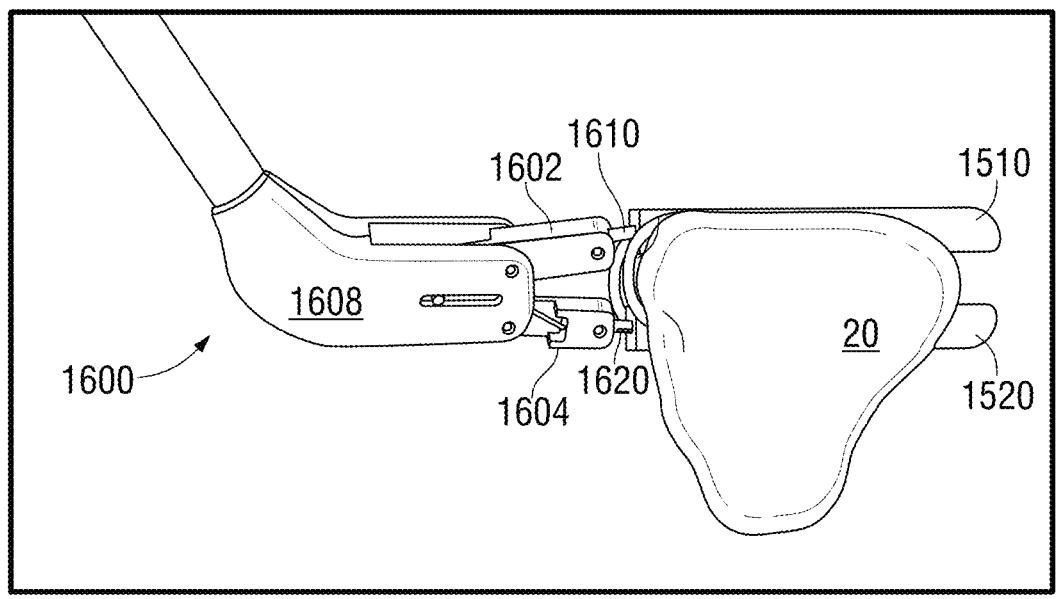
FIG. 38 is a fragmentary, perspective view of the clip of FIG. 3 implanted on a LAA and the device of FIG. 3 having first and second internal connectors locked within respective struts of the clip.

It is noted that recapture of the clip 1500 from the LAA 20 can pose some difficulty for the surgeon as the struts 1510, 1520 of an implanted clip 1500 will not only be separated from one another (as compared to the touching parallel position of the struts 1510, 1520 shown, for example, in FIGS. 18 to 21) but the struts 1510, 1520 may not also be parallel to one another (for example, when the tissue clamped between the struts 1510, 1520 is not uniform). Having both the spacing and the non-parallelism is common after implantation of the clip 1500. The embodiments of the delivery device 1600 overcome this obstacle with the exemplary configurations of the cams 1602, 1604, the internal connectors 1610, 1620, 1710, 1720, 1810, and the pivots 1603, 1605, 1606, 1607, 1806 connecting these structures and allowing them to move with respect to one another. To explain how these parts allow the internal connectors to independently move to align with internal connector interfaces in the struts, reference is made to FIGS. 29 to 33. The cam slots within the delivery cams 1602, 1604 are shaped and are spaced from the pivots 1603, 1605 to provide less mechanical advantage in the beginning of the stroke where the two cams 1602, 1604 are starting to spread apart and to provide significantly more mechanical advantage in the middle and end of the stroke where the two cams 1602, 1604 spread apart further. More particularly as shown in FIG. 29, the trigger 2020 is actuated to start the jaw-opening actuation of the cams 1602, 1604. This trigger 2020 is connected through a jaw control cord 2022 to a cam block 2024 that, when moved proximally in this exemplary embodiment, imparts a force to the cams 1602, 1604 about the pivots 1603, 1605 at an angle $\alpha$. As this angle is relatively large, the longitudinal force is relatively small. However, as the trigger 2020 is actuated further to move the cam block 2024 further proximally, the force imparted to the cams 1602, 1604 about the pivots 1603, 1605 is now at an angle $\beta$. As this angle is relatively small, most of the mechanical advantage is in the longitudinal direction and, therefore, the longitudinal force is relatively large. (The progression from a closed state to an intermediate open state to an open state is illustrated in FIGS. 31 to 33.) As such, in the closed position when the angle is large (e.g., a) any lateral force acting on the distal tip of either of the connectors 1610, 1620, 1710, 1720, 1810 can move the distal tip relatively easily. In other words, a user placing their finger on the tip of one of the connectors 1610, 1620, 1710, 1720, 1810 can pivot the connector and the cam about the pivot relatively easily (this feature is illustrated in FIGS. 34 to 38 explained below). In comparison, as the cams 1602, 1604 are further rotated about the pivots 1603, 1605, the amount of force to move the tip laterally increases substantially. Another way of describing this function of the delivery device 1600 is that the first opening motion of the cams 1602, 1604 only has to open the proximal end of the struts (see FIG. 32) and, therefore, only half of the overall load is required for this opening portion. Accordingly, the tracks of the cams 1602, 1604 in which the actuation pin runs are configured so that the mechanical advantage is less at the beginning of motion where the load is less. In comparison, the mechanical advantage is greater at the end of the motion (see FIG. 33) where the loads are the greatest as the entirety of the struts 1510, 1520 are being separated. By having a low mechanical advantage in a first part of the motion, there is an ability to "backdrive" the system by applying a spreading force to the cams 1602, 1604. The force required to spread the cams 1602, 1604 is at its lowest when the cams 1602, 1604 are at their closest. This allows the operator to easily move the cams 1602, 1604 to match a width of the tissue that is disposed within the struts 1510, 1520 at the time of recapture. This can be accomplished by gross motion of the clevis 1608 away from the strut 1520 in which the longer connector 1620 had been engaged and towards the other strut 1510. Such motion is shown in the progression from FIG. 34 to FIG. 38. In FIG. 34, the clip 1500 is implanted on the base of the LAA 20 and removal and/or reimplantation is desired. Accordingly, the surgeon inserts the distal tip of the second internal connector 1620 into the strut 1520. At this point, the surgeon can use this as a fulcrum to move the clevis 1608 with gross motion to align the first internal connector 1610 with the first internal connector interface 1512 of the first clip strut 1510. As shown in FIG. 35, the surgeon has applied a force (upwards in FIG. 35) to pivot the second internal connector 1620 and the second delivery cam 1604 clockwise, thereby moving the distal tip of the second internal connector 1620 away from the distal tip of the first internal connector 1610. In this example, the struts 1510, 1520 are purposefully non-parallel. Accordingly, once the second internal connector 1620 is seated in the strut 1520, the first internal connector 1610 is not aligned with the axis of the first internal connector interface 1512. With clockwise gross motion of the delivery device 1600 shown in FIG. 36, the surgeon rotates the clevis 1608, thereby maneuvering the distal tip of the first internal connector 1610 into alignment with the internal connector interface of the first clip strut 1510 (see FIG. 37). The surgeon next pushes the clevis 1608 distally towards the struts 1510, 1520 and the internal connectors 1610, 1620 naturally slide into the respective internal connector interfaces 1512, 1522 with rotation of the parts about the various pivots 1603, 1605, 1606, 1607. With further distal movement of the clevis 1608 as shown in FIG. 38, the internal connectors 1610, 1620 fully enter the respective internal connector interfaces 1512, 1522 and the connector locks 1614, 1624 lock the delivery device 1600 onto the struts 1510, 1520. With this locking, the clip can be opened and either removed or repositioned on the LAA 20 as desired by the surgeon.

Figure 39:
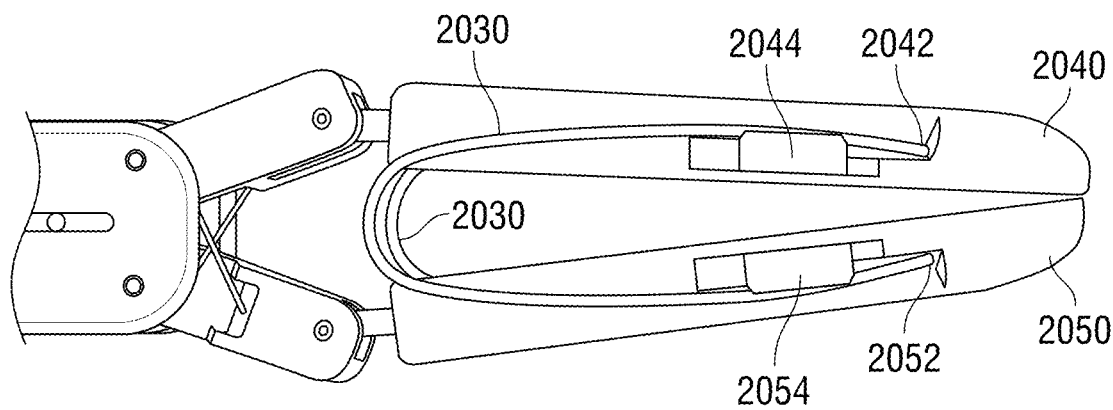
FIG. 39 is a fragmentary, perspective view of a portion of the end effector and the clip of FIG. 3 with the clip in a partially opened state.
Figure 40:
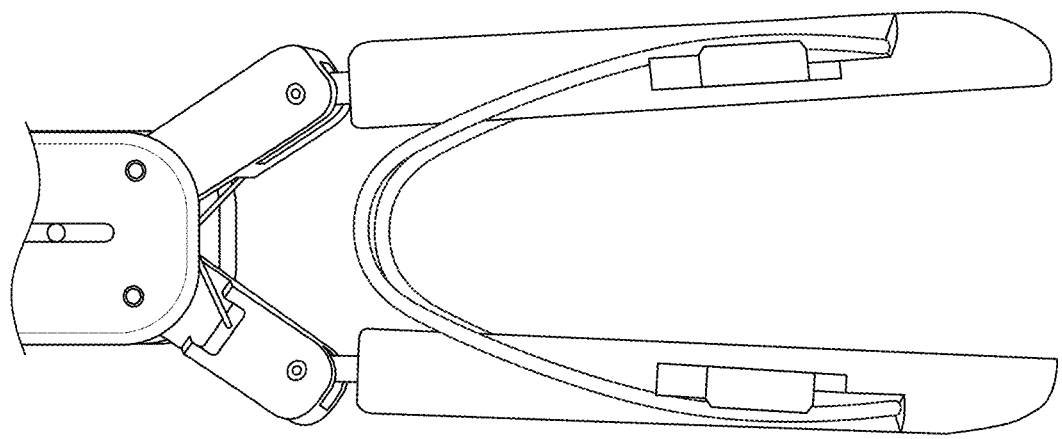
FIG. 40 is a fragmentary, perspective view of a portion of the end effector and the clip of FIG. 3 with the clip in an opened state.

In another exemplary embodiment of a clip, with reference to FIGS. 39 and 40, biasing members 2030 can be attached to the struts 2040, 2050 through geometric features, such as a 90-degree bend in the spring that engages a hole 2042, 2052 and an associated overhang 2044, 2054 in the strut. The overhang 2044, 2054 overlaps the hole 2042, 2052 such that the biasing spring 2030 would need to be expanded for insertion such that, while applying a biasing load, the biasing spring 2030 will continue to be retained by the overhang 2044, 2054. This enables a torsionally rigid connection between the biasing member 2030 and the strut 2040, 2050 without the use of a secondary crimp or mechanical retaining attachment, lowering part count and cost and simplifying the implant. Such a configuration reduces materials, part count, and failure modes.

The exemplary configurations shown in FIGS. 41 to 52 illustrate another exemplary embodiment of a clip 2100. FIGS. 41 to 52 illustrate the clip 2100 with a bias device 2130 present on both the top and bottom of the struts 2110, 2120. As used herein, top and bottom (and upper and lower) are used only to distinguish opposite sides of the struts 2110, 2120. Use of top and bottom does not mean that a top side of one of the struts 2110, 2120 must necessarily be on top of a structure on which it is placed. In one example for implantation of the clip 2100 on a LAA, the bottom side of the struts 2110, 2120 can rest on the surface of the heart adjacent the left atrium while the top side faces away from the left atrium and along and/or against some tissue of the LAA that extends away from the heart above the clip 2100. The first, second, third, and fourth bias anchors or bias device connectors 2114, 2124, 2115, 2125 are integral to the struts 2110, 2120 in this exemplary embodiment. The bias device 2130 is not fastened to the struts 2110, 2120 by an external device (such as a separate clip or anchor) but is, instead, wrapped around various securing points on the struts 2110, 2120 including the first through fourth bias connectors 2114, 2124, 2115, 2125. Thus, the bias device 2130 can be referred to as being self-secured, meaning that there is no structure external to the struts 2110, 2120 required to secure the bias device 2130 to the struts 2110, 2120. In the exemplary embodiment, after being bent around the securing points on the struts 2110, 2120, the ends of the upper and lower bias devices 2130 are presented within bias ports 2112, 2122, 2113, 2123 on either side of each of the struts 2110, 2120. The bias ports 2112, 2122, 2113, 2123 can be seen in the cross-sections of FIGS. 42 and 43 and the plan views of FIGS. 44 and 45, for example.

Figure 42:
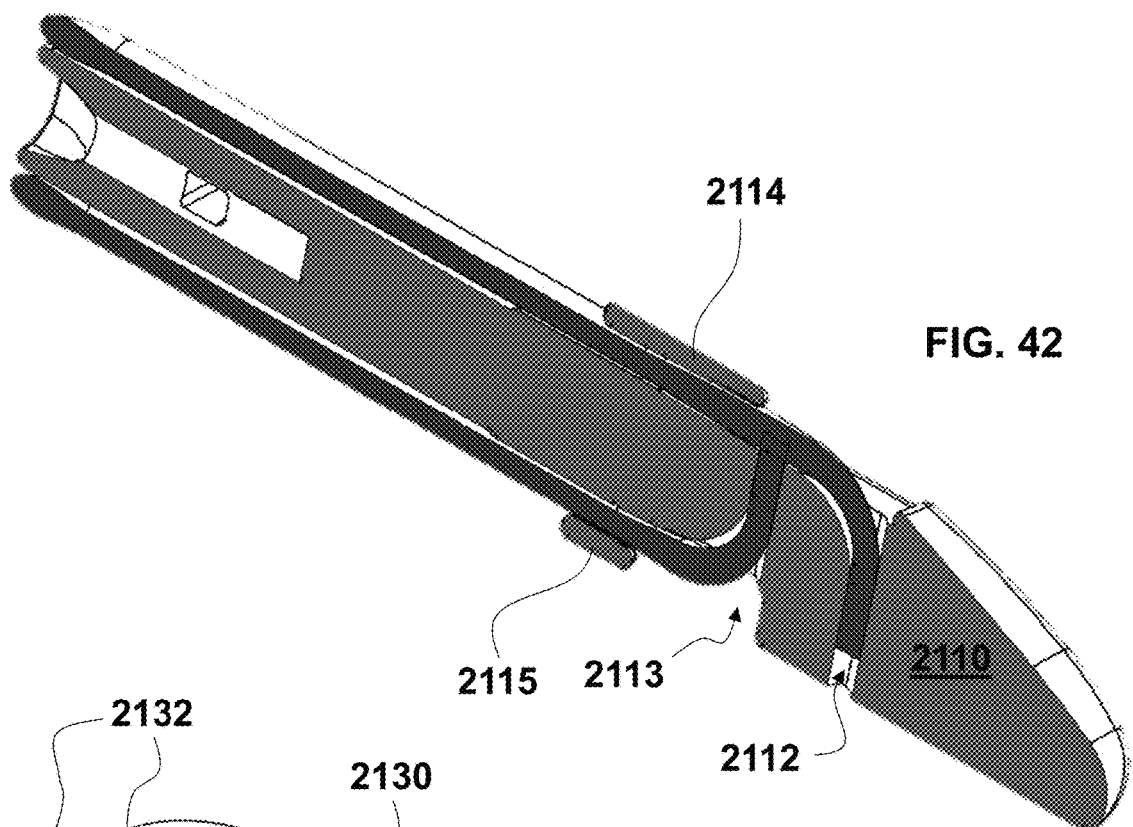
FIG. 42 is a perspective view of a longitudinally vertical cross-section of a first clip strut of the clip of FIG. 41 through upper and lower bias devices and through a first clip strut showing an interior hollow of the first clip strut for receiving a portion of a clip delivery device.
Figure 43:
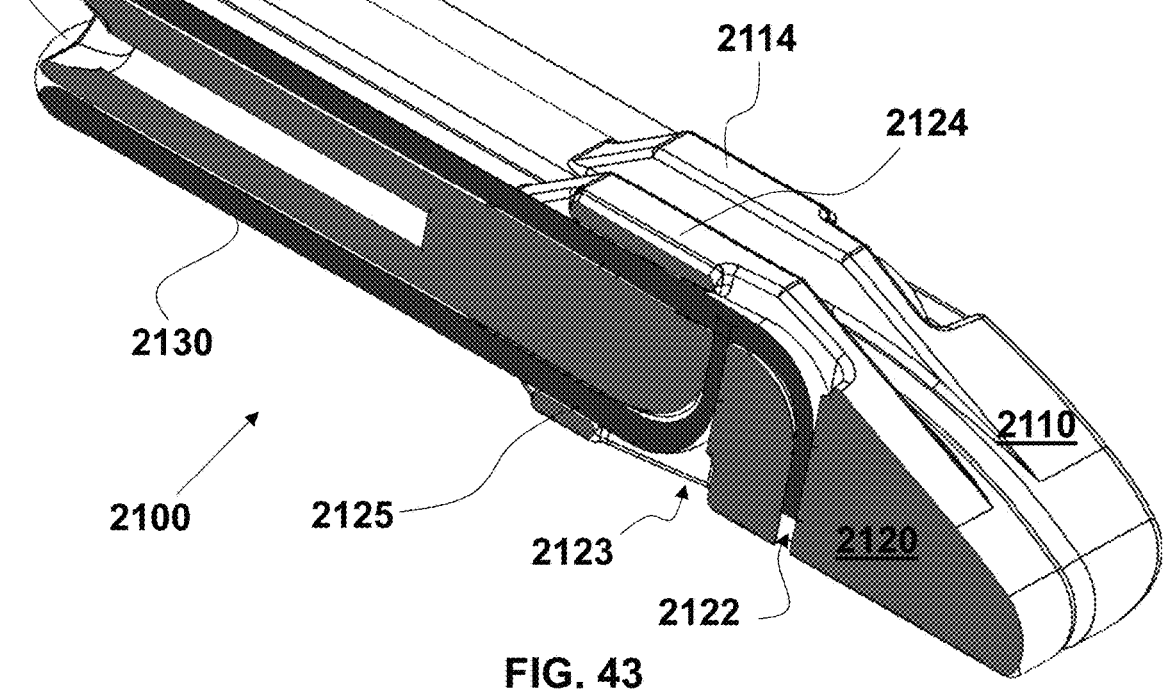
FIG. 43 is a perspective view of a longitudinally vertical cross-section of a second clip strut of the clip of FIG. 41 through the upper and lower bias devices and through the second clip strut showing an interior hollow of the second clip strut for receiving a portion of a clip delivery device.
Figure 44:
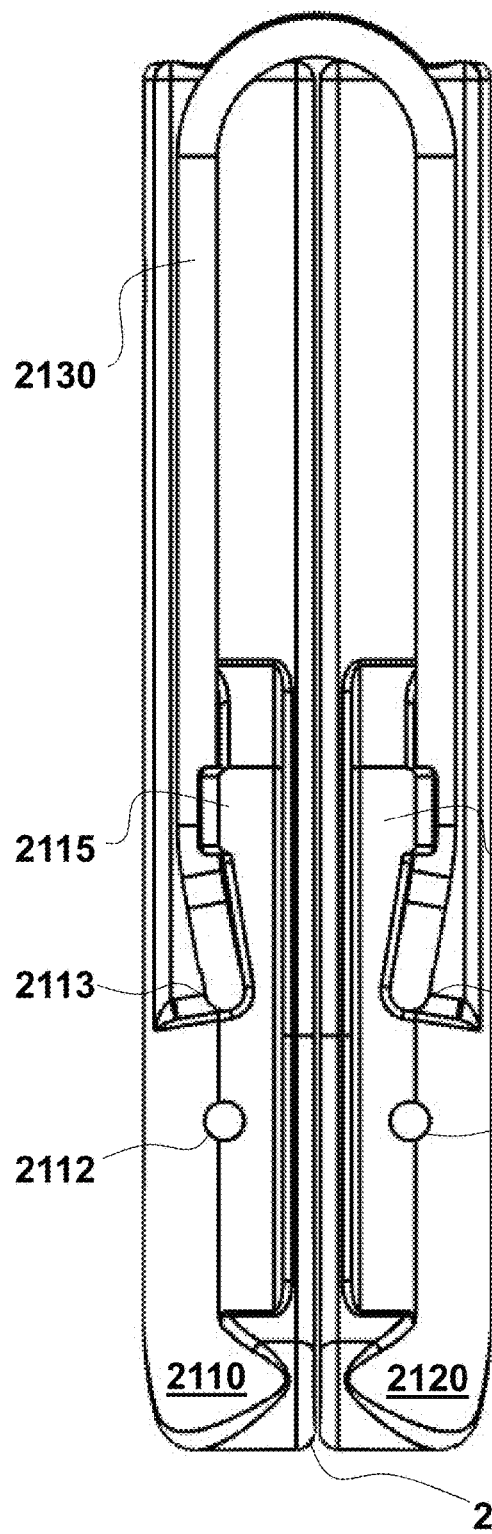
FIG. 44 is a bottom plan view of the clip of FIG. 41.
Figure 45:
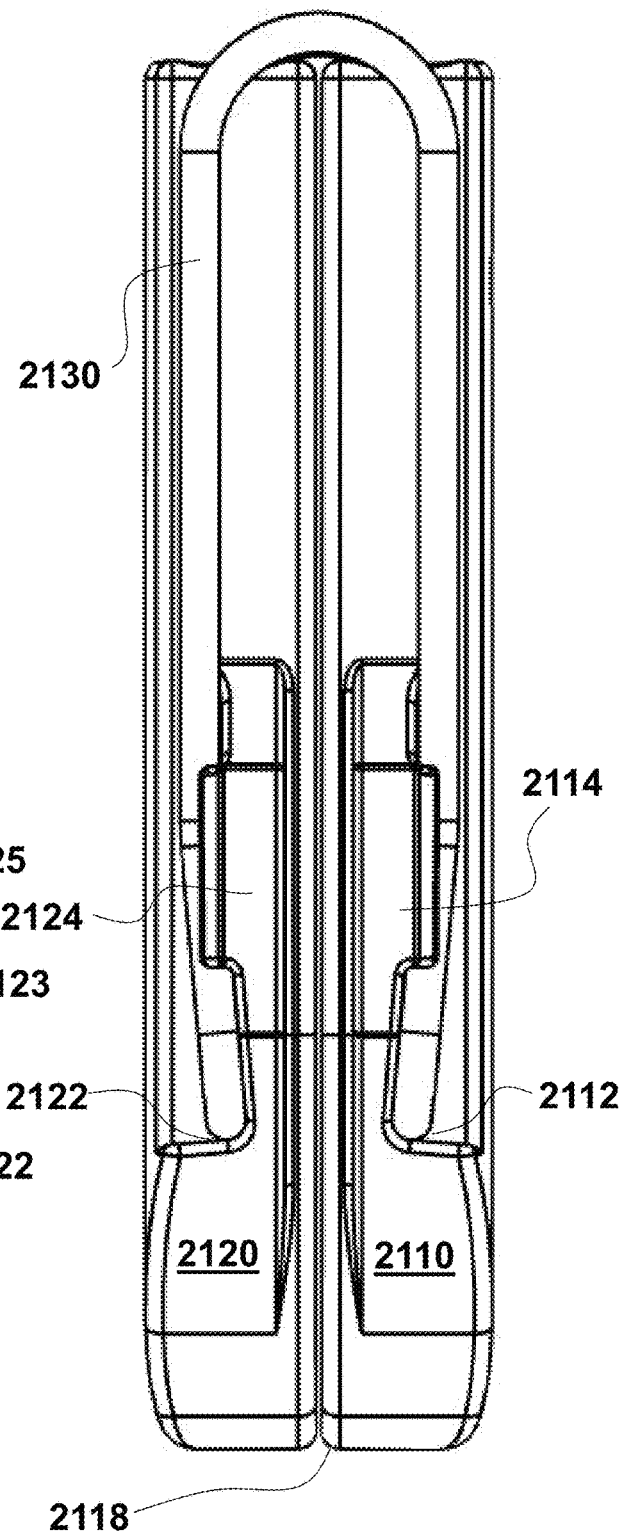
FIG. 45 is a top plan view of the clip of FIG. 41.
Figure 49:
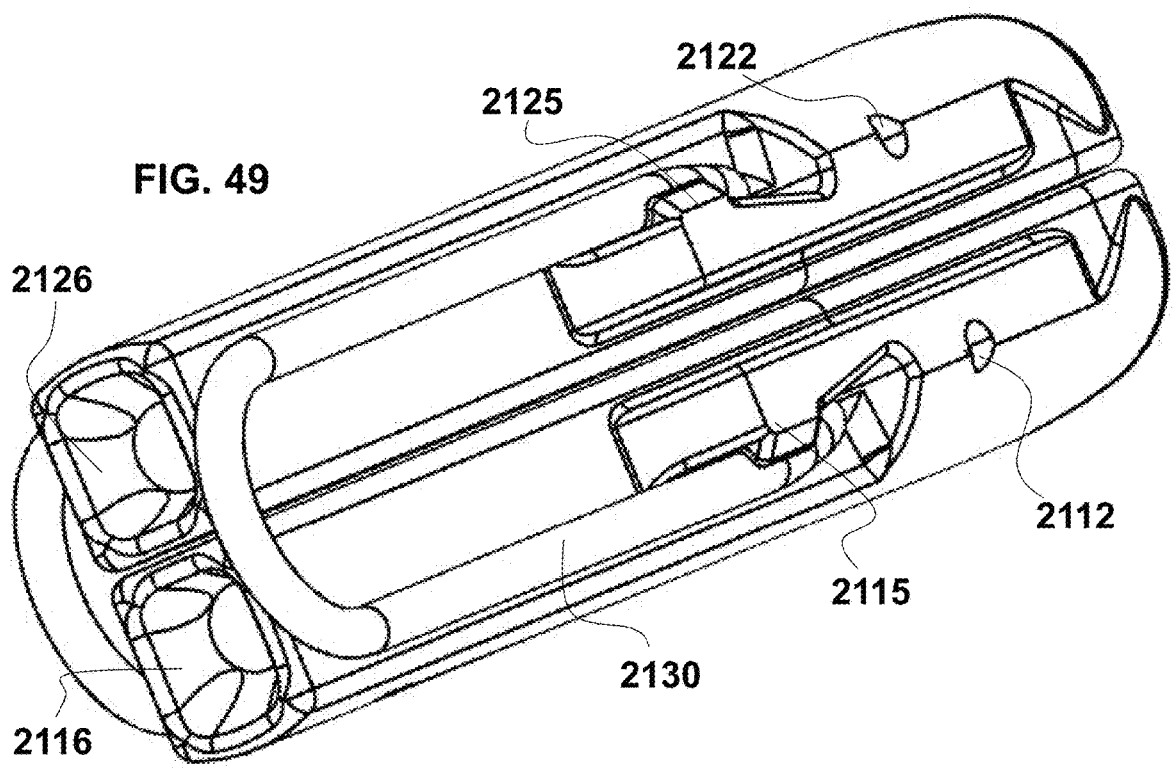
FIG. 49 is a perspective view from below a proximal end of the clip of FIG. 41.
Figure 50:
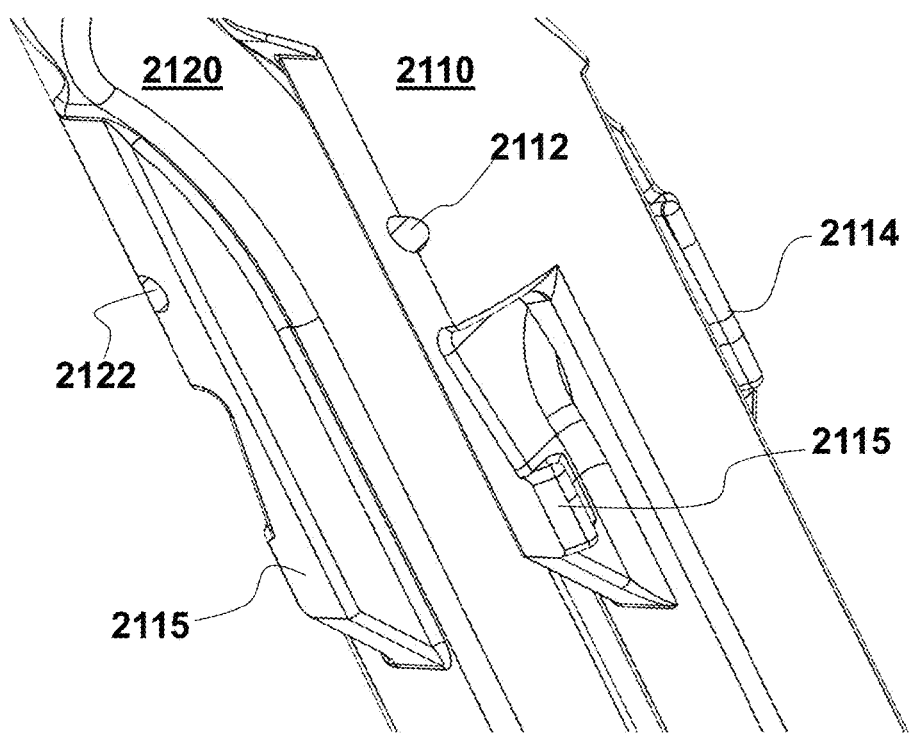
FIG. 50 is a fragmentary, perspective view from below an outer side of an intermediate portion of the first and second clip struts of the clip of FIG. 41 viewed from below an outer side of the first clip strut with the upper and lower bias devices removed.

With particular regard to FIG. 43, the upper bias device 2130, therefore, starts from the bias port 2112 in an upwards direction (with respect to FIG. 42) and bends approximately 90° in a longitudinal direction towards the proximal end of the clip 2100. The upper bias device 2130 then passes against and under the first bias connector 2114 and travels towards the proximal end of the first clip strut 2110. (The word against, as used herein, does not mean that the upper bias device 2130 must rest on top of the upper surface of the first clip strut 2110. The upper bias device 2130 can rest against that surface or can be at a distance therefrom (adjacent) or portions thereof can be touching with other portions thereof at a distance therefrom.) Either before the proximal end of the first clip strut 2110 or after the proximal end of the first clip strut 2110 (the latter of which example is shown), the upper bias device 2130 makes an approximate 180° bend 2132 in a transverse direction to leave a vicinity of the first clip strut 2110 and enter a vicinity of the second clip strut 2120. The upper bias device 2130 travels longitudinally away from the proximal end of the second clip strut 2120 in a distal direction and passes against and under the second bias connector 2124. The upper bias device 2130 then bends approximately 90° inwards into the bias port 2122 and terminates, as shown in FIGS. 43 and 44, within the bias port 2122.

The lower bias device 2130 starts from the bias port 2113 in a downwards direction (with respect to FIG. 42) and bends approximately 90° in a longitudinal direction towards the proximal end of the clip 2100. The lower bias device 2130 then passes against and under the third bias connector 2115 and travels towards the proximal end of the first clip strut 2110. Either before the proximal end of the first clip strut 2110 or after the proximal end of the first clip strut 2110 (the latter example of which is shown), the lower bias device 2130 makes an approximate 180° bend 2132 in the transverse direction to leave a vicinity of the first clip strut 2110 and enter a vicinity of the second clip strut 2120. The lower bias device 2130 travels longitudinally away from the proximal end of the second clip strut 2120 in a distal direction and passes against and under the fourth bias connector 2125. The lower bias device 2130 then bends approximately 90° inwards into the bias port 2123 and terminates, as shown in FIG. 43, within the bias port 2123.

Figure 51:
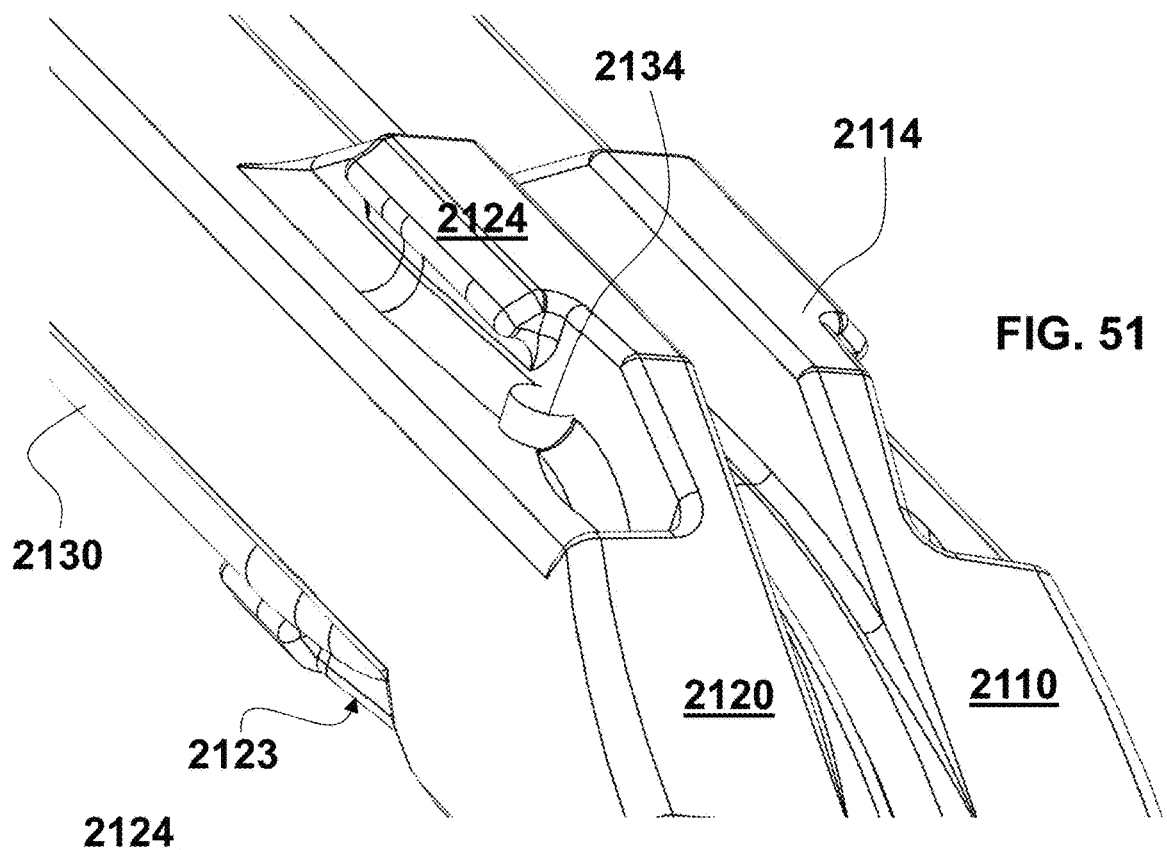
FIG. 51 is a fragmentary, perspective view from above a proximal end of an intermediate portion of the first and second clip struts of the clip of FIG. 41 viewed from above an outer side of the second clip strut with the upper bias device removed.
Figure 52:
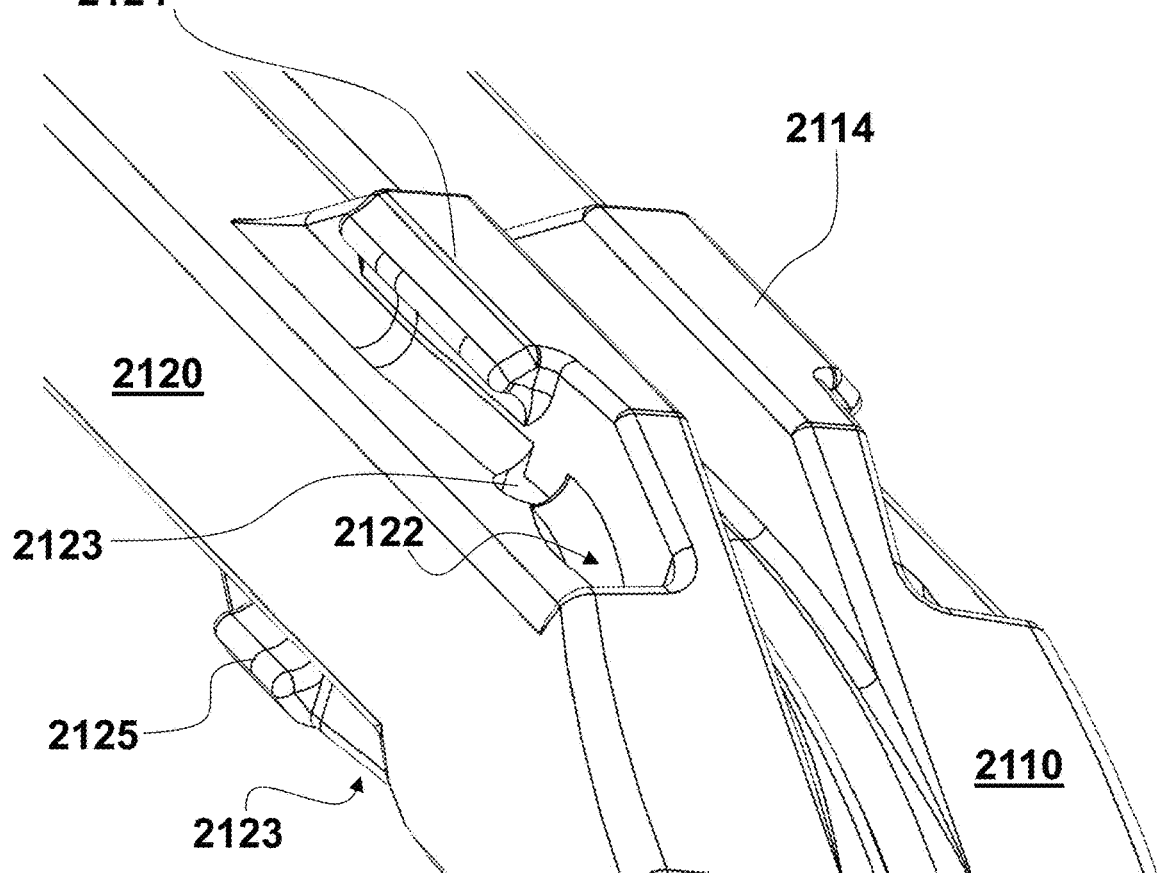
FIG. 52 is a fragmentary, perspective view from above a proximal end of an intermediate portion of the first and second clip struts of the clip of FIG. 41 viewed from above an outer side of the second clip strut with the upper and lower bias devices removed.

FIGS. 51 and 52 depict an exemplary embodiment of a terminal end of the lower bias device 2130 within the bias port 2123 of the clip strut 2120. As can be seen in this example, the bias port 2123 is not a blind hole but, instead, passes entirely through the clip strut 2120 and terminates within the path of the upper bias device 2130 after it exits the bias port 2122. Accordingly, with a properly selected length of the terminal portion after the 90° transverse bend, the distal-most end 2134 will press against the upper bias device 2130 (see FIGS. 51 and 43), thereby imparting a force that presses the upper bias device 2130 against the underside of the second bias anchor 2124 and assists in retaining the upper bias device 2130 in place. This configuration can be provided as well in the first clip strut 2110, which is shown in FIG. 42. Alternatively, the bias ports can be blind holes, in which the respective ends of the bias device 2130 terminate.

As set forth hereinabove, to retain a minimal cross-section throughout a LAA clip-implantation procedure, an exemplary embodiment of a delivery device 1600 to implant the clip 1500, 2100 is configured to grasp the clip struts from respective interior hollows. This configuration is also applicable to the clip 2100. As depicted in FIG. 47, for example, each of the clip struts 2110, 2120 has a respective interior hollow 2116, 2126. When the exemplary embodiment of the delivery device 1600 is employed for implantation, distal internal connectors 1610, 1620, 1710, 1720 of the delivery device 1600 are inserted into the interior hollows 2116, 2126 of the clip struts 2110, 2120 to temporarily secure and control movement and delivery of the clip 2100. To cooperate with the distal internal connectors 1610, 1620, 1710, 1720 of the delivery device 1600, the clip struts 2110, 2120 are either entirely hollow or the clip struts 2110, 2120 have blind holes starting from the proximal end of each of the clip struts 2110, 2120 and passing within the clip struts 2110, 2120 to an interior distance sufficient to allow controlled separation between the two clip struts 2110, 2120 and control of yaw of the clip struts 2110, 2120 with respect to one another.

With the delivery device (e.g., device 1600) accessing and controlling the clip 2100 from an interior of the clip 2100 and not from an exterior of the clip 2100, the delivery device is sized to be equal to or smaller in cross-sectional diameter than the largest cross-sectional diameter of the clip 2100. This means that, in use of the clip 2100, the width of the port is minimized to the largest cross-sectional diameter of the clip 2100 and not to the diameter of the delivery device.

The upper and lower bias devices 2130 form a bias assembly that connects the first clip strut 2110 to the second clip strut 2120 to align the first and second clip struts 2110, 2120 in a strut plane, which plane passes through tissue-contacting surfaces 2118, 2128. In this manner, the upper and lower bias devices 2130 allow the first and second clip struts 2110, 2120 to move in the strut plane, for example, in a yaw motion that is shown, for example, in the progression of FIGS. 23 to 28, from FIGS. 29 to 33, and from FIGS. 35 to 38. Another way of describing this control is that the bias assembly is configured to permit yaw movement of the first and second clip struts 2110, 2120 in the strut plane. The yaw movement of the first clip strut 2110 in the strut plane can be independent of yaw movement of the second clip strut 2120 in the strut plane.

Due to the positions of the bias assembly, the upper and lower bias devices 2130 balance forces such that the first and second clip struts 2110, 2120 undergo substantially no rotation about respective longitudinal axes when the first and second clip struts 2110, 2120 move in the strut plane. The upper and lower bias devices 2130 balance forces such that the first and second clip struts 2110, 2120 have substantially no torque when the first and second clip struts 2110, 2120 move in the strut plane.

As set forth above, the clips described herein (including clip 2100) are, for example, sized to fit into a laparoscopic port having an interior diameter. In this regard, the first and second clip struts 2110, 2120 and the bias assembly 2130 together have a maximum outer width that is no greater than the interior diameter of that port. An exemplary embodiment of the port in which the clip 2100 can be inserted is a 10 mm thoracoscopic port (30 French). Thus, the clip 2100 is able to fit within the port for thoracoscopic delivery to the LAA during a clip-implantation procedure. More particularly, with respect to FIGS. 46 and 47, the outer surfaces of the first and second clip struts 2110, 2120 define a circle 2140 in a transverse cross-sectional plane and this circle 2140 has an outer diameter. The bias devices 2130 traverse portions of the clip struts 2110, 2120 while remaining substantially within this outer diameter such that movement of the clip 2100 within the port is not hampered. Accordingly, the end effector 1601, 2301 of the delivery device 1600, 2300 has an outer diameter no greater than the clip 2100 to allow movement of the entire system within a port, for example, having an interior diameter of approximately 10 mm.

With respect to the longitudinal length of the upper and lower bias devices 2130, for example as shown in FIG. 48, the first and second clip struts 2110, 2120 have a maximum longitudinal length L (parallel to the longitudinal axis of the clip struts 2110, 2120) and the upper and lower bias devices 2130 have a longitudinal length that is shorter than the maximum longitudinal length; see also FIGS. 41 to 45.

The configurations shown in FIGS. 53 to 65 illustrate another exemplary embodiment of an LAA clip 2200 having struts 2210, 2220 and features that can be applied to any of the clips described and/or depicted herein. FIGS. 53 to 65 illustrate the clip 2200 with a bias device 2230 present on both the top and bottom of the struts 2210, 2220. In the configuration of FIGS. 53 to 65, the bias device 2230 is shown for clarity and for other reasons in a cross-section that is cut at a centerline 2231 of the bias device 2230 (both for the upper bias device 2230 and the lower bias device 2230) and, therefore, the bias device 2230 is depicted on only one side of the clip 2200 in each of the drawing figures. In particular, in FIGS. 53, 55, 58, 59, 60, and 62, the half of the bias device 2230 shown is about the strut 2220, and in FIGS. 54, 56, 57, 61, 63, 64, and 65, the half of the bias device 2230 shown is about the strut 2210. It is further noted that the upper and lower bias devices 2230 are depicted as extending past the sides of the struts 2210, 2220, e.g., past the left side of the strut 2210 in FIG. 54 (viewed from the proximal end thereof) and past the left side of the strut 2220 in FIG. 55 (viewed from the distal end thereof). The extension of the upper and lower bias devices 2230 in FIGS. 53 to 65 is not present on the actual LAA clip 2200. This depiction is merely an illustration of pre-load that is present in the spring of the upper and lower bias devices 2230 to establish a bias forcing the two struts 2210, 2220 towards/against one another even when there is no tissue disposed therebetween. Therefore, as can be seen, in particular, in FIG. 58, the centerline 2231 of the upper and lower bias devices 2230 through which the cross-section passes is not aligned with the center longitudinal axis 2202. But, in construction of the LAA clip 2200, the centerline 2231 of the upper and lower bias devices 2230 remains aligned with the center longitudinal axis 2202 in a steady state of the LAA clip 2200 (e.g., the one depicted in FIGS. 58 and 59) and as long as the forces separating the two struts 2210, 2220 are similar for each of the struts; in other words, if there is a force imparted on one of the struts while the other strut remains still or if a force on one of the struts is different from a force on the other of the struts, then the centerline 2231 of the upper and lower bias devices 2230 will not be aligned with the center longitudinal axis 2202. The portions of the bias device 2230 that are not depicted are the mirror image of the portions that are depicted.

As used herein, top and bottom (and upper and lower) are defined as above and use of top and bottom does not mean that a top side of the struts 2210, 2220 must necessarily be on top of a structure on which it is placed. In one example for implantation of the clip 2200 on a LAA, the bottom side of the struts 2210, 2220 can rest on the surface of the heart adjacent the left atrium while the top side faces away from the left atrium and along and/or against some tissue of the LAA that extends away from the heart above the clip 2200.

The first, second, and third bias anchors or bias device connectors 2214, 2215, 2216 at the strut 2210 and the fourth, fifth, and sixth bias anchors or bias device connectors 2224, 2225, 2226 at the strut 2220 are integral to the respective struts 2210, 2220 in this exemplary embodiment. As in the previous exemplary embodiment, the bias device 2230 is not fastened to the struts 2210, 2220 by an external device (such as a clip or anchor) but is, instead, wrapped around various securing points on the struts 2210, 2220 including the first through sixth bias connectors 2214, 2215, 2216, 2224, 2225, 2226. In the exemplary embodiment, after being bent around these securing points on the struts 2210, 2220, the ends of the upper and lower bias devices 2230 are presented within bias ports 2212, 2213, 2222, 2223 in each of the struts 2210, 2220. The bias ports 2212, 2213, 2222, 2223 can be seen in the cross-sections of FIGS. 57 and 65 and the perspective views of FIGS. 57 and 64, for example.

Figure 57:
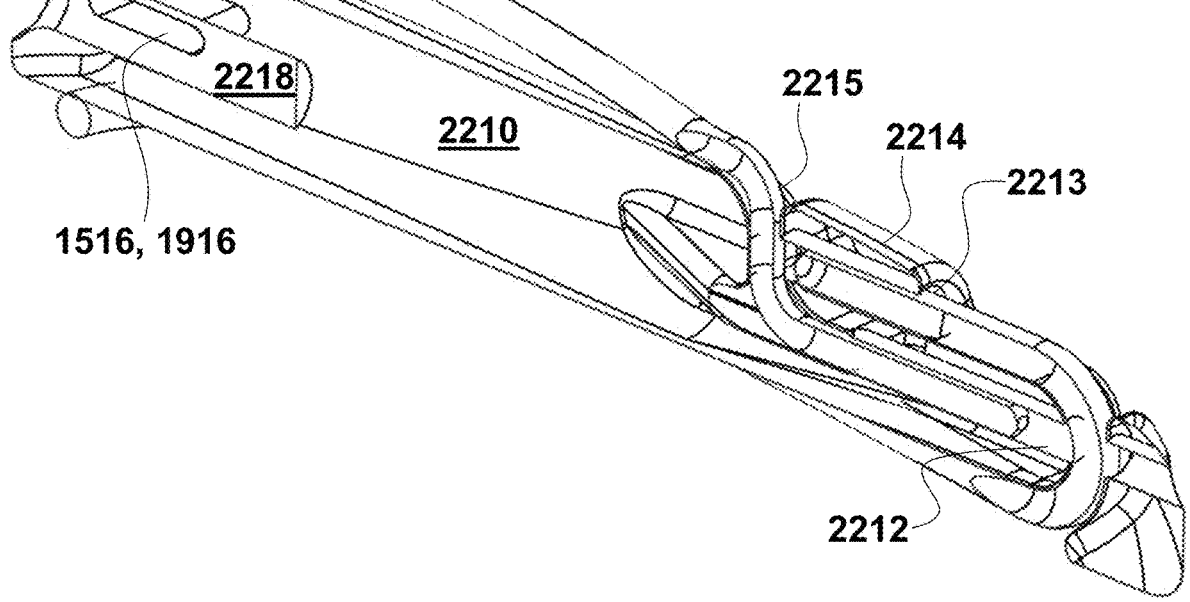
FIG. 57 is a perspective view of a longitudinally vertical cross-section through the upper and lower bias devices and the first clip strut of the clip of FIG. 53 showing an interior hollow of the first clip strut for receiving a portion of a clip delivery device, portions of the upper and lower bias devices and the first clip strut shown in hollow section.
Figures 60, 61:
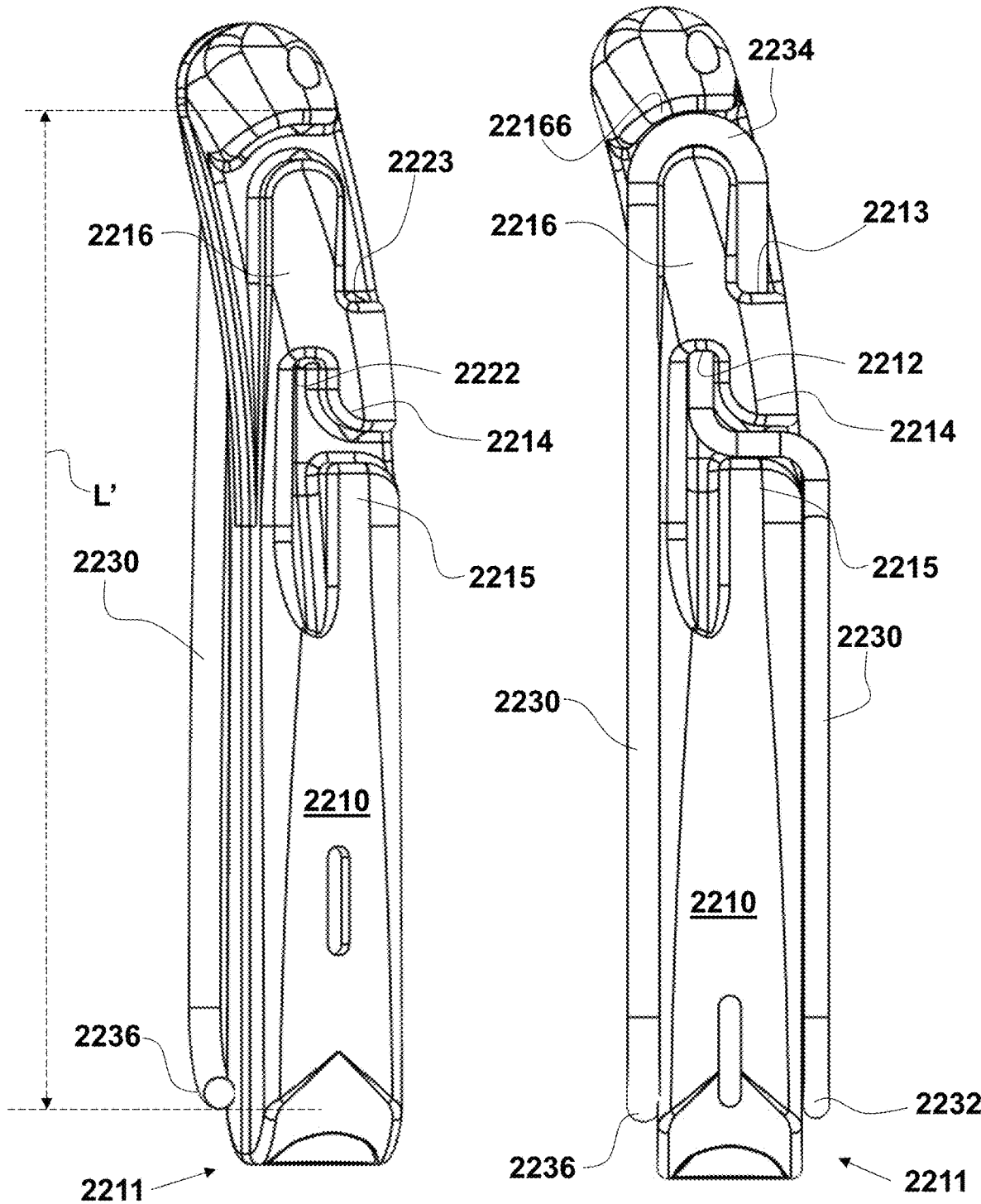
FIG. 60 is a perspective view from below an outer side of the first clip strut of the clip of FIG. 53 with the upper bias device removed and with a cross-section of the lower bias device through a centerline thereof showing a side adjacent the second clip strut and with the lower bias device diagrammatically biased outward away from the second clip strut.
FIG. 61 is a side elevational view of an outer side of the first clip strut of the clip of FIG. 53 with a cross-section of the upper and lower bias devices through a centerline of the upper and lower bias devices showing a side adjacent the first clip strut and with the upper and lower bias devices diagrammatically biased outward away from the first clip strut.
Figure 62:
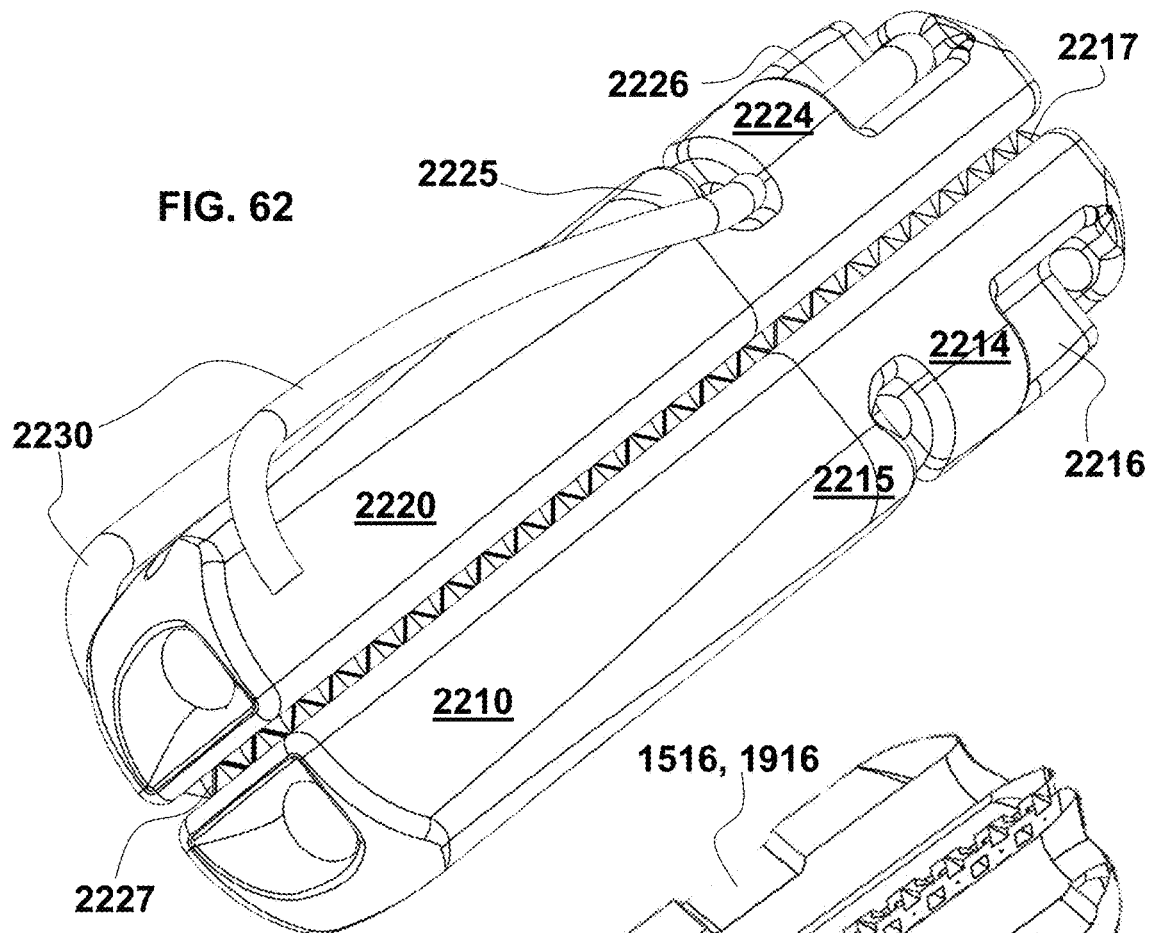
FIG. 62 is a perspective view from above a proximal end of the clip of FIG. 53 with a cross-section of the upper and lower bias devices through a centerline of the upper and lower bias devices showing a side adjacent the second clip strut and with the upper and lower bias devices diagrammatically biased outward away from the second clip strut.
Figure 63:
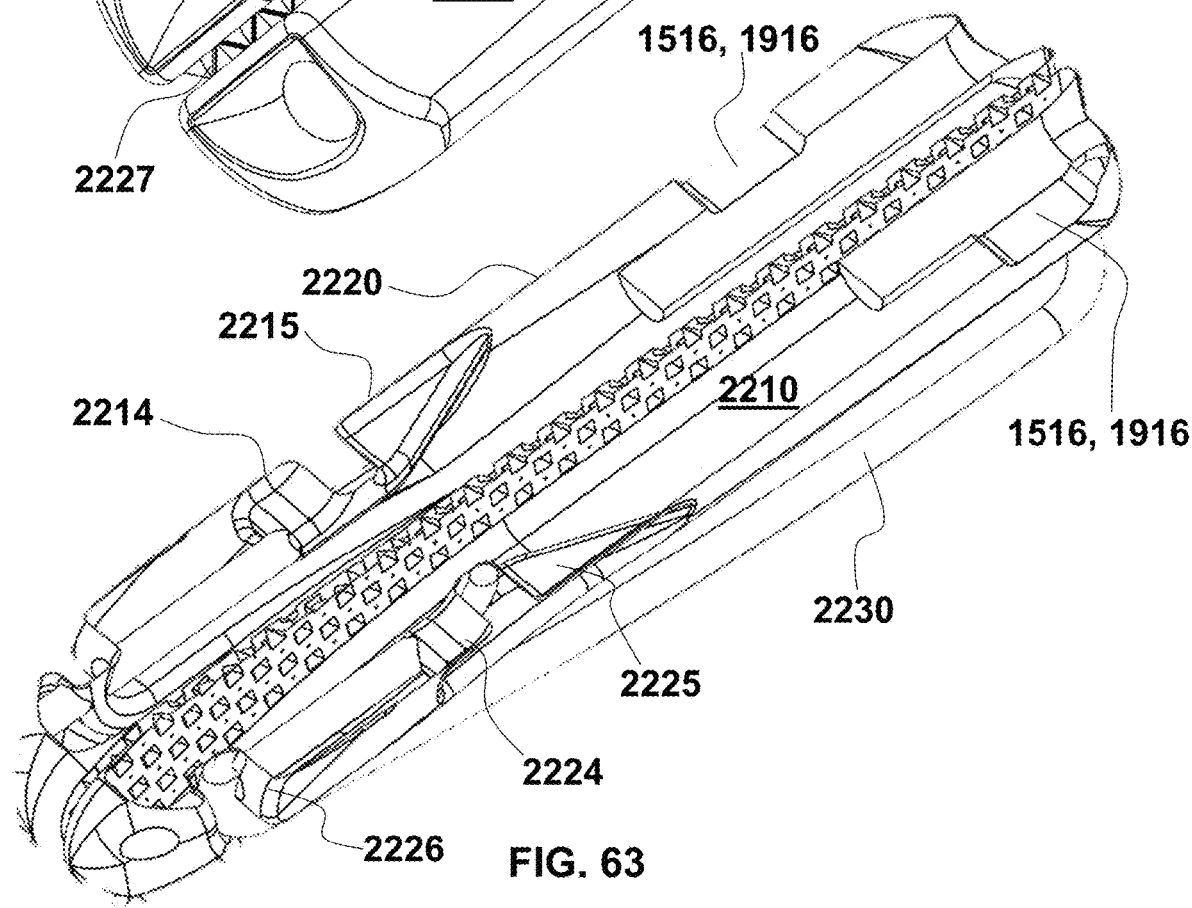
FIG. 63 is a perspective view, from above an outer side of a distal end of the first clip strut of FIG. 53, of a longitudinally horizontal cross-section of the clip showing interior hollows of the first and second clip struts for receiving respective portions of a clip delivery device and with a cross-section of the lower bias device through a centerline thereof showing a side adjacent the first clip strut and with the lower bias device diagrammatically biased outward away from the first clip strut, the first clip strut being partially in hollow cross-section.

The upper bias device 2230, therefore, starts from the upper bias port 2212 (see FIG. 57) that is present in the third bias device connector 2216 and extends in a proximal direction (left with respect to FIG. 57). Continuing, the upper bias device 2230 bends approximately 90° in a transverse direction towards the top side the strut 2210 around and against the first bias device connector 2214 (up with respect to FIG. 57). The upper bias device 2230 then bends through another approximately 90° angle (left with respect to FIG. 57) to traverse in a longitudinal direction towards the bias end 2211 of the strut 2210 to complete an S-bend that passes against and around the second bias device connector 2215. (The word against, as used herein, does not mean that the upper bias device 2230 must rest on top of the upper surface of the first clip strut 2210. The upper bias device 2230 can rest against that surface or can be at a distance therefrom (adjacent) or portions thereof can be touching with other portions thereof at a distance therefrom.) The upper bias device 2230 then extends towards the proximal end of the first clip strut 2110 (e.g., towards the bias end 2211 at the left of FIG. 57). Either before the bias end 2211 of the first clip strut 2210 (which is shown in FIGS. 60 and 61, for example) or after the proximal end of the first clip strut 2210, the upper bias device 2230 makes an approximate 180° bend 2232 in a transverse direction to leave a vicinity of the first clip strut 2210 and enter a vicinity of the second clip strut 2220 (see, e.g., FIG. 58). The bend 2232 ending before the bias ends 2211, 2221 of the clip struts 2210, 2220 is an exemplary feature that ensures that there is still material of the clip struts 2210, 2220 available to contact LAA tissue when compressed LAA tissue between the clip struts 2210, 2220 squeezes to extend beyond the bias device 2230, if that occurs.

Figure 56:
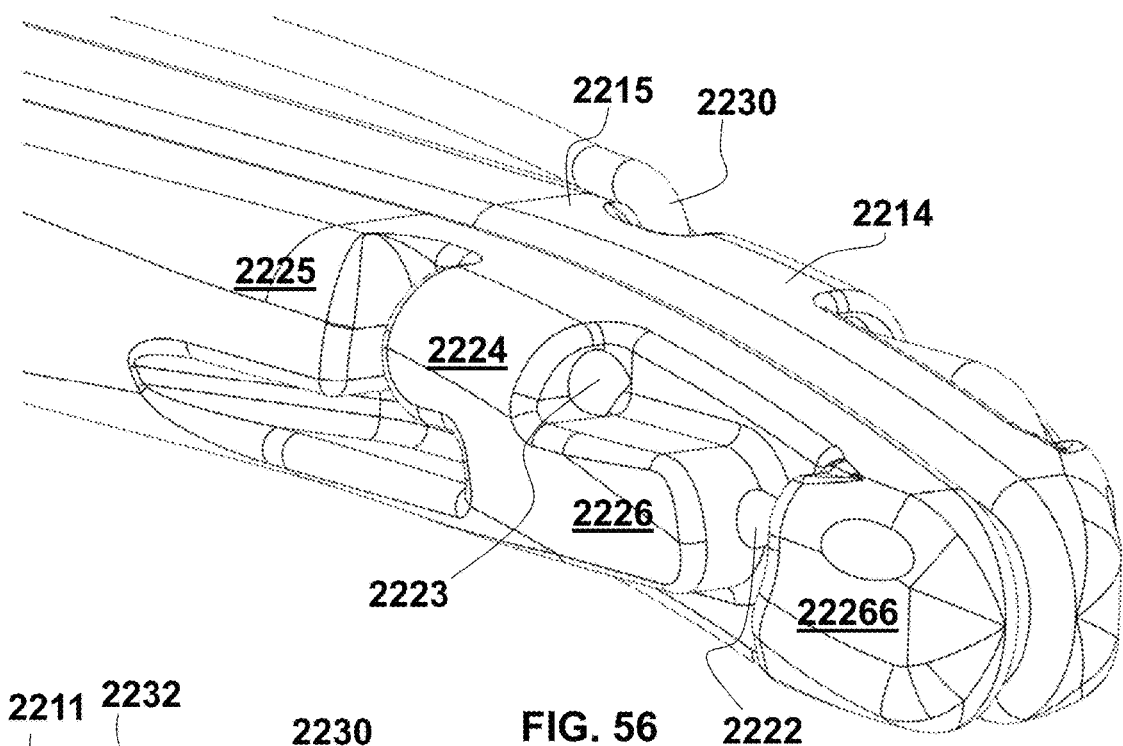
FIG. 56 is a fragmentary, perspective view of a distal portion of the clip of FIG. 53 with a cross-section of the upper and lower bias devices through a centerline of the upper and lower bias devices showing a side adjacent the first clip strut and with the upper and lower bias devices diagrammatically biased outward away from the first clip strut.

The upper bias device 2230 travels longitudinally away from the bias end 2221 of the second clip strut 2220 in a distal direction and passes against and around the fifth bias connector 2225 (see e.g., FIG. 56; this portion of the upper bias device 2230 is not depicted in FIG. 56). The upper bias device 2230 then bends approximately 90° inwards into and between the fourth bias device connector 2224 and the fifth bias device connector 2225 and then bends approximately 90° towards the upper bias port 2222 and terminates within the upper bias port 2222 in the second clip strut 2220. The wall 22266 distal of 2226 also helps retain the bend 2238 of the bias device 2230 in place.

With regard to FIG. 61, the lower bias device 2230, in contrast, starts from the lower bias port 2213 and extends in a distal direction (upwards with respect to FIG. 61). The lower bias device 2230 bends approximately 180° 2234 in a transverse direction against and around the third bias device connector 2216 towards the lower side of the first clip strut 2210. The lower bias device 2230 then extends against and/or along and under the third bias device connector 2216 and travels along the first clip strut 2210 towards the bias end of the first clip strut 2210. (As above, the word against does not mean that the lower bias device 2230 must touch the lower side of the first clip strut 2210. The lower bias device 2230 can rest against that surface or it can be at a distance therefrom (adjacent) or portions thereof can be touching with other portions thereof at a distance therefrom.) In this exemplary embodiment as shown in FIGS. 60 and 61, the lower bias device 2230 extends to just before the bias end 2211 of the first clip strut 2210 (alternatively it can extend past the bias end 2211 of the first clip strut 2110). The lower bias device 2230 makes an approximate 180° bend 2236 in the transverse direction to leave a vicinity of the first clip strut 2210 and enter a vicinity of the second clip strut 2220, as shown in the transition from FIGS. 61 to 60, for example. The lower bias device 2230 then extends longitudinally along the bottom of the second clip strut 2220 from the bias end 2211 in a proximal direction (upwards with respect to FIG. 60), passing against and under the sixth bias device connector 2226. The lower bias device 2230 then bends approximately 180° 2238 inwards against and around the sixth bias device connector 2226 into the lower bias port 2223 and terminates, as shown in FIG. 53, within the lower bias port 2223. The wall 22166 distal of 2216 also helps retain the bend 2234 of the bias device 2230 in place.

FIG. 56 depicts an exemplary embodiment of the locations for terminal ends of the upper and lower bias devices 2230 within the upper and lower bias ports 2222, 2223 of the clip strut 2220 (ports 2212, 2213 of the clip strut 2210 are similar). As can be seen in this exemplary configuration, the upper and lower bias ports 2212, 2213, 2222, 2223 are not blind holes but, instead, have entrances and exits at the respective clip struts 2210, 2220 and each path terminates within the path that the other bias device traverses. Accordingly, with a selected length of the terminal portion of each of the upper and lower bias devices 2230, the distal-most end can be sized to press against a portion of the other bias device (e.g., each upper bias device end can press against a portion of the lower bias device and each lower bias device end can press against a portion of the upper bias device). This connection can be used to impart a force against the other bias device to assist in retaining the upper and lower bias devices 2230 in place on the clip 2200. Alternatively, the selected length of either or both of the terminal portions of each of the upper and lower bias devices 2230 can be sized to not touch a portion of the respective other bias device. In a further alternative, the upper and lower bias ports 2212, 2213, 2222, 2223 can be non-illustrated blind holes.

As set forth hereinabove, to retain a minimal cross-section throughout an implantation procedure of the LAA clip 2200, an exemplary embodiment of a delivery device 1600 usable for the clips (e.g., 1500, 2100) is configured to grasp the clip struts from respective interior hollows. This configuration is also applicable to the clip 2200. As depicted in FIG. 54, for example, each of the clip struts 2210, 2220 has a respective interior hollow 2218, 2228. In an instance where the exemplary embodiment of the delivery device 1600 is employed for implantation of the clip 2200, the distal internal connectors 1610, 1620 of the delivery device 1600 are inserted into the interior hollows 2218, 2228 of the clip struts 2210, 2220 to temporarily secure and control movement and delivery of the clip 2200. To cooperate with the internal connectors 1610, 1620 of the delivery device 1600, the clip struts 2210, 2220 can be a through-hole or the clip struts 2210, 2220 can have blind holes starting from the proximal end of each of the clip struts 2210, 2220 and passing within the clip struts 2210, 2220 to an interior distance sufficient to allow controlled separation between the two clip struts 2210, 2220 and control of yaw of the clip struts 2210, 2220 with respect to one another (which yaw control is described in detail above). An exemplary embodiment of a blind hole configuration of the interior hollow 2218 of the first clip strut 2210 is depicted in FIG. 57. Also depicted in FIG. 57 is a lock orifice 1516, 1916 that is shaped to accommodate entry and temporary locking of a connector lock 1614, 1818 of a respective one of the internal connector 1610, 1620, 1710, 1720 embodiments of the delivery device 1600 (see, e.g., FIGS. 4 to 6 and FIGS. 18 to 20).

Figure 68:
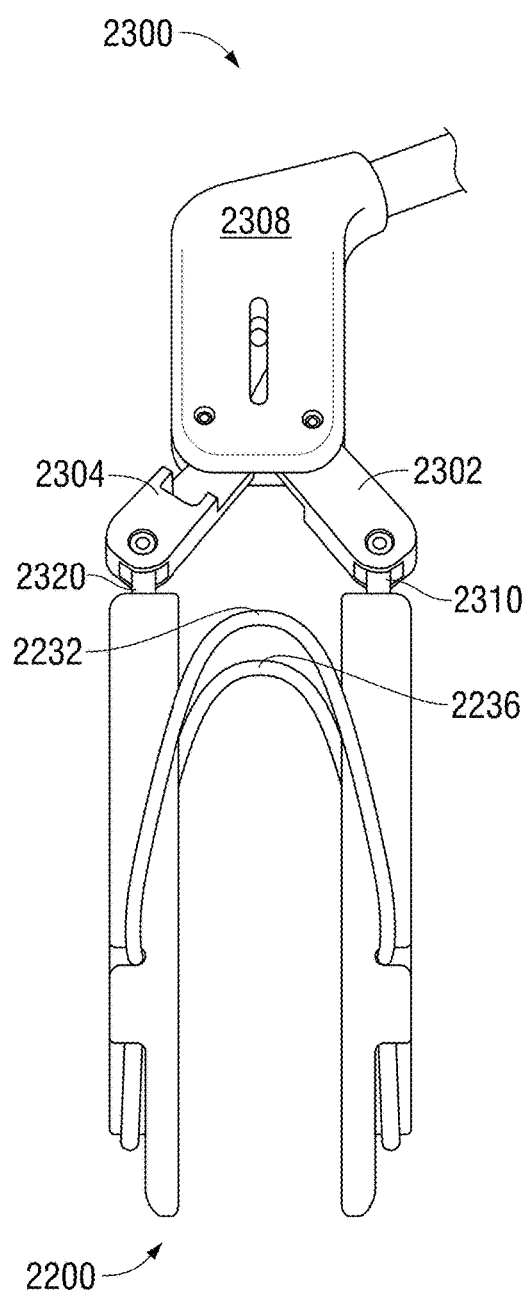
FIG. 68 is a perspective view of the clip and delivery device of FIG. 66 in a second intermediate clip-open orientation with the proximal and distal ends of the clip separated from one another to place the first and second clip struts substantially parallel to one another.
Figure 69:
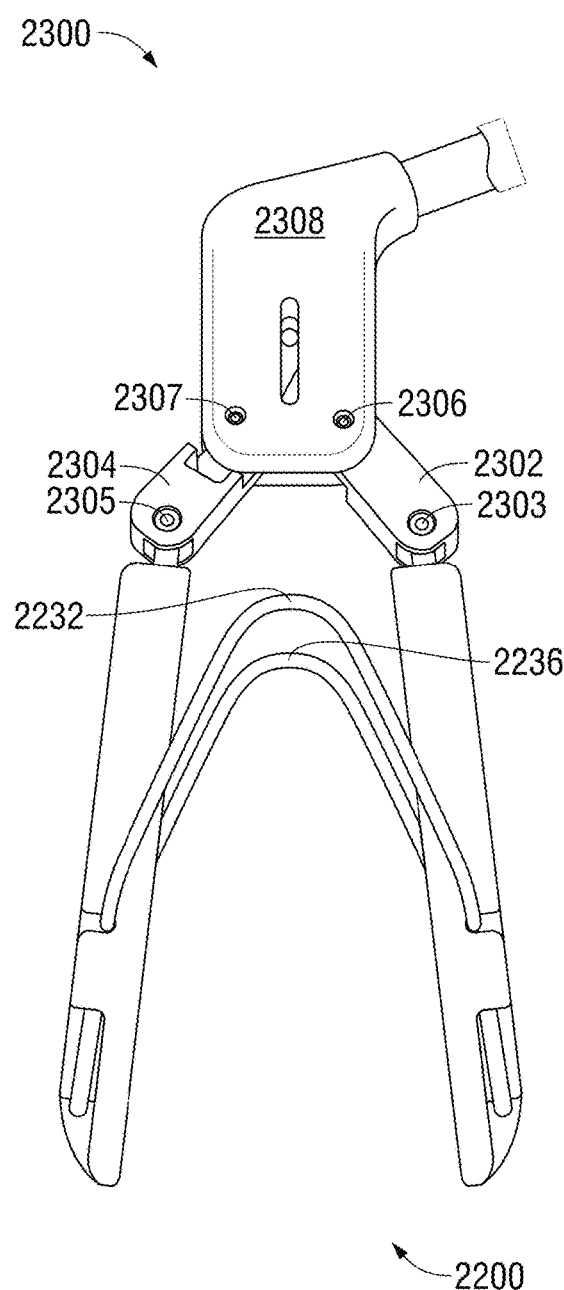
FIG. 69 is a perspective view of the clip and delivery device of FIG. 66 in a clip-fully-open orientation with the proximal and distal ends of the clip separated from one another to place the distal ends of the first and second clip struts further apart from one another than the proximal ends of the first and second clip struts.

FIGS. 66 to 69 illustrate another exemplary embodiment of a delivery device 2300 for controlling, implanting, removing, and re-implanting one of the clips (e.g., 1500, 2100, 2200), in this example, the clip 2200 is installed on the end effector 2301 of the delivery device 2300. The progression from FIG. 66 to FIG. 69 illustrates stages in the installation and implantation of the clip 2200 comprising the struts 2210, 2220 and the upper and lower bias devices 2230. FIG. 66 illustrates the step of first connection and final disconnection of the clip 2200 from the struts 2210, 2220 of the delivery device 2300 and also illustrates a step after the clip 2200 has been removed from a LAA for re-implantation after a surgeon has decided to re-place the clip 2200, for example. FIG. 67 illustrates an intermediate step of opening the struts 2210, 2220 of the clip 2200 with the delivery device 2300 but before the distal tips 2219, 2229 of the struts 2210, 2220 move apart from one another. FIG. 67 also illustrates an intermediate step of closing the clip 2200 before bringing the clip 2200 back to the steady state of FIG. 66. FIG. 66 shows only the upper bias device 2230 but FIG. 67 shows both the upper and lower bias devices 2230. FIG. 68 illustrates an intermediate step of opening and closing the struts 2210, 2220 of the clip 2200 and, in a non-illustrated position where the clip 2200 has been implanted on a LAA, for example, a step just before final disconnection of the struts 2210, 2220 from the delivery device 2300 complete an implantation of the clip 2200. Finally, FIG. 69 illustrates an intermediate step of fully opening the struts 2210, 2220 of the clip 2200 to an open position where the clip 2200 can be maneuvered, for example, on both sides of a LAA. As can be seen, the position of the upper and lower bias devices 2230 being only at the bias end 2211, 2221 of the struts 2210, 2220 allow for a large opening to engage the LAA and to slide the clip 2200 horizontally along and/or vertically down upon the LAA to use the 180° bend 2232 of the upper bias device 2230 and the 180° bend 2236 of the lower bias device 2230 as a stop or back stop to prevent further proximally directed longitudinal movement of the LAA disposed therebetween.

The end effector 2301 of the delivery device 2300 comprises first and second delivery cams 2302, 2304. The first and second delivery cams 2302, 2304 are respectively pivotally connected at distal ends thereof to first and second internal connectors 2310, 2320 at a distal pivot 2303, 2305 and the first and second delivery cams 2302, 2304 are respectively pivotally connected to a delivery clevis 2308 at a respective one of first and second proximal pivots 2306, 2307. Non-illustrated cam actuation connectors control the movement of the delivery cams 2302, 2304 with respect to one another (e.g., closing and opening as comparing FIGS. 66 and 69). A beneficial characteristic arises with the first and second distal pivots 2303, 2305. By allowing the first and second internal connectors 2310, 2320 to pivot freely about a small angle (e.g., between >0° and approximately 60°, in particular, between approximately 20° and approximately 40°, particularly, approximately 30°), the internal connectors 2310, 2320 permit easy self-alignment so that when the second internal connector 2320 is inserted (in an exemplary embodiment where it is longer), the first internal connector 2310 can be pivoted as desired with the second internal connector 2320 remaining relatively still, referred to herein as passive alignment. Lengths of the internal connectors 2310, 2320 are discussed hereinabove.

The struts 2210, 2220 are connected respectively to the first and second internal connectors 2310, 2320. In this exemplary embodiment, the struts 2310, 2320 have respective interior hollows 2218, 2228, here in the form of cylindrical, blind holes. Likewise, the first and second internal connectors 2310, 2320 have first and second shafts each with an external shape corresponding to the respective interior hollows 2218, 2228 for mating therein. The shapes can have a circular cross-section and a rounded tip in an exemplary embodiment. However, the shapes of the two shafts can be different, for example, one circular and one polygonal in cross-section. If the internal connectors 2310, 2320 were simply inserted within the interior hollows 2218, 2228, then it would be possible for the struts 2210, 2220 to slip off. To retain each of the struts 2210, 2220 on the respective internal connectors 2310, 2320, at least one of the internal connectors 2310, 2320 is provided with a non-illustrated connector lock or both of the internal connectors 2310, 2320 are provided with connector locks (examples of which are previously described, for example locks 1614, 1624, 1818). More specifically, the locks permit removable capture or securement of the clip 2200 onto the delivery device 2300. A desirable exemplary shape of the entrance to each of the interior hollows 2218, 2228 is conical because it enables a user to insert the internal connectors 2310, 2320 into the interior hollows 2218, 2228 and to allow the shafts to enter therein even if the central axes of the internal connectors 2310, 2320 are slightly out of alignment with the central axes of the interior hollows 2218, 2228.

With the delivery device (e.g., devices 1600, 2300) accessing and controlling the clip 2200 from an interior of the clip 2200 and not from an exterior of the clip 2200, the delivery device is sized to be equal to or smaller in cross-sectional area than the largest cross-sectional diameter of the clip 2200. (It is noted that the interior hollows can be placed on the end of the cams 2302, 2304 and the internal connectors can be at the struts in a reverse configuration.) This means that, in use of the clip 2200, the width of the port is minimized to the largest cross-sectional diameter of the clip 2200 and not to the diameter of the delivery device.

The upper and lower bias devices 2230 form the bias assembly that connects the first clip strut 2210 to the second clip strut 2220 to align the first and second clip struts 2210, 2220 in a strut plane, which plane passes through tissue-contacting surfaces 2217, 2227. In this manner, the upper and lower bias devices 2230 allow the first and second clip struts 2210, 2220 to move in the strut plane, for example, in a yaw motion that is shown, for example in the progression of FIGS. 66 to 69. As described above, the bias assembly is configured to permit yaw movement of the first and second clip struts 2210, 2220 in the strut plane. The yaw movement of the first clip strut 2110 in the strut plane can be independent of yaw movement of the second clip strut 2120 in the strut plane. Due to the positions of the bias assembly, the upper and lower bias devices 2230 balance forces such that the first and second clip struts 2210, 2220 undergo substantially no rotation about respective longitudinal axes when the first and second clip struts 2210, 2220 move in the strut plane. The upper and lower bias devices 2230 balance forces such that the first and second clip struts 2210, 2220 have substantially no torque when the first and second clip struts 2210, 2220 move in the strut plane.

As explained above, the clips described herein (including LAA clip 2200) are, for example, sized to fit into a laparoscopic port having an interior diameter. In this regard, the first and second clip struts 2210, 2220 and the bias assembly 2230 together have a maximum outer width that is no greater than the interior diameter of that port. An exemplary embodiment of the port in which the LAA clip 2200 can be inserted is a 10 mm thoracoscopic port (30 French). Thus, the LAA clip 2200 is able to fit within the port for thoracoscopic delivery to the LAA during a clip-implantation procedure.

With respect to the longitudinal length of the upper and lower bias devices 2230, for example as shown in FIG. 66, the first and second clip struts 2210, 2220 have a maximum longitudinal length (parallel to the longitudinal axis of the clip struts 2210, 2220) and the upper and lower bias devices 2230 have a longitudinal length that is shorter than the maximum longitudinal length because the size insures that there is still material of the clip struts 2210, 2220 available to contact LAA tissue when compressed LAA tissue between the clip struts 2210, 2220 squeezes to extend beyond the bias device 2230, if that occurs.

It is noted that a few of the exemplary embodiments described herein have the upper and lower bias devices 2030, 2130, 2230 on opposing sides of the struts, each having a distal open end on the same side and a proximal bias end 2211, 2221 on the same side. FIG. 71 illustrates an alternative configuration where one of the bias devices 2030, 2130, 2230 is rotated 180° to have the two bias ends opposite one another. In the exemplary configuration shown in the diagram of FIG. 71, the bias devices 2030, 2130, 2230 are still on opposite sides of the clip struts. This configuration, therefore, does not allow entry of the structure to be clipped (e.g., the LAA) from one end of the clip; rather, the structure to be clipped enters from below or above the clip into the central clipping area 1970.

Figure 75:
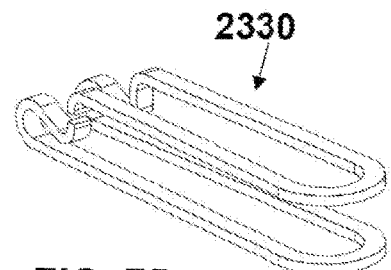
FIG. 75 is a perspective view of an exemplary embodiment of a bias device for an exclusion clip.
Figure 75A:
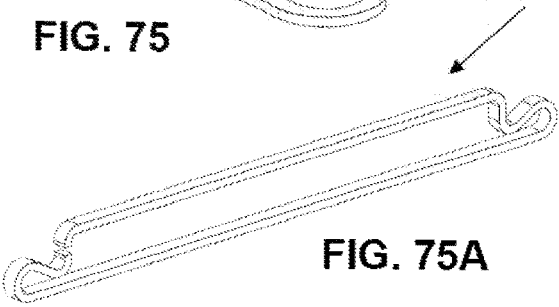
FIG. 75A is a perspective view of the bias device of FIG. 75 before being bent.

In the aforementioned exemplary embodiments of the bias device 2030, 2130, 2230, the upper and lower bias devices are illustrated as primarily constructed of round profile cord. However, there are other designs and construction methods that have their own merits. For example, the cord could be of a square or rectangular profile, such as shown in FIGS. 75 and 75A, allowing the bias force of the bias device 2330, 2430 to be carefully tuned by altering width and height of the cord profile independently. Further, the edges of a polygon profiled cord can be rounded to various radii, allowing even further tuning of the bias device 2030, 2130, 2230, 2330, 2430 while maintaining a consideration of the edges of the bias device's interaction with delicate tissues.

Figure 76:
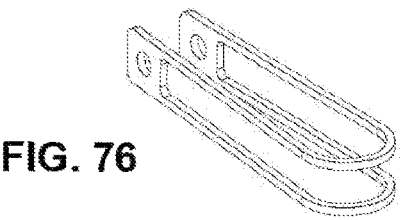
FIG. 76 is a perspective view of another exemplary embodiment of a bias device for an exclusion clip.
Figure 76A:
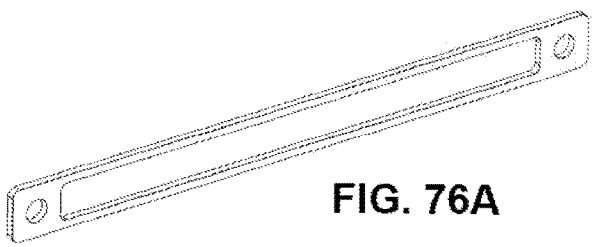
FIG. 76A is a perspective view of the bias device of FIG. 76 before being bent.

Additionally, in the aforementioned embodiments of the bias device 2030, 2130, 2230, the upper and lower bias devices are illustrated as separate components, each with two terminated ends. As an alternative, the bias device 2330, 2430 can be constructed from fewer or greater separate components, resulting in fewer or greater terminated ends. In an exemplary embodiment, the upper and lower bias devices 2030, 2130, 2230 can be a singular member. For example, the bias devices 2330, 2430 can be a single continuous wire form or a flat component that is cut out of flat stock and bent to shape, such as the configurations shown in FIGS. 76 and 76A, which are not wireforms but are two-dimensional shapes that are then cut and bent.

In an exemplary embodiment, the upper and lower bias devices are joined at both ends to form a continuous loop without terminated ends. In another exemplary embodiment, the upper and lower bias devices are joined at one location, resulting in two terminated ends. In yet another embodiment, the bias device is fabricated by first cutting a flat continuous loop shape that is then bent to the final shape, mimicking the geometry of an aforementioned bias device 2030, 2130, 2230. In such configurations, the four terminated ends might not be terminated as with two separate bias devices, the structure can either be one long bias device that wraps around with two terminated ends or the bias device can be a continuous component with no terminated end.

The aforementioned exemplary embodiments of the end effector show a jaw control cord acting on jaws in a direction vector parallel to a clip centerline, e.g., the central longitudinal axis 2202. The jaw control cord then makes an approximately 45° bend to stay within the clevis and the lumen of the shaft. This configuration has a relatively long distance between a distal tip of the delivery cam and a proximal end of the clevis, hereinafter referred to as a long dead length. A long dead length requires more room between the proximal end of the clip and tissue structures in the patient, making proper placement of the clip more difficult (especially in tighter thoracic cavities).

A more favorable configuration minimizes the dead length, giving the surgeon more room to manipulate the end effector and clip, and enabling easier placement of the clip. The exemplary embodiment of the delivery device 2400 shown in FIGS. 77 to 80 improves the performance by shortening the dead length.

Figure 77:
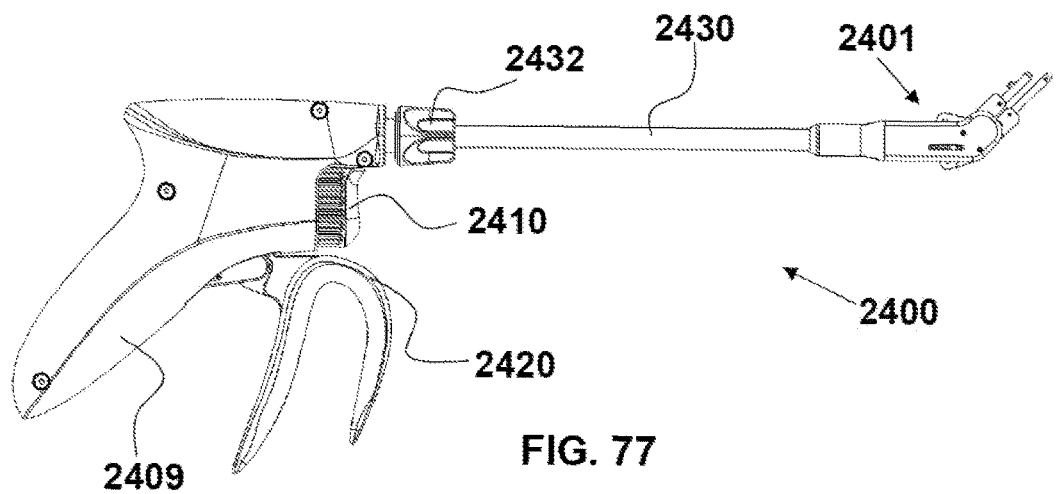
FIG. 77 is a side elevational view of another exemplary embodiment of a clip delivery device with an end effector having a clevis and jaws in a jaw-closed state, a shaft, and a handle with a jaw trigger, an unlock button, and a shaft rotation wheel.
Figure 78:
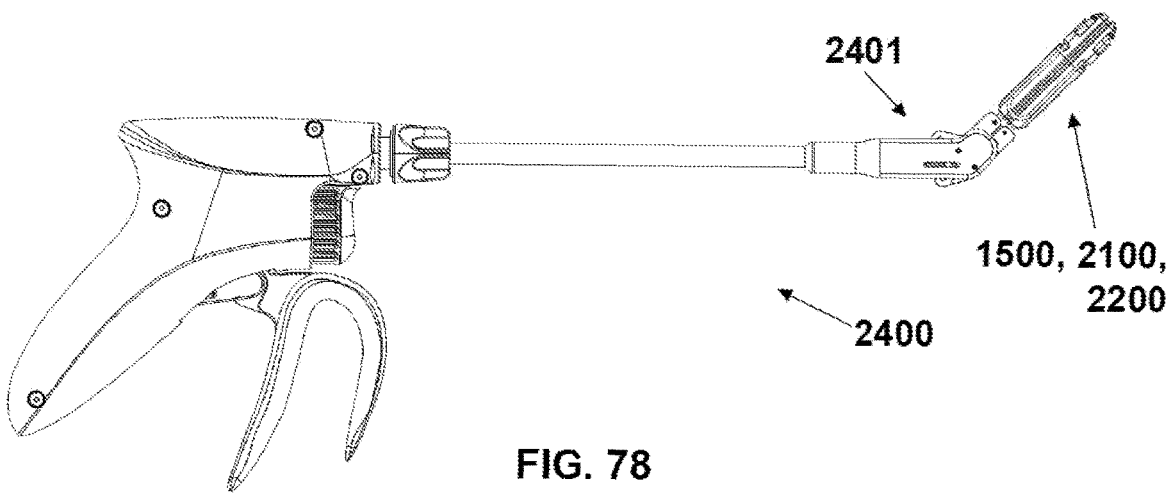
FIG. 78 is a side elevational view of the clip delivery device of FIG. 77 with an occlusion clip installed on the jaws of the end effector.

Another exemplary embodiment of the delivery device 2400 shown in FIGS. 77 and 78 is used to deliver the clip 1500, 2100, 2200 to the LAA 20. This exemplary embodiment has a pistol grip configuration. The delivery device 2400 has an end effector 2401, a handle 2409 with a lock/unlock controller 2410 in the form of a button trigger, a jaw control 2420 in the form of a trigger, and a shaft 2430 having a shaft rotation knob 2432 and an end effector 2401. The lock/unlock controller 2410 actuates a lock release cord 2416, in the form of a pull cord, to unlock the lock 1614 for the clip 1500, 2100, 2200. When actuated, the lock/unlock controller 2010 exerts a proximally directed force (e.g., on the lock release cord) to release the lock 1614 upon the clip struts, thereby allowing the clip to leave the delivery device 2400 and be implanted. Only one lock 1614 is mentioned here, however, all locks described and envisioned here are equally applicable to the delivery device 2400. For recapture of the clip, the delivery device 2400 is moved into a recapture position and first and second internal connectors 1610, 1620 are respectively inserted into first and second connector interfaces of the clip struts. In the exemplary embodiment described herein, the lock control (e.g., the lock release cord 2416 and the lock/unlock controller 2010) can automatically lock during recapture or the lock can be manually operated to lock the internal connectors 1610, 1620 within the connector interfaces of the clip. If rotation of the end effector 2410 with respect to the handle 2409 is desired, the surgeon rotates the shaft rotation knob 2432 in the desired direction.

Figure 79:
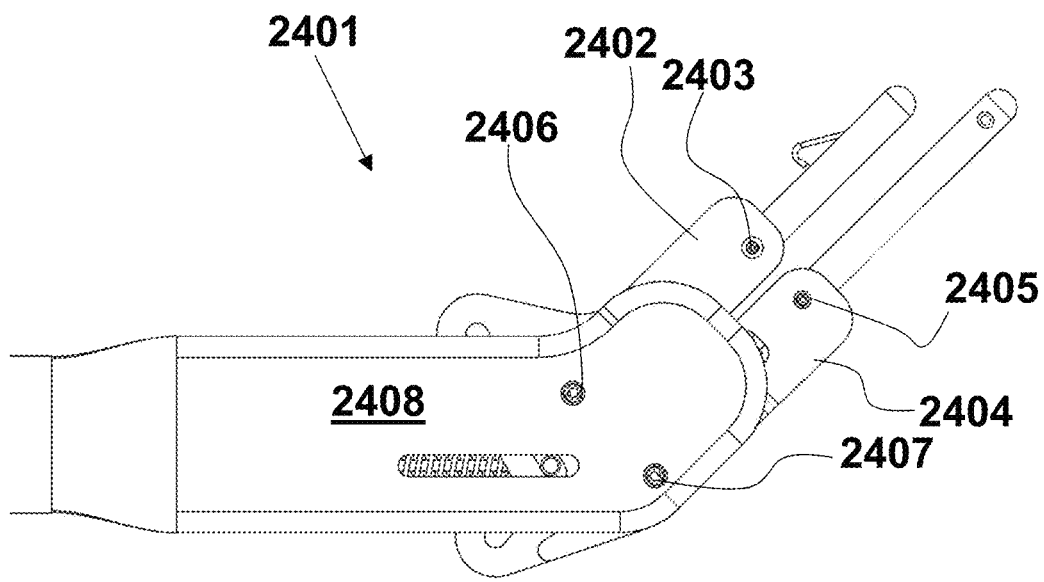
FIG. 79 is a fragmentary, enlarged, side elevational view of a distal portion of the shaft and the end effector of the clip delivery device of FIG. 77.
Figure 80:
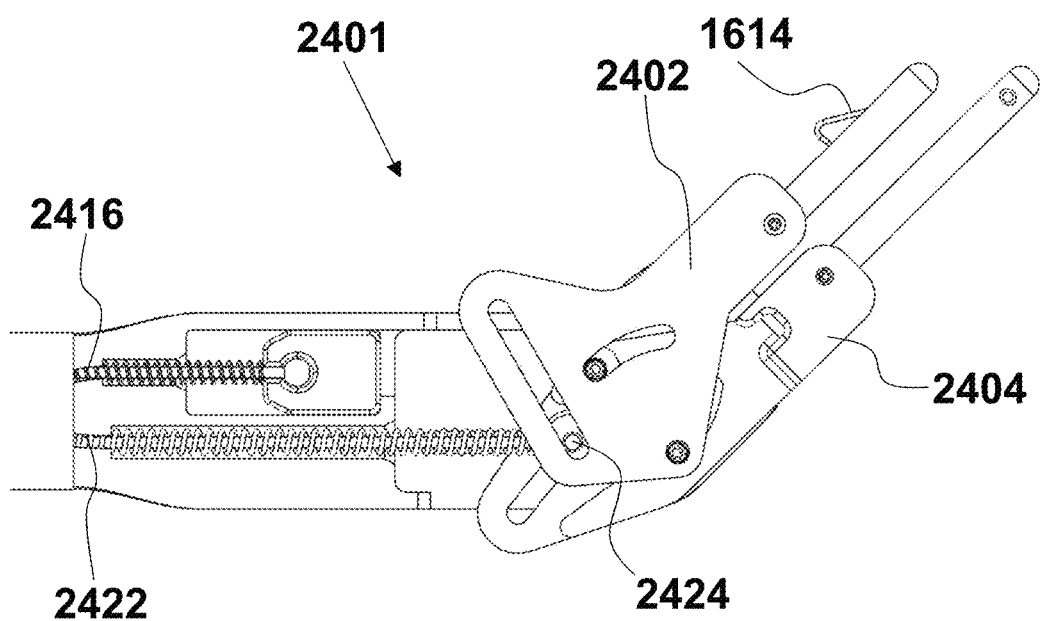
FIG. 80 is a fragmentary, enlarged, side elevational view of a distal portion of the shaft and the end effector of the clip delivery device of FIG. 77 with the facing clevis half removed to show the jaw and lock controls of the end effector.

The jaw and lock controls at the end effector 2401 are depicted in FIGS. 79 and 80. The facing half of the clevis 2408 is removed in FIG. 80 to show the lock release cord 2416, which is attached to a pull block 2418 that is connected to the lock 1614, and the jaw control cord 2422, which is connected to a cam 2424 that, when moved distally or proximally, moves the first and second delivery cams 2402, 2404 about their respective pivots 2406, 2407. The first and second internal connectors 1610, 1620 are pivotally connected to the first and second delivery cams 2402, 2404 respectively about first and second distal pivots 2403, 2405.

In operation, the jaw control cord 2422 acts on the jaws 2402, 2404 in an axis non-parallel with a clip centerline, eliminating the approximately 45° bend needed to stay within the clevis 2401 and the lumen of the shaft 2430, and, therefore, shortening the dead length. In addition, removal of the approximately 45° bend in favor of a more in-line actuation of the jaw control cord 2422 on the jaws reduces friction and load on the jaw control cord 2422, improving system performance and reducing wear on the delivery system. In summary, a longer dead length on the distal end of the delivery system 1600 makes placement of the clip more difficult in patients with tighter/more cramped chest cavities. Shortening that dead length in the delivery system 2400 makes the implantation effort easier by eliminating the 45° bend that the jaw control cord used to take.

In an exemplary configuration, a control rod can be used to change the angle from a straight-ahead position to an angled position. Such a configuration would allow the user to adjust an angle during a procedure and would allow the shaft 2430 and end effector 2401 to operation through a straight cannulae.

As indicated in exemplary embodiments herein, the clip struts are substantially rectangular in cross-section. These are only exemplary embodiments. The clip struts can also be circular, ovular, or polygonal in cross-section. Accordingly, the use of first, second, third, and fourth as descriptors of four sides is merely exemplary and is not to be taken as limiting. In an embodiment where the cross-section is circular or ovular, the enumerated sections could be first, second, third, and fourth quadrants, portions, or sides.

Herein, the word "cord" is used with respect to, for example, the first and second release cords 1616, 1618, the lock control cord 1816, and the jaw control cord 2022. This word is meant to be broad and not limited to a particular material or cross-section. The cord refers to any longitudinally extending material that can comprise the structure and function described herein. As defined herein, the term cord is not limited to a single cord; a cord can be a plurality of cords as well. Therefore, cord and cords are used interchangeably. Cords also are not limited to a particular type of material. The material can be made of natural fibers, manmade or synthetic fibers, plastics, and/or metals, to name a few. Cords also are not limited to a particular structure. The material can be made of twisted strands, twisted strands with a central core, a single strand or wire, or a rod, to name a few. One exemplary embodiment described herein is a braided stainless steel cable. The embodiments described herein, however, are not limited to braided stainless steel cable, even though the example of braided stainless steel cable is referred to or is used herein.

In various instances herein, a hole is referred to as a "blind" hole. Where so indicated, in exemplary alternative embodiments, some of the holes can be through-holes.

It is noted that various individual features of the inventive processes and systems may be described only in one exemplary embodiment herein. The particular choice for description herein with regard to a single exemplary embodiment is not to be taken as a limitation that the particular feature is only applicable to the embodiment in which it is described. All features described herein are equally applicable to, additive, or interchangeable with any or all of the other exemplary embodiments described herein and in any combination or grouping or arrangement. In particular, use of a single reference numeral herein to illustrate, define, or describe a particular feature does not mean that the feature cannot be associated or equated to another feature in another drawing figure or description. Further, where two or more reference numerals are used in the figures or in the drawings, this should not be construed as being limited to only those embodiments or features, they are equally applicable to similar features or not a reference numeral is used or another reference numeral is omitted.

The foregoing description and accompanying drawings illustrate the principles, exemplary embodiments, and modes of operation of the systems, apparatuses, and methods. However, the systems, apparatuses, and methods should not be construed as being limited to the particular embodiments discussed above. Additional variations of the embodiments discussed above will be appreciated by those skilled in the art and the above-described embodiments should be regarded as illustrative rather than restrictive. Accordingly, it should be appreciated that variations to those embodiments can be made by those skilled in the art without departing from the scope of the systems, apparatuses, and methods as defined by the following claims.

What is claimed is:

1. An external left atrial appendage (LAA) exclusion clip recapture system, comprising:
   an LAA exclusion clip comprising:
      a first clip strut comprising a first connector interface; and
      a second clip strut comprising a second connector interface, at least one of the first and second connector interfaces comprising a first portion of a lock; and
   a delivery and recapture device comprising:
      a handle comprising a jaw control and a lock control; and
      an end effector connected to the handle and comprising:
         a clevis; and
         first and second jaws:
            connected to the clevis;
            biased towards a closed orientation;
            operatively connected to the jaw control to actively articulate at least one of the first and second jaws with respect to the other;
            having respective first and second connectors, the first connector of the first jaw having a given length and the second connector of the second jaw having a length different from the given length; and
            at least one of the first and second connectors comprising a second portion of the lock and being operatively connected to the lock control to removably lock with the first portion of the lock.

2. The system according to claim 1, wherein:
the first connector is a first internal connector shaped to connect within either of the first and second connector interfaces; and
the second connector is a second internal connector shaped to connect within either of the first and second connector interfaces.

3. The system according to claim 1, wherein:
the first connector interface is a longitudinal bore; and
the second connector interface is a longitudinal bore.

4. The system according to claim 1, wherein at least one of the first and second connectors is pivotably connected to a respective one of the first and second jaws, is biased to an approximately parallel orientation with respect to the other one of the first and second connectors, and is configured to pivot passively from the approximately parallel orientation.

5. The system according to claim 4, wherein the at least one of the first and second connectors is configured to pivot passively in a range from the approximately parallel orientation to an angle approximately +/−30°.

6. The system according to claim 1, wherein the first and second connectors are respectively independently pivotably connected to a respective one of the first and second jaws, are biased to an approximately parallel orientation, and are each configured to pivot passively from the approximately parallel orientation.

7. The system according to claim 6, wherein the at least one of the first and second connectors is configured to pivot passively in a range from the approximately parallel orientation to an angle approximately +/−30°.

8. The system according to claim 1, wherein the first and second connectors are each pivotably connected such that, while a longer one of the first and second connectors is at least partially inserted within one of the first and second connector interfaces, motion of the handle allows a user to passively align a shorter one of the first and second connectors into the other one of the first and second connector interfaces.

9. The system according to claim 1, wherein:
both of the first and second connector interfaces comprise the first portion of the lock; and
both of the first and second connectors comprise the second portion of the lock and are each operatively connected to the lock control to removably lock with the respective first portion of the lock.

10. The system according to claim 9, wherein the first and second portions of the lock have a locked state and are configured:
to unlock the locked state upon actuation of the lock control; and
after having been released, to automatically re-enter the locked state as the first and second portions of the lock are moved back together.

11. The system according to claim 1, wherein the first and second portions of the lock have a locked state and are configured:
to unlock the locked state upon actuation of the lock control; and
after having been released, to automatically re-enter the locked state as the first and second portions of the lock are moved back together.

12. The system according to claim 1, wherein the first and second connectors are cylindrical pins.

13. An external left atrial appendage (LAA) exclusion clip recapture system, comprising:
an LAA exclusion clip comprising:
a first clip strut comprising a first connector interface; and
a second clip strut comprising a second connector interface, at least one of the first and second connector interfaces comprising a first portion of a lock; and
a delivery and recapture device comprising:
a handle comprising a jaw control and a lock control; and
an end effector connected to the handle and comprising:
a clevis; and
first and second jaws:
each pivotably connected to the clevis and are operatively connected to the jaw control to actively articulate with respect to one another;
operatively connected to the jaw control to actively articulate at least one of the first and second jaws with respect to the other;
having respective first and second connectors, the first connector of the first jaw having a given length and the second connector of the second jaw having a length different from the given length; and
at least one of the first and second connectors comprising a second portion of the lock and being operatively connected to the lock control to removably lock with the first portion of the lock.

14. The system according to claim 13, wherein:
the first connector is a first internal connector shaped to connect within either of the first and second connector interfaces; and
the second connector is a second internal connector shaped to connect within either of the first and second connector interfaces.

15. The system according to claim 13, wherein:
the first connector interface is a longitudinal bore; and
the second connector interface is a longitudinal bore.

16. The system according to claim 13, wherein at least one of the first and second connectors is pivotably connected to a respective one of the first and second jaws, is biased to an approximately parallel orientation with respect to the other one of the first and second connectors, and is configured to pivot passively from the approximately parallel orientation.

17. The system according to claim 16, wherein the at least one of the first and second connectors is configured to pivot passively in a range from the approximately parallel orientation to an angle approximately +/−30°.

18. The system according to claim 13, wherein the first and second connectors are respectively independently pivotably connected to a respective one of the first and second jaws, are biased to an approximately parallel orientation, and are each configured to pivot passively from the approximately parallel orientation.

19. The system according to claim 18, wherein the at least one of the first and second connectors is configured to pivot passively in a range from the approximately parallel orientation to an angle approximately +/−30°.

20. The system according to claim 13, wherein the first and second connectors are each pivotably connected such that, while a longer one of the first and second connectors is at least partially inserted within one of the first and second connector interfaces, motion of the handle allows a user to passively align a shorter one of the first and second connectors into the other one of the first and second connector interfaces.

21. The system according to claim 13, wherein the first and second jaws are biased towards a closed orientation.

22. The system according to claim 13, wherein:
both of the first and second connector interfaces comprise the first portion of the lock; and
both of the first and second connectors comprise the second portion of the lock and are each operatively connected to the lock control to removably lock with the respective first portion of the lock.

23. The system according to claim 22, wherein the first and second portions of the lock have a locked state and are configured:
to unlock the locked state upon actuation of the lock control; and
after having been released, to automatically re-enter the locked state as the first and second portions of the lock are moved back together.

24. The system according to claim 13, wherein the first and second portions of the lock have a locked state and are configured:
to unlock the locked state upon actuation of the lock control; and
after having been released, to automatically re-enter the locked state as the first and second portions of the lock are moved back together.

25. The system according to claim 13, wherein the first and second connectors are cylindrical pins.

26. A left atrial appendage (LAA) exclusion clip delivery and recapture system for an LAA exclusion clip having a pair of struts each with a respective recapture interface at a proximal end thereof, the system comprising:
an LAA clip delivery and recapture device comprising:
a handle portion comprising a distal end and a jaw control; and
an end effector at the distal end of the handle portion and comprising:
a clevis;
first and second jaws, both of the first and second jaws pivotably connected to the clevis and connected to the jaw control such that, activation of the jaw control actively articulates the first and second jaws with respect to each other; and
first and second clip recapture connectors:
respectively connected to one of the first and second jaws; and
having respective longitudinal lengths different from one another to define a long recapture connector and a short recapture connector.

27. The system according to claim 26, wherein each of the first and second clip recapture connectors has a respective external shape and further comprising an LAA exclusion clip comprising first and second clip struts, each of the first and second clip struts having a proximal end and defining an internal recapture interface at the proximal end, the internal recapture interface having an internal shape corresponding to one of:
at least one of the first and second recapture connectors; and
either one of the first and second recapture connectors.

28. A left atrial appendage (LAA) exclusion clip delivery and recapture system, comprising:
an LAA exclusion clip having a pair of struts each with a respective recapture interface at a proximal end thereof; and
an LAA clip delivery and recapture device comprising:
a handle portion having a distal end and a jaw control; and
an end effector at the distal end of the handle portion and comprising:
a clevis;
first and second jaws biased towards a closed orientation, at least one of the first and second jaws pivotably connected to the clevis, the at least one of the first and second jaws connected to the jaw control such that, activation of the jaw control actively articulates the at least one of the first and second jaws with respect to the other one of the first and second jaws; and
first and second clip recapture connectors:
respectively connected to one of the first and second jaws;
having respective longitudinal lengths different from one another to define a long recapture connector and a short recapture connector; and
being configured to removably connect with at least one of the recapture interfaces of the pair of struts.

29. The system according to claim 28, wherein at least one of the first and second connectors:
is pivotably connected to a respective one of the first and second jaws;
is biased to an approximately parallel orientation with respect to the other one of the first and second connectors; and
is configured to pivot passively from the approximately parallel orientation.

30. The system according to claim 29, wherein the at least one of the first and second connectors is configured to pivot passively in a range from the approximately parallel orientation to an angle approximately +/−30°.

31. The system according to claim 28, wherein:
the handle portion further comprises a lock control;
both of the recapture interfaces of the pair of struts comprise a first portion of a lock; and
both of the first and second clip recapture connectors comprise a second portion of the lock and are each operatively connected to the lock control to removably lock with the first portion of the lock.

32. The system according to claim 31, wherein the first and second portions of the lock have a locked state and are configured:
to unlock the locked state upon actuation of the lock control; and
after having been released, to automatically re-enter the locked state as the first and second portions of the lock are moved back together.

33. An external left atrial appendage (LAA) exclusion clip recapture system, comprising:
an LAA exclusion clip comprising:
a first clip strut comprising a first connector interface; and
a second clip strut comprising a second connector interface, at least one of the first and second connector interfaces comprising a first portion of a lock; and
a delivery and recapture device comprising:
a handle comprising a jaw control and a lock control; and
an end effector connected to the handle and comprising:
a clevis; and
first and second jaws:

connected to the clevis;
operatively connected to the jaw control to actively articulate at least one of the first and second jaws with respect to the other; and
having respective first and second connectors;
wherein:
the first connector of the first jaw has a given length and the second connector of the second jaw has a length different from the given length;
at least one of the first and second connectors comprises a second portion of the lock and is operatively connected to the lock control to removably lock with the first portion of the lock; and
at least one of the first and second connectors:
is pivotably connected to a respective one of the first and second jaws;
is biased to an approximately parallel orientation with respect to the other one of the first and second connectors; and
is configured to pivot passively from the approximately parallel orientation.

34. The system according to claim 33, wherein:
the first connector comprises the second portion of the lock and is operatively connected to the lock control to removably lock with the first portion of the lock; and
the second connector:
is pivotably connected to the respective one of the first and second jaws;
is biased to an approximately parallel orientation with respect to the first connector; and
is configured to pivot passively from the approximately parallel orientation.

35. The system according to claim 33, wherein the first connector:
comprises the second portion of the lock and is operatively connected to the lock control to removably lock with the first portion of the lock;
is pivotably connected to the respective one of the first and second jaws;
is biased to an approximately parallel orientation with respect to the second connector; and
is configured to pivot passively from the approximately parallel orientation.

36. The system according to claim 35, wherein the second connector:
comprises the second portion of the lock and is operatively connected to the lock control to removably lock with the first portion of the lock;
is pivotably connected to the respective one of the first and second jaws;
is biased to an approximately parallel orientation with respect to the first connector; and
is configured to pivot passively from the approximately parallel orientation.

* * * * *